(12) United States Patent
Xiao et al.

(10) Patent No.: US 9,057,077 B2
(45) Date of Patent: Jun. 16, 2015

(54) ENGINEERING BROAD-SPECTRUM DISEASE RESISTANCE AGAINST HAUSTORIUM-FORMING PATHOGENS USING RPW8 AS A DELIVERY VEHICLE

(75) Inventors: Shunyuan Xiao, Rockville, MD (US); **Wenming W

(56) References Cited

OTHER PUBLICATIONS

Falk, A., Feys, B.J., Frost, L.N., Jones, J.D., Daniels, M.J., and Parker, J.E. (1999). EDS1, an essential component of R gene-mediated disease resistance in *Arabidopsis* has homology to eukaryotic lipases. Proc Natl Acad Sci U S A 96, 3292-3297.

Gil, F., and Gay, J.L. (1977). Ultrastructural and physiological properties of the host interfacial components of the haustoria of *Erysiphe pisi* in vivo and in vitro. Physiol. Plant Pathol. 10, 1-12.

Hahn, M., and Mendgen, K. (2001). Signal and nutrient exchange at biotrophic plant—fungus interfaces. Current opinion in plant biology 4, 322-327.

Halterman, D., Zhou, F., Wei, F., Wise, R.P., and Schulze-Lefert, P. (2001). The MLA6 coiled-coil, NBS-LRR protein confers AvrMla6-dependent resistance specificity to *Blumeria graminis* f. sp. *hordei* in barley and wheat. Plant J 25, 335-348.

Halterman, D.A., and Wise, R.P. (2004). A single-amino acid substitution in the sixth leucine-rich repeat of barley MLA6 and MLA13 alleviates dependence on RAR1 for disease resistance signaling. Plant J 38, 2 15-226.

Hammond-Kosack, K.E., and Jones, J.D. (1997). Plant Disease Resistance Genes. Annu Rev Plant Physiol Plant Mol Biol 48, 575-607.

Heath, M.C., and Heath, I.B. (1971). Ultrastructure of an immune and susceptible reaction of cowpea leaves to rust infection. Physiol. Mol. Plant Pathol. 1, 277-287.

Huckelhoven, R., Fodor, J., Preis, C., and Kogel, K.H. (1999). Hypersensitive cell death and papilla formation in barley attacked by the powdery mildew fungus are associated with hydrogen peroxide but not with salicylic acid accumulation. Plant Physiol 119, 1251-1260.

Huynh, K.K., Eskelinen, E.L., Scott, C.C., Malevanets, A., Saftig, P., and Grinstein, S. (2007). LAMP proteins are required for fusion of lysosomes with phagosomes. The EMBO journal 26, 3 13-324.

Jacobs, A.K., Lipka, V., Burton, R.A., Panstruga, R., Strizhov, N., Schulze-Lefert, P., and Fincher, G.B. (2003). An *Arabidopsis* Callose Synthase, GSL5, Is Required for Wound and Papillary Callose Formation. Plant Cell 15, 2503-25 13.

Jones, J.D., and Dangl, J.L. (2006). The plant immune system. Nature 444, 323-329.

Koh, S., Andre, A., Edwards, H., Ehrhardt, D., and Somerville, S. (2005). *Arabidopsis thaliana* subcellular responses to compatible *Erysiphe cichoracearum* infections. Plant J 44, 5 16-529.

Kwon, C., Neu, C., Pajonk, S., Yun, H.S., Lipka, U., Humphry, M., Bau, S., Straus, M., Kwaaitaal, M., Rampelt, H., El Kasmi, F., Jurgens, G., Parker, J., Panstruga, R., Lipka, V., and Schulze-Lefert, P. (2008). Co-option of a default secretory pathway for plant immune responses. Nature 451, 835-840.

Lanzetti, L. (2007). Actin in membrane trafficking. Curr Opin Cell Biol 19, 453-458.

Lipka, V., Dittgen, J., Bednarek, P., Bhat, R., Wiermer, M., Stein, M., Landtag, J., Brandt, W., Rosahl, S., Scheel, D., Llorente, F., Molina, A., Parker, J., Somerville, S., and Schulze-Lefert, P. (2005). Pre- and postinvasion defenses both contribute to nonhost resistance in *Arabidopsis*. Science (New York, N.Y 310, 1180-1183.

Mackie, A.J., Roberts, A.M., Callow, J.A., and Green, J.R. (1991). Molecular Differentiation in Pea Powdery-Mildew Haustoria—Identification of a 62-Kda N-Linked Glycoprotein Unique to the Haustorial Plasma-Membrane. Planta 183, 399-408.

Manners, J.M., and Gay, J.L. (1982). Transport, Translocation and Metabolism of C-14-Labeled Photosynthates at the Host-Parasite Interface of *Pisum-sativum* and *Erysiphe-pisi*. New Phytologist 91, 22 1-244.

Mellersh, D.G., and Heath, M.C. (2003). An investigation into the involvement of defense signaling pathways in components of the nonhost resistance of *Arabidopsis thaliana* to rust fungi also reveals a model system for studying rust fungal compatibility. Mol Plant Microbe Interact 16, 398-404.

Meyer, D., Pajonk, S., Micali, C., O'Connell, R., and Schulze-Lefert, P. (2008). Extracellular transport and integration of plant secretory proteins into pathogen-induced cell wall compartments. Plant J.

Miklis, M., Consonni, C., Bhat, R.A., Lipka, V., Schulze-Lefert, P., and Panstruga, R. (2007). Barley Mlo Modulates Actin-dependent and Actin-independent Antifungal Defence Pathways at the Cell Periphery. Plant Physiol.

Morel, J.B., and Dangl, J.L. (1997). The hypersensitive response and the induction of cell death in plants. Cell Death and Differentiation 4, 67 1-683.

Mou, Z., Fan, W., and Dong, X. (2003). Inducers of plant systemic acquired resistance regulate NPR1 function through redox changes. Cell 113, 93 5-944.

Nishimura, M.T., Stein, M., Hou, B.H., Vogel, J.P., Edwards, H., and Somerville, S.C. (2003). Loss of a callose synthase results in salicylic acid-dependent disease resistance. Science (New York, N.Y 301, 969-972.

Opalski, K.S., Schultheiss, H., Kogel, K.H., and Huckelhoven, R. (2005). The receptor-like MLO protein and the RAC/ROP family G-protein RACB modulate actin reorganization in barley attacked by the biotrophic powdery mildew fungus *Blumeria graminis* f.sp. *hordei*. Plant J 41, 29 1-303.

Orgil, U., Araki, H., Tangchaiburana, S., Berkey, R., and Xiao, S. (2007). Intraspecific Genetic Variations, Fitness Cost and Benefit of RPW8, A Disease Resistance Locus in *Arabidopsis thaliana*. Genetics 176, 23 17-2333.

Roberts, A.M., Mackie, A.J., Hathaway, V., Callow, J.A., and Green, J.R. (1993). Molecular Differentiation in the Extrahaustorial Membrane of Pea Powdery Mildew Haustoria at Early and Late Stages of Development. Physiological and Molecular Plant Pathology 43, 147-160.

Schulze-Lefert, P., and Panstruga, R. (2003). Establishment of biotrophy by parasitic fungi and reprogramming of host cells for disease resistance Annu Rev Phytopathol 41, 641-667.

Searle, S., Bright, N.A., Roach, T.I., Atkinson, P.G., Barton, C.H., Meloen, R.H., and Blackwell, J.M. (1998). Localisation of Nramp1 in macrophages: modulation with activation and infection. Journal of cell science 111 ( Pt 19), 2855-2866.

Shen, Q.H., Saijo, Y., Mauch, S., Biskup, C., Bieri, S., Keller, B., Seki, H., Ulker, B., Somssich, I.E., and Schulze-Lefert, P. (2007). Nuclear activity of MLA immune receptors links isolate-specific and basal disease-resistance responses. Science (New York, N.Y 315, 1098-1103.

Soylu, S., Keshavarzi, M., Brown, I., and Mansfield, J.W. (2003). Ultrastructural characterisation of interactions between *Arabidopsis thaliana* and *Albugo candida*. Physiological and Molecular Plant Pathology 63, 201-211.

Stein, M., Dittgen, J., Sanchez-Rodriguez, C., Hou, B.H., Molina, A., Schulze-Lefert, P., Lipka, V., and Somerville, S. (2006). *Arabidopsis* PEN3/PDR8, an ATP binding cassette transporter, contributes to nonhost resistance to inappropriate pathogens that enter by direct penetration. Plant Cell 18, 731-746.

Szabo, L.J., and Bushnell, W.R. (2001). Hidden robbers: the role of fungal haustoria in parasitism of plants. Proc Natl Acad Sci U S A 98, 7654-7655.

Tada, Y., Spoel, S.H., Pajerowska-Mukhtar, K., Mou, Z., Song, J., Wang, C., Zuo, J., and Dong, X. (2008). Plant immunity requires conformational charges of NPR1 via S-nitrosylation and thioredoxins. Science (New York, N.Y 321, 952-956.

Takemoto, D., Jones, D.A., and Hardham, A.R. (2003). GFP-tagging of cell components reveals the dynamics of subcellular re-organization in response to infection of *Arabidopsis* by oomycete pathogens. Plant J 33, 775-792.

Uemura, T., Ueda, T., Ohniwa, R.L., Nakano, A., Takeyasu, K., and Sato, M.H. (2004). Systematic analysis of SNARE molecules in *Arabidopsis*: dissection of the post-Golgi network in plant cells. Cell Struct Funct 29, 49-65.

Voegele, R.T., Struck, C., Hahn, M., and Mendgen, K. (2001). The role of haustoria in sugar supply during infection of broad bean by the rust fungus *Uromyces fabae*. Proc Natl Acad Sci U S A 98, 8133-8138.

Wang, W., Devoto, A., Turner, J.G., and Xiao, S. (2007). Expression of the membrane-associated resistance protein RPW8 enhances basal defense against biotrophic pathogens. Mol Plant Microbe Interact 20, 966-976.

(56) References Cited

OTHER PUBLICATIONS

Wirthmueller, L., Zhang, Y., Jones, J.D., and Parker, J.E. (2007). Nuclear accumulation of the *Arabidopsis* immune receptor RPS4 is necessary for triggering EDS 1-dependent defense. Curr Biol 17, 2023-2029.

Xiao, S., Ellwood, S., Findlay, K., Oliver, R.P., and Turner, J.G. (1997). Characterization of three loci controlling resistance of *Arabidopsis thaliana* accession Ms-0 to two powdery mildew diseases. Plant J 12, 757-768.

Xiao, S., Ellwood, S., Calis, O., Patrick, E., Li, T., Coleman, M., and Turner, J.G. (2001). Broad-spectrum mildew resistance in *Arabidopsis thaliana* mediated by RPW8. Science (New York, N.Y 291, 118-120.

Xiao, S., Brown, S., Patrick, E., Brearley, C., and Turner, J.G. (2003). Enhanced transcription of the *Arabidopsis* disease resistance genes RPW8.1 and RPW8.2 via a salicylic acid-dependent amplification circuit is required for hypersensitive cell death. Plant Cell 15, 33-45.

Xiao, S., Charoenwattana, P., Holcombe, L., and Turner, J.G. (2003). The *Arabidopsis* genes RPW8.1 and RPW8.2 confer induced resistance to powdery mildew diseases in tobacco. Mol Plant Microbe Interact 16, 289-294.

Xiao, S., Calis, O., Patrick, E., Zhang, G., Charoenwattana, P., Muskett, P., Parker, J.E., and Turner, J.G. (2005). The atypical resistance gene, RPW8, recruits components of basal defence for powdery mildew resistance in *Arabidopsis*. Plant J 42, 95-110.

Yahiaoui, N., Srichumpa, P., Dudler, R., and Keller, B. (2004). Genome analysis at different ploidy levels allows cloning of the powdery mildew resistance gene Pm3b from hexaploid wheat. Plant J 37, 528-53 8.

Yang, Z. (2008). Cell polarity signaling in *Arabidopsis* Annu Rev Cell Dev Biol 24, 55 1-575.

Yun, B.W., Atkinson, H.A., Gaborit, C., Greenland, A., Read, N.D., Pallas, J.A., and Loake, G.J. (2003). Loss of actin cytoskeletal function and EDS1 activity, in combination, severely compromises nonhost resistance in *Arabidopsis* against wheat powdery mildew. Plant J 34, 768-777.

Zhou, F., Kurth, J., Wei, F., Elliott, C., Vale, G., Yahiaoui, N., Keller, B., Somerville, S., Wise, R., and Schulze-Lefert, P. (2001). Cell-autonomous expression of barley Mla1 confers race-specific resistance to the powdery mildew fungus via a Rar1-independent signaling pathway. Plant Cell 13, 337-350.

Wang, W. et al. Expression of the membrane-associated resistance protein RPW8 enhances basal defense against biotrophic pathogens. Molecular Plant-Microbe Interactions, 2007, vol. 20, No. 8, pp. 966-976.

Wang W. et al. Specific targeting of the arabidopis resistance protein RPW8 to the interfacial membrane encasing the fungal haustorium renders broad-spectrum resistance to powdery mildew. The Plant Cell, Sep. 2009, vol. 21, pp. 2898-2913.

* cited by examiner

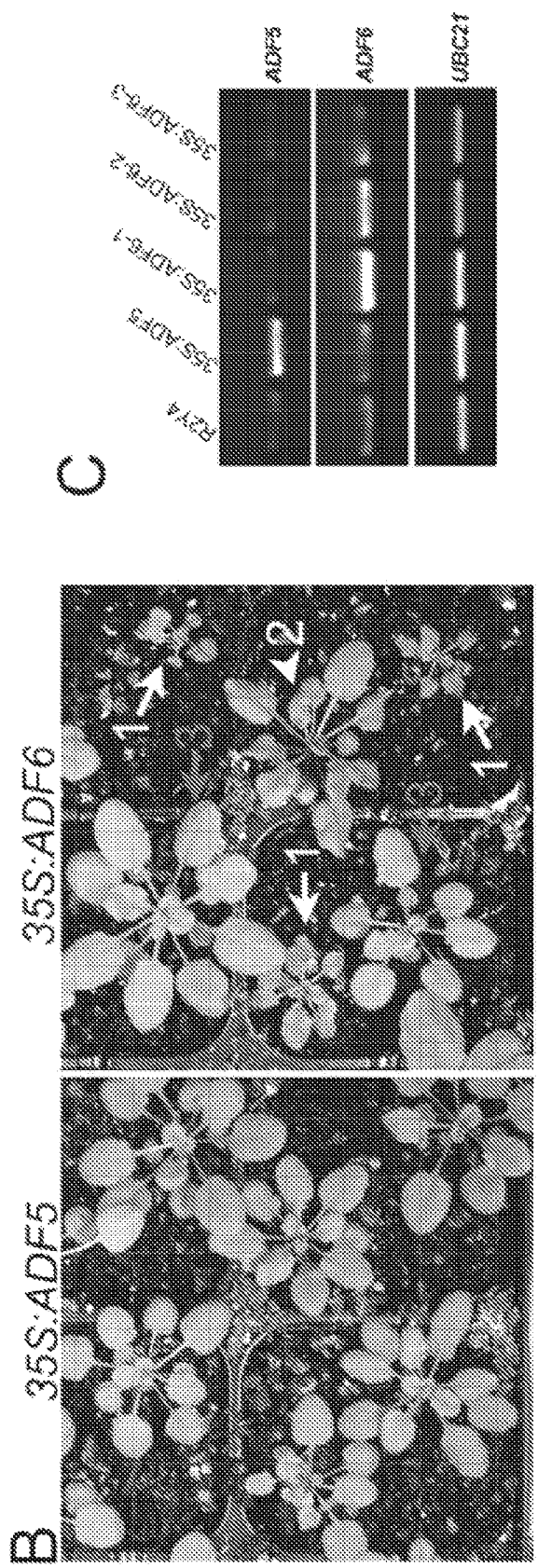
Figure 13 B and C

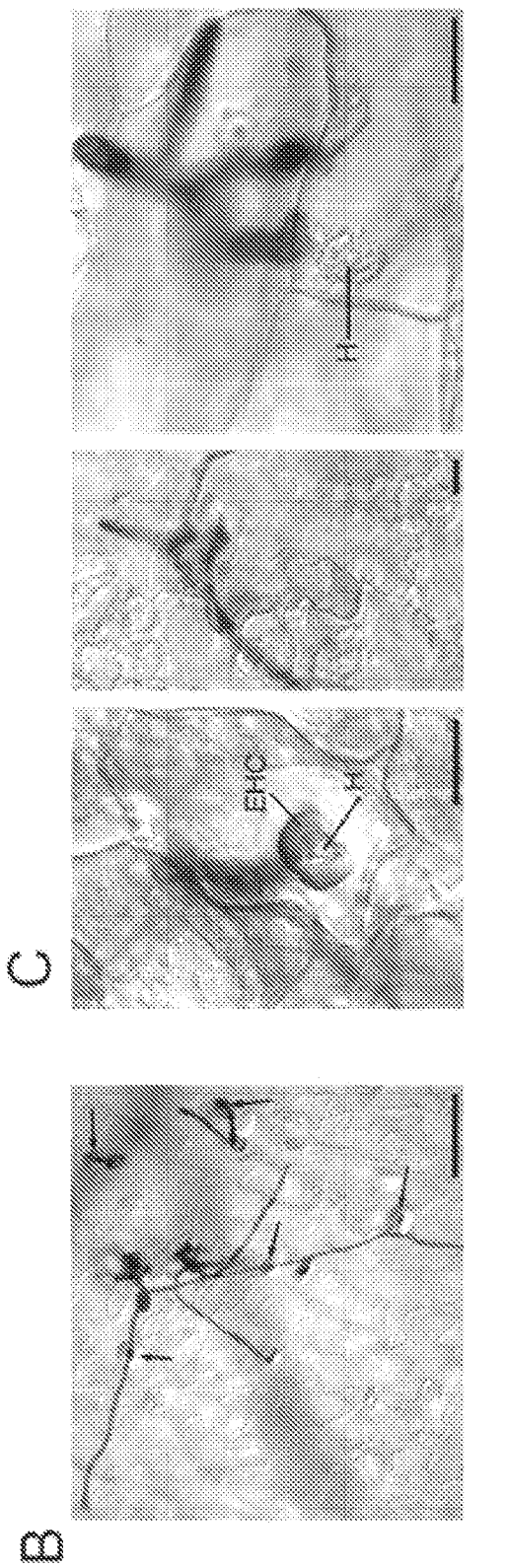
Figure 14 B and C

| Construct | | Schematic Illustration | EHM-Localization | HR & Resistance |
|---|---|---|---|---|
| | | TM   CC1   CC2 | | |
| 1 | R82 | ▬▬▬▬▬▬▬ YFP | + | + |
| 2 | Δ2-22 | ▬▬▬▬▬▬ YFP | − | − |
| 3 | Δ2-30 | ▬▬▬▬▬▬ YFP | − | − |
| 4 | Δ145-174 | ▬▬▬▬▬ YFP | + | + |
| 5 | Δ138-174 | ▬▬▬▬▬ YFP | + | + |
| *6 | Δ118-174 | ▬▬▬▬ YFP | + | − |
| 7 | Δ109-174 | ▬▬▬ YFP | − | − |
| 8 | Δ89-174 | ▬▬ YFP | − | − |
| 9 | Δ30-174 | ▬ YFP | − | − |
| 10 | Δ65-93 | ▬▬▬▬ YFP | + | − |
| 11 | Δ65-93 Δ138-174 | ▬▬▬ YFP | + | − |
| 12 | YFP-R82 | YFP ▬▬▬▬▬▬ | + | + |
| 13 | YFP-LTl6b -Δ1-31 | YFP ▬▬▬▬▬ | + | − |
| *14 | YFP-LTl6b- Δ1-93 | YFP ▬▬▬ | + | − |

Figure 21

ENGINEERING BROAD-SPECTRUM DISEASE RESISTANCE AGAINST HAUSTORIUM-FORMING PATHOGENS USING RPW8 AS A DELIVERY VEHICLE

CROSS-REFERENCE TO RELATED APPLICATIONS

This application is filed under the provisions of 35 U.S.C. §371 and claims the priority of International Patent Application No. PCT/US2010/029134 filed on Mar. 30, 2010, which in turn claims priority to U.S. Provisional Patent Application No. 61/164,540 filed on Mar. 30, 2009 the contents of which are hereby incorporated by reference herein for all purposes.

BACKGROUND OF THE INVENTION

1. Field of the Invention

The present invention relates to inhibition of plant pathogens, and more specifically, to the increased expression of RPW8 with an increased levels at the extrahaustorial membrane and subsequent induction of pathogen inhibition reactions.

2. Background of Related Technology

Plant diseases caused by various pathogens pose a constant threat to human food security. Plant defense against invading obligate, biotrophic haustorium-forming fungal and oomycete pathogens occurs at pre-invasion and post-invasion stages (Lipka et al., 2005). Pre-invasion resistance protects plants from non-adapted pathogens, by blocking their entry into the host cell (Collins et al., 2003; Lipka et al., 2005; Stein et al., 2006). One common induced cellular defense response is the deposition of defense chemicals including callose (β-1, 3-glucan) at the site of penetration, resulting in cell-wall apposition, a subcellular structure also known as a papilla (Aist, 1976; Huckelhoven et al., 1999).

Plants have evolved at least two distinct mechanisms for induction of pre-invasion resistance. The first engages the PEN1 syntaxin-containing SNARE (soluble N-ethylmaleimide-sensitive factor attachment protein receptor) complex-dependent exocytosis pathway for delivering yet-to-be-defined antimicrobial materials to the site of penetration (Collins et al., 2003; Kwon et al., 2008). The second involves the accumulation of 4-methoxyindol-3-ylmethylglucosinolate (which leads to callose formation) through hydrolysis of indole glucosinolates by the PEN2 atypical myrosinase and action of the plasma membrane-localized PEN3 ATP-binding cassette transporter (Lipka et al., 2005; Stein et al., 2006; Bednarek et al., 2009; Clay et al., 2009). Loss-of-function of PEN1, PEN2 or PEN3 in *Arabidopsis* each results in higher penetration rates of non-adapted powdery mildew pathogens.

For an adapted pathogen, however, pre-invasion resistance is ineffective; the pathogen has evolved the ability to penetrate the host cell wall underneath the appressorium and produce a feeding structure, the haustorium, presumably through invagination of the host plasma membrane (PM). This interfacial membrane, termed extrahaustorial membrane (EHM) (Mackie et al., 1991), is poorly characterized, and to date not a single protein either from the host or the pathogen has been definitively identified as an EHM-resident. Apart from nutrient take-up from the host cell (Manners and Gay, 1982; Voegele et al., 2001), the haustorium functions to secrete effector proteins into the host cell across the interface to suppress host defenses including those elicited upon recognition of microbe-associated molecular patterns (MAMPs) by cell surface receptors (Catanzariti et al., 2007). The formation and sustained functioning of the haustorium enables successful colonization of the invading pathogen on the plant, and establishment of long-term parasitic relationship with the host.

Facing selective pressure imposed by the pathogens, plants have evolved post-invasion resistance mechanisms, often controlled by dominant resistance (R) genes, whose products directly or indirectly detect specific pathogen effectors and trigger effective defense responses (Jones and Dangl, 2006). R protein-triggered resistance to various pathogens is normally race-specific and only effective against pathogen strains expressing the cognate effector protein recognized by the R protein, and often associated with a hypersensitive response (HR), which is manifested as rapid death of the invaded cell and in some cases a few surrounding cells (Hammond-Kosack and Jones, 1997; Morel and Dangl, 1997; Schulze-Lefert and Panstruga, 2003). Most characterized plant R proteins belong to members of the nucleotide-binding-site, leucine-rich-repeat (NB-LRR) protein superfamily (Jones and Dangl, 2006). Several isolated powdery mildew resistance genes belong to this class. Those include the R genes at the Mla locus of barley (Halterman et al., 2001; Zhou et al., 2001; Halterman and Wise, 2004) and Pm3b of wheat (Yahiaoui et al., 2004).

Identification and utilization of naturally evolved plant disease resistance (R) genes provide the best way to control crop disease problems. Having been subject to the long-term "arms-race" between plants and pathogens, most R genes are highly specialized in activating resistance to only one or a few strains of a particular pathogen and they can be defeated by the faster-evolving pathogens in a short period of time. Durable and broad-spectrum R genes are thus among the most desirable for sustainable agriculture. The first durable and broad-spectrum R gene RPW8 (AF273059) isolated from *Arabidopsis thaliana* confers resistance to powdery mildew diseases caused by *Erysiphe* spp, an important group of fungal pathogens belonging to Ascomycete (S. Xiao, J. G. Turner, M. Coleman, and S. Ellwood, Plant resistance gene, PCT Application No. WO0198479, Plant Bioscience Limited (GB), UK).

The two homologous *Arabidopsis* R genes RPW8.1 and RPW8.2 from the Ms-0 accession confer broad-spectrum (Xiao et al., 2001) to host-adapted *Golovinomyces* spp. fungi belonging to Ascomycete, which are the causal agents of powdery mildew diseases on numerous dicot plant species (Braun, 1987). RPW8.1 and RPW8.2 encode proteins that contain an N-terminal transmembrane (TM) and 1-2 coiled-coil (CC) domains (Xiao et al., 2001), and thus are placed in an unusual class of R genes (Dangl and Jones, 2001). Despite their atypical predicted protein structure, RPW8.1 and RPW8.2 (both together are referred to as RPW8 unless otherwise indicated) activate HR and other defense responses via the conserved salicylic acid (SA)-dependent signaling pathway also recruited by a subset of NB-LRR R proteins that contain an N-terminal TIR (toll and interleukin-1 receptor) domain for race-specific resistance (Xiao et al., 2003; Xiao et al., 2005). This implies that the broad-spectrum mildew resistance is specified by the RPW8 proteins upstream of SA-dependent signaling.

The RPW8 protein activated resistance is poorly understood. Thus it would be advantageous to provide some insight into the activity and capabilities of the RPW8 protein and use such activity to provide a defense against pathogens at the plasma membrane.

SUMMARY OF THE INVENTION

The present invention shows that RPW8 achieves broad-spectrum resistance and the RPW8.2 protein is highly induced by powdery mildew and is specifically targeted to the EHM during haustorium differentiation whereby it enhances formation of a callosic encasement of the haustorial complex (EHC) and onsite accumulation of $H_2O_2$ to constrain the haustorium while reducing oxidative damage to the host cell.

Further, the targeting of RPW8.2 to the EHM requires normal function of actin cytoskeleton but does not seem to engage microtubules. Despite its critical role for the defense function of RPW8.2 (Xiao et al., 2001), salicylic acid signaling is dispensable for targeting of RPW8.2 to the EHM. Evidence is provided herein to show that both EHM-localization and defense activation are required for RPW8.2 to induce cost-effective resistance.

RPW8.2 is therefore the first plant protein ever identified to be specifically translocated to the host extrahaustorial membrane (EHM). The significance of this novel finding is two-fold:

(i) specific labeling of the EHM by RPW8.2 means that one can use RPW8.2 as a tag to identify more conserved EHM-resident proteins and engineer more broad-spectrum resistance against all haustorium-forming pathogens (powdery mildews, rust mildews and downy mildews etc); and (ii) RPW8.2 can be used as a vehicle to deliver peptides (for example, chitinases that degrade fungal cell wall) toxic to fungi at the host-pathogen interface, generating more cost-effective, broad-spectrum resistance against all haustorium-forming pathogens, and transgenic crop cultivars expressing such RPW8-defense peptide fusion proteins provide for wide application in modern sustainable agriculture.

Thus, in one aspect, the present invention provides for a delivery device that is translocated to the host extrahaustorial membrane (EHM), comprising:

(i) a fusion gene comprising a nucleotide sequence encoding a RPW8 protein or a modified sequence essential for EHM targeting with the activity of the RPW8 and a nucleotide sequence encoding an antipathogenic protein that is toxic to a specific haustorium forming pathogen.

In another aspect, the present invention relates to a method for delivery of a toxic agent to a fungal haustorium in an infected plant cell, the method comprising:

(i) introducing a vector into a host plant cell, the vector comprising:

(ii) a fusion gene comprising a nucleotide sequence encoding a RPW8 protein or a modified sequence essential for EHM targeting with the activity of the RPW8 and a nucleotide sequence encoding an antipathogenic protein that is inhibits or reduces growth of haustorium forming pathogen; and (iii) maintaining the cell under appropriate conditions for expression of the RPW8 fusion protein and the transportation of the expressed RPW8 protein and antipathogenic protein to the extrahaustorial membrane.

In yet another aspect, the present invention relates to a method of enhancing disease resistance to pathogen in a plant, the method comprising altering the genetic expression of RPW8 or a RPW8 homolog (SEQ ID NOs: 1 and 8, respectively).

In a further aspect the present invention relates to a method for inhibiting pathogens at the increasing disease resistance in a plant comprising:

introducing into the plant an expression cassette comprising a nucleotide sequence (SEQ ID NO.: 7 or having 90% identity) encoding a RPW8 protein or homolog thereof and a nucleotide sequence encoding an antipathogenic protein that inhibits the growth of a pathogen, wherein the expressed nucleotide sequences inhibit or reduce growth of haustorium forming pathogens relative to a control plant not including the additional nucleotide sequences.

In another aspect the present invention relates to a plant comprising an expression cassette comprising a nucleotide sequence encoding a RPW8 protein or homolog thereof, wherein the expressed nucleotide sequence inhibits or reduces the growth of haustorium forming pathogens. More preferably, the polynucleotide sequence of RPW8 gene is SEQ ID NO. 7 or a polynucleotide sequence having at least 75% identity thereto, and more preferably, at least 90% identity. Optionally the expression cassette further comprises a nucleotide sequence encoding an antipathogenic protein that reduces or inhibits the growth of a pathogen at or near the EHM. The expression cassette can be introduced into the plant using in vitro techniques (e.g. using *Agrobacterium*) or by a sexual cross. The promoter may be constitutive (e.g., the 35S promoter of cauliflower mosaic virus) or inducible.

In another aspect this expression vector is contained within a host cell and transforms the host cell to express RPW8 protein or homolog thereof, wherein the homolog exhibits the function of RPW8.

This invention further provides kits containing any of the vectors or expression cassettes described herein. Such kits can further comprise instructions and control materials.

These and other aspects of the present invention, will be apparent from the detailed description of the invention provided hereinafter.

(A) Lack of RPW8.2-YFP expression in inoculated leaf epidermal cells from 0-15 hpi.

(B) Detection of RPW8.2-YFP expression as sac-like fluorescent objects in inoculated leaf epidermal cells at 20 hpi.

(C) Precise localization of RPW8.2-YFP to the surface of a haustorium (H). Note that the YFP signal stops at the haustorial neck. Arrowheads indicate RPW8.2-YFP-containing vesicles moving toward the haustorium.

(D) A haustorium in a host cell of Col-0 expressing 35S::YFP. Note that the localization pattern of YFP is distinct from (C).

(E) Haustoria encased by RPW8.2-YFP became shrunken (white arrow) or aborted (lack of PT-staining; yellow arrows).

Figure 2:
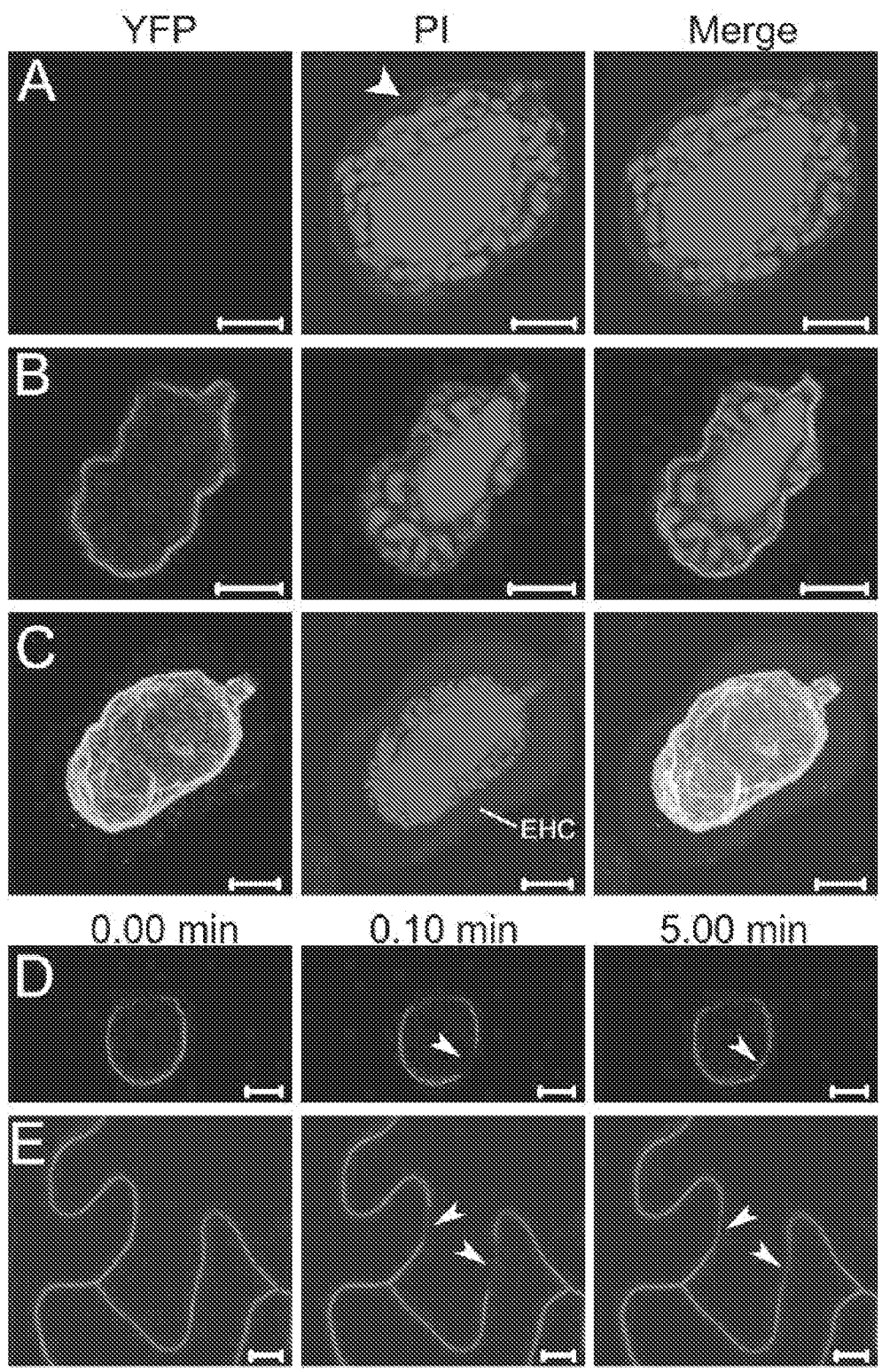

FIG. 2 shows that RPW8.2 is targeted to the extrahaustorial membrane (EHM). Leaves of Col-0 or Col-0 transgenic for RPW8.2-YFP were inoculated with *G. cichoracearum* UCSC1 and used for haustorium isolation at 2 days post-inoculation (dpi). Isolated haustoria were stained with propidium iodide (PT) and imaged by laser scanning confocal microscopy. All scale bars are 5 µm.

(A) A single optical section of an isolated haustorial complex (HC) from Col-0. Note the weakly PT-stained EHM (arrowhead) and numerous lobes emanating from the main body of the haustorium.

(B) One optical section of an isolated HC showing precise co-localization of RPW8.2-YFP with the PT-stained EHM.

(C) An isolated HC from leaf tissues expressing RPW8.2-YFP showing localization of RPW8.2-YFP to the out-surface of the HC. Note the lightly PT-positive encasement of the HC (EHC).

(D, E) Fluorescence recovery after photobleaching on RPW8.2-YFP-labeled EHM (D) and the GFP-STMTP-labeled plasma membrane (E). Arrowheads point the site of photobleaching.

Figure 3:
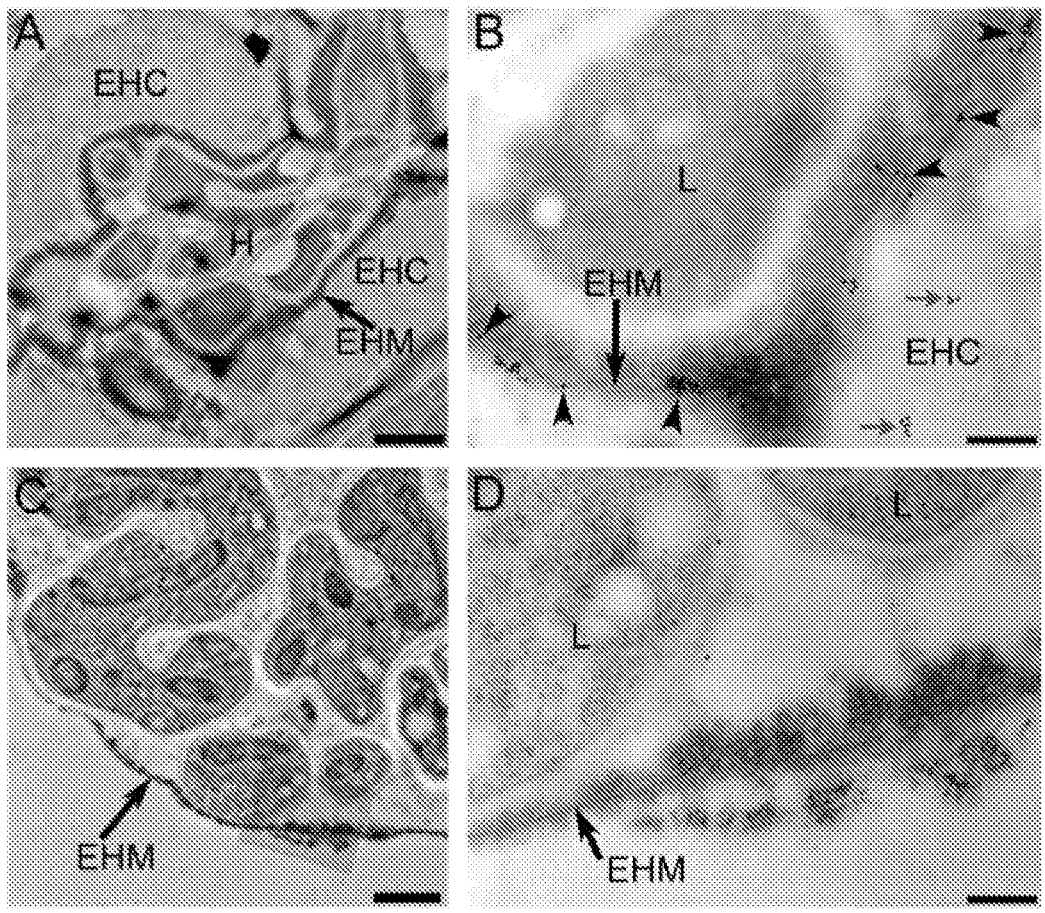

FIG. 3 shows RPW8.2-YFP localization to the EHM revealed by immunogold labeling and transmission electron microscopy.

(A) A lower magnification image of a haustorium (H) in a cell of a transgenic Col-0 line expressing RPW8.2-YFP. Note the encasement of the haustorial complex (EHC). Bar=1 µm.

(B) A close-up of the squared section in (A) showing that the immunogold particles (10 nm) were specifically localized at the EHM (arrowheads) near a haustorial lobe (L). Note a few particles (grey arrows) likely representing RPW8.2-YFP vesicles in the EHC region. Bar=0.2 µm.

(C, D) Sections of a haustorium in a wild-type Col-0 cell at the same magnification as in (A) and (B), respectively.

Figure 4:
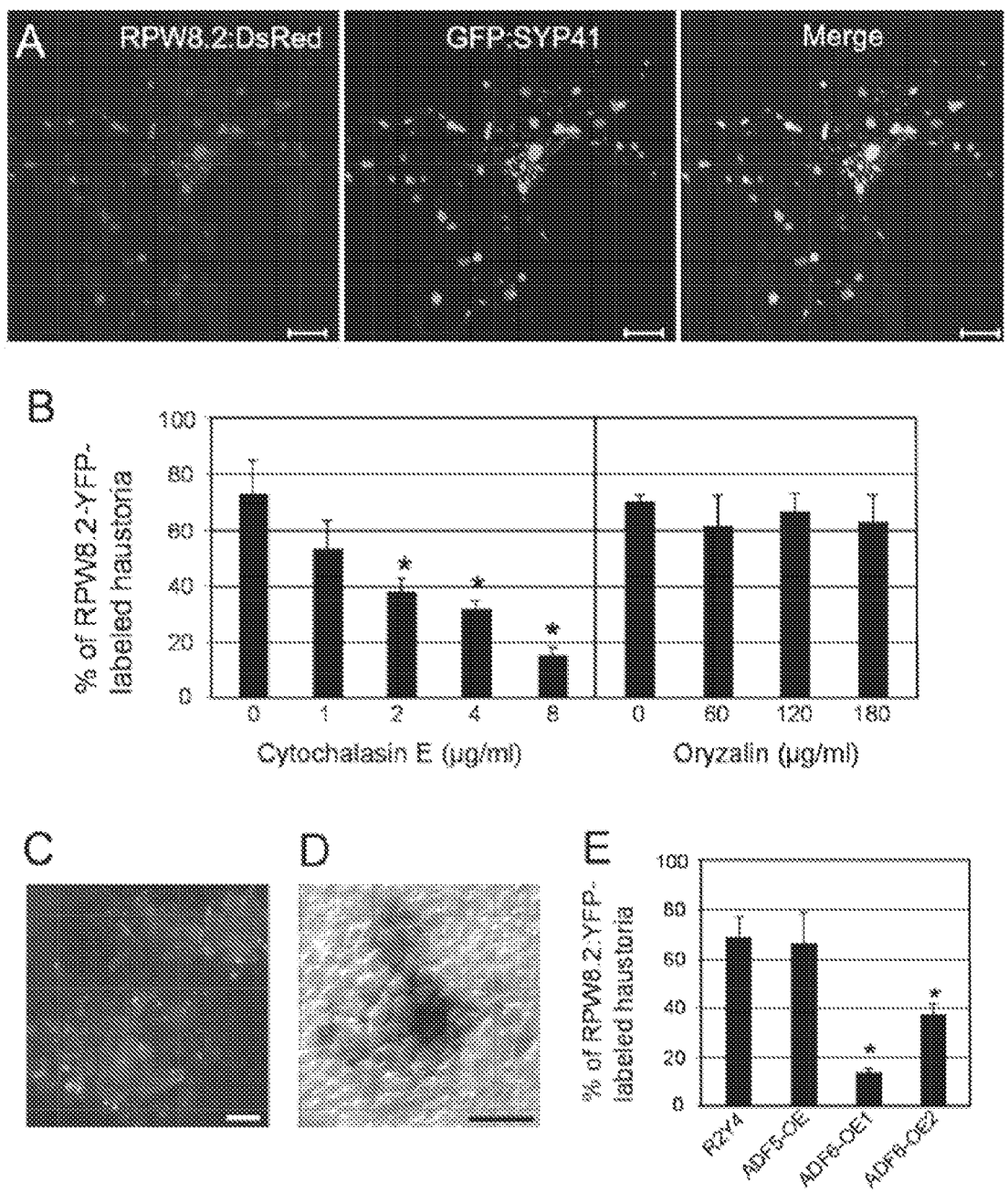

FIG. 4 shows that targeting of RPW8.2 to the EHM requires function of actin cytoskeleton.

(A) Overlapping localization of RPW8.2-DsRed as punctate spots with a trans Golgi Marker (GFP-SYP41). The corresponding DNA constructs were transiently co-expressed in leaves of Col-0 plants via particle bombardment (Wang et al., 2007) and the bombarded leaves were subject to LSCM at 24 hrs after bombardment. Bar=5 µm.

(B) RPW8.2-YFP's localization to the EHM is impeded by cytochalasin E but not obviously affected by oryzalin. Four independent Col-0 lines transgenic for RPW8.2-YFP were used for treatments and examined at ~34 hpi. Data are mean±S.D., derived from one (of three) representative experiments in which >100 haustorial invasion sites per line were evaluated for each concentration. Asterisks indicate significant difference compared with buffer control (P<0.05, n=4, student's t-test).

(C) A representative epifluorescent image showing constitutive punctate RPW8.2-YFP expression (arrows) in leaf epidermal cells from line R2Y4 overexpressing 35S::ADF6. Note the autofluorescence of the cells associated with punctate RPW8.2-YFP. Bar=50 µm.

(D) A representative DAB-trypan blue-stained leaf section showing production/accumulation of $H_2O_2$ (reddish brown) and cell death (blue) in R2Y4 plants overexpressing 35S::ADF6. Bar=50 µm.

(E) RPW8.2-YFP's localization to the EHM is compromised by ADF6 overexpression. R2Y4 or R2Y4 overexpressing ADF5 (ADF5-OE, representing bulked samples from 3 independent lines) or ADF6 (ADF6-OE1 and ADF6-OE2, representing bulked samples from 3 independent lines with reduced plant size and 3 with normal size, respectively) were inoculated with Gc UCSC1 and examined at 2 dpi. Data are mean±S.E., derived from one (of two) representative experiments in which >100 haustorial invasion sites per line were evaluated. Asterisks indicate significant difference compared with R2Y4 (P<0.05, n=3, student's t-test).

Figure 5:
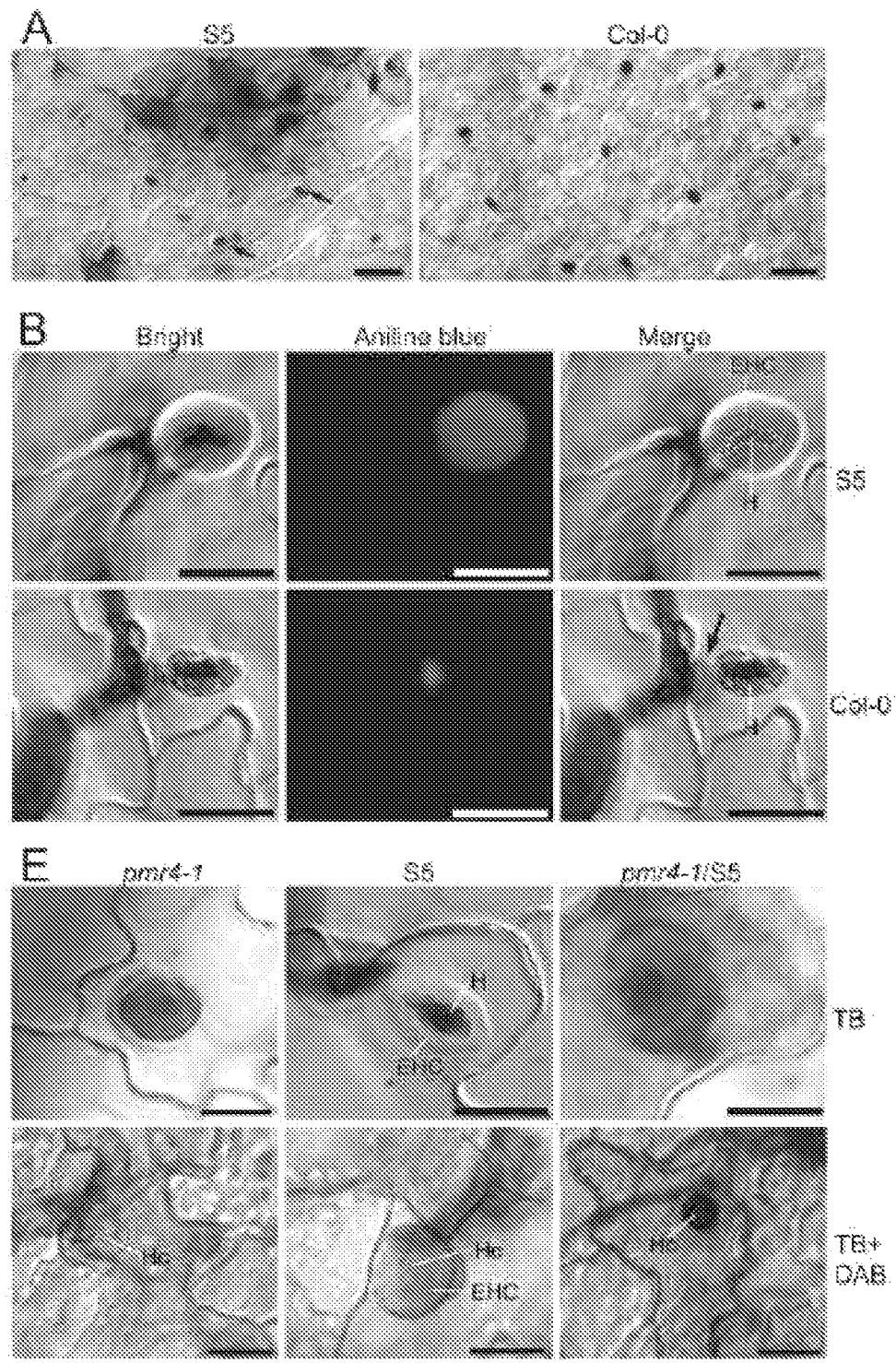
Figure 5:
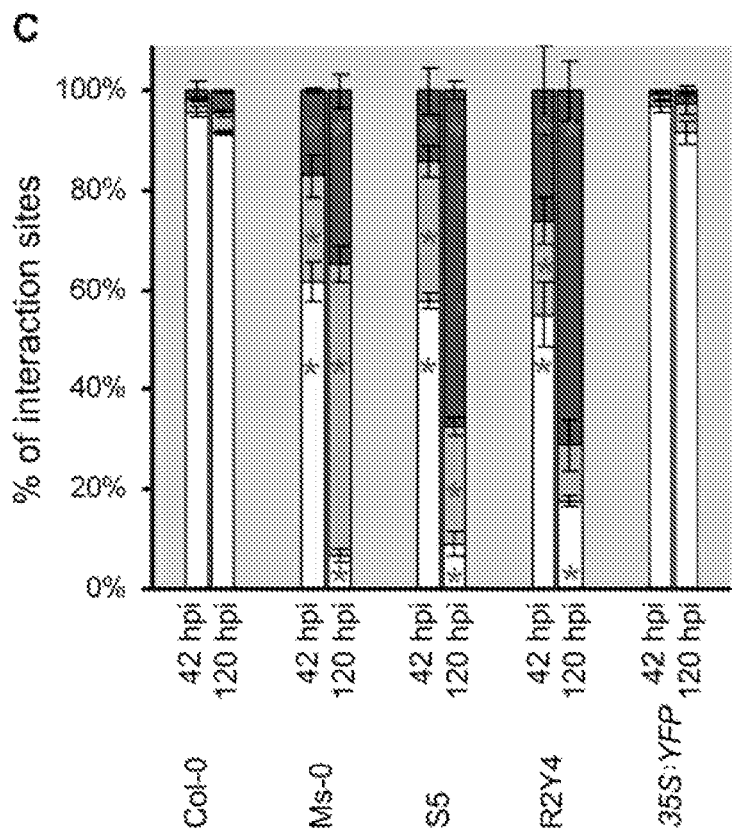
Figure 5:
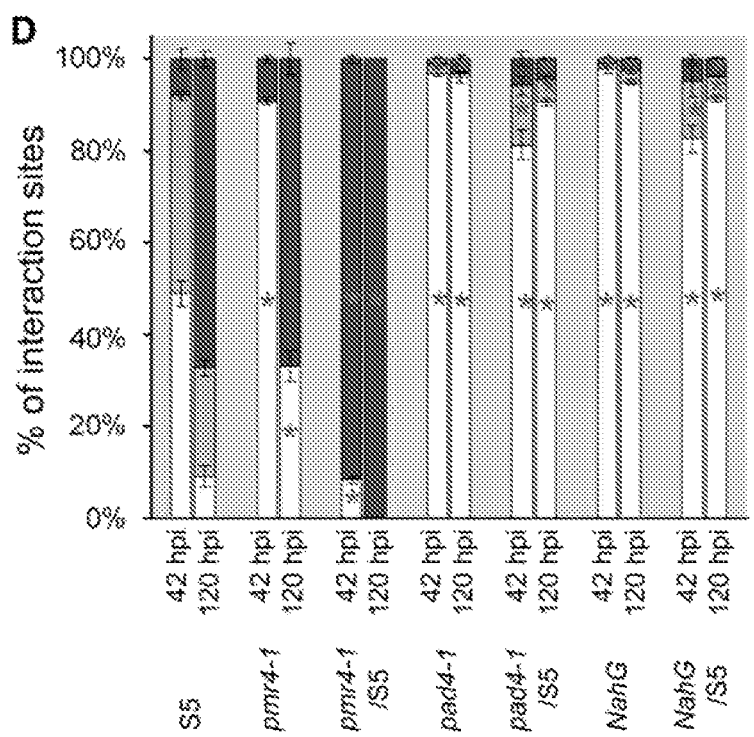

FIG. 5 shows that RPW8 enhances the formation of the encasement of the haustorial complex (EHC) and accumulation of $H_2O_2$ in the haustorial complex (HC). Plants of indicate genotypes including Col-0 lines transgenic for RPW8.2-YFP (R2Y4) or RPW8.1 and RPW8.2 (S5) were inoculated with G. cichoracearum UCSC1 and subject to trypan blue (TB)/aniline blue (AB)/3,3'-diaminobenzidine (DAB) staining (A) Representative leaf sections showing three types of invaded cells: cells containing a haustorium with (black), or without the EHC (yellow arrows) and cells undergoing HR (red arrow) at 5 dpi. Mycelia were removed to aid visualization of haustoria. Bar=50 µm.

(B) Single representative cells containing a shrunken haustorium with the EHC (upper panel) or a healthy haustorium without EHC (lower panel). Note the callose (stained blue by AB) deposition in the EHC and at the penetration site (i.e. the papillae; arrowed). Bar=20 µm.

(C, D) Types and frequencies of host-pathogen interactions at 42 and 120 hpi. White, grey and dark bars indicate frequencies of living cells containing a haustorium without an EHC, living cells containing a haustorium with an EHC and cells undergoing HR, respectively. Data are means±S.E.M., calculated from three duplicated experiments. *Value significantly different from that of Col-0 (C) or S5 (D) (P<0.01; n=3, student's t-test).

(E) Perturbation of the integrity of the EHC by pmr4-1 results in more frequent activation of cell death in the RPW8 background at 48 hpi (upper panel; also see (D)), which is preceded by $H_2O_2$ release from the HC into the cytoplasm (reflected by reddish brown precipitates; lower panel) at 36 hpi. Bar=10 µm.

Figure 6:
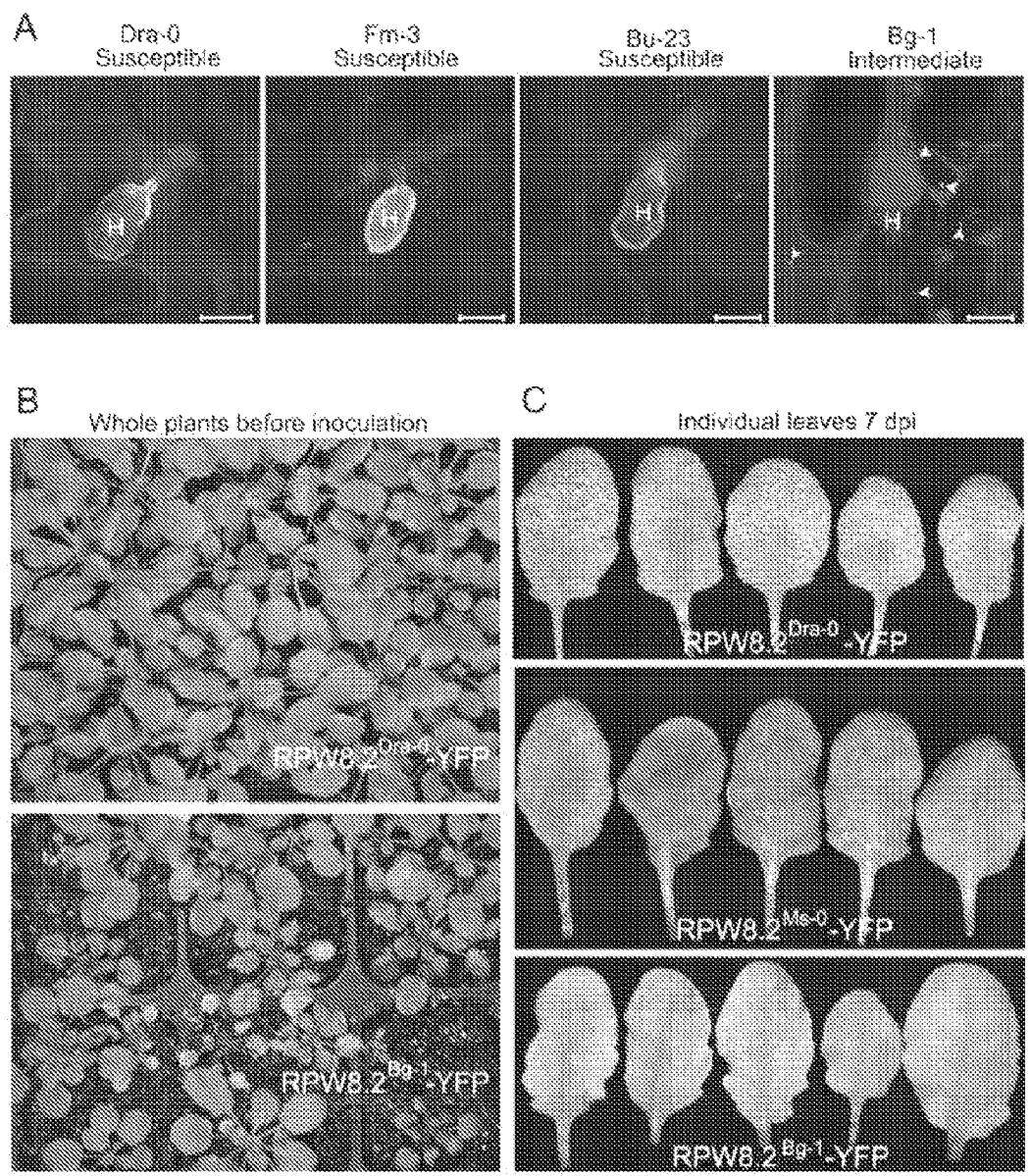

FIG. 6 shows that both defense activation and EHM-localization are required for RPW8.2 to confer cost-effective resistance.

(A) Representative images showing typical localization of RPW8.2 (fused to YFP) encoded by the indicated alleles at 2 dpi. H, haustorium; arrowheads indicate punctate RPW8.2 expression. Bar=10 µm.

(B) Representative 5 week-old T1 lines before inoculation. Note the spontaneous cell death and reduced plant stature in some RPW8.2$^{Bg-1}$-YFP lines.

(C) Disease reaction phenotypes of the indicated lines at 8 dpi. Note the induced massive cell death and fungal growth in the same leaf expressing RPW8.2$^{Bg-1}$-YFP.

Figure 7:
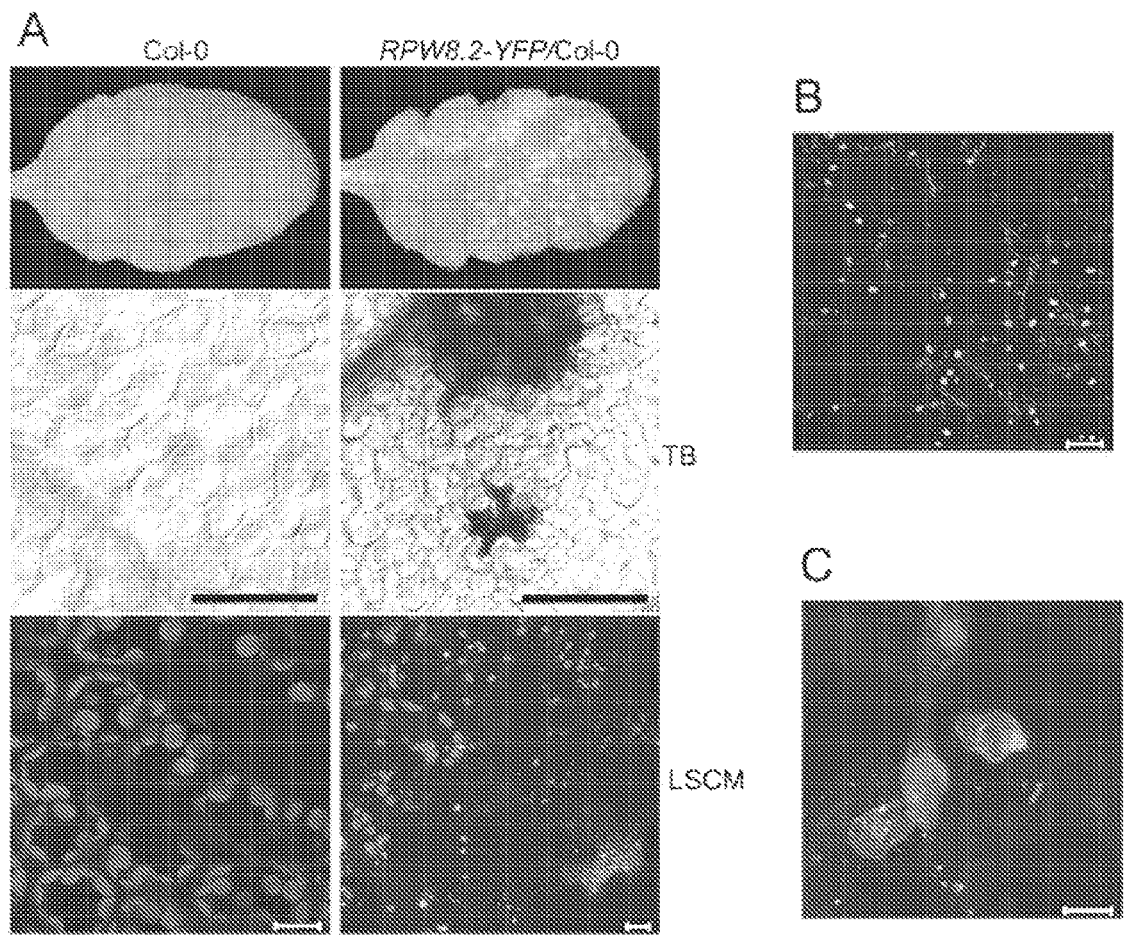

FIG. 7 shows two distinct patterns of RPW8.2-YFP localization.

(A) Punctate expression of RPW8.2-YFP (right bottom corner) in leaves of Col-0 plants overexpressing RPW8.2-YFP from the native promoter is associated with cell death, which is visible to the naked eye and revealed by trypan blue (TB) staining (B) Association of RPW8.2-YFP expression as sac-like structures with fungal mycelia of G cichoracearum UCSC1 which are stained red by propidium iodide at 3 dpi.

(C) A representative LSCM image showing two haustoria targeted by RPW8.2-YFP at two different stages. Scale bars are 100 µm for TB images and 10 µm for LSCM images.

Figure 8:
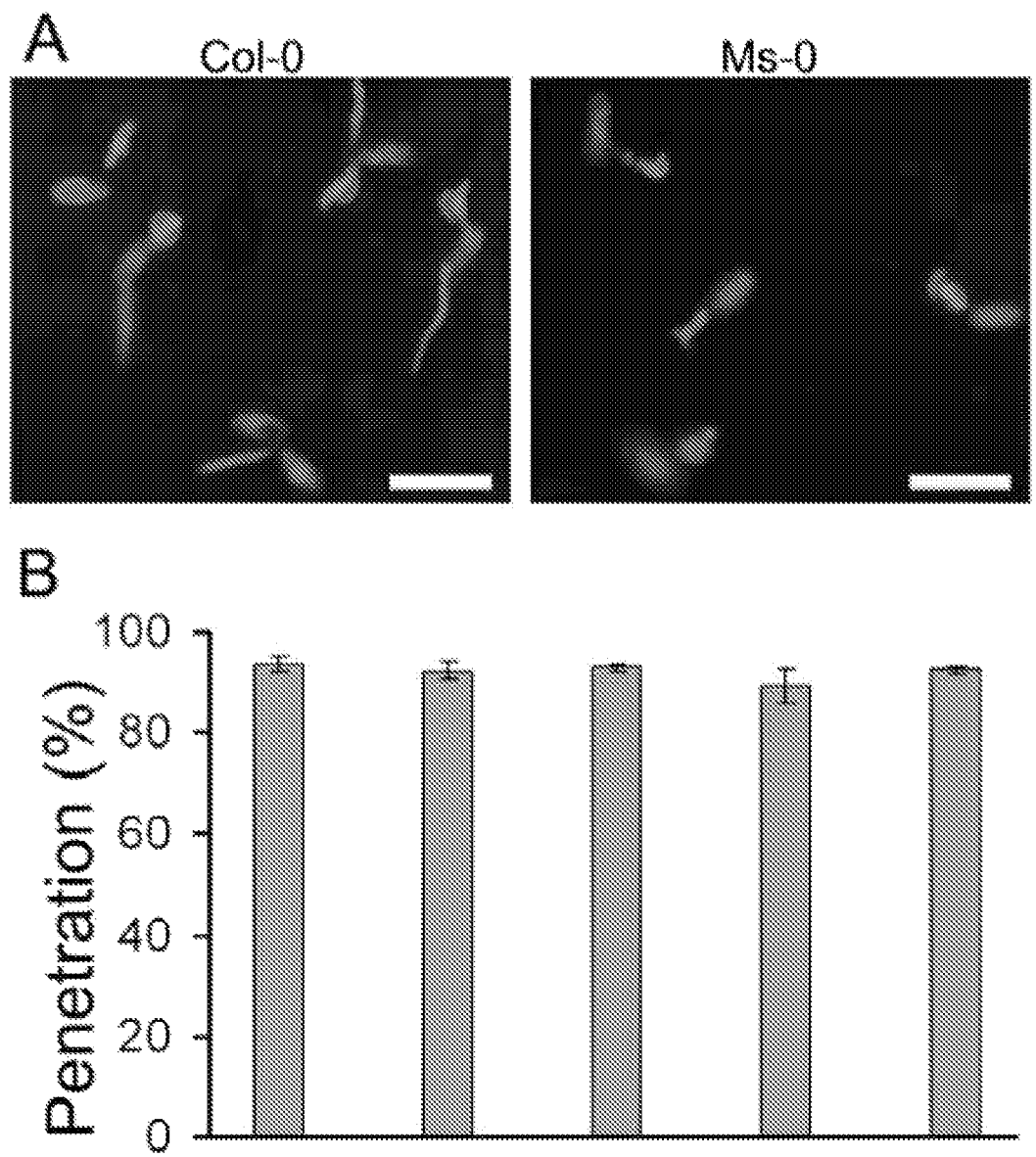

FIG. 8 shows that RPW8 does not activate pre-penetration resistance.

(A) Visualization of host penetration of G cichoracearum UCSC1 at 24 hpi. Conidia were stained red by propidium iodide and callose deposited at the site of successful penetration was stained blue by aniline blue. Bars=50 µm.

(B) Frequencies of fungal entries in leaf epidermal cells of the indicated genotypes at 24 hpi. S5 is a Col-0 transgenic line carrying a single copy of RPW8 under control of the native promoter. Data are mean±S.E.M. (P>0.1, n=3, student's t-test), collected from three duplicated evaluations of >200 interaction sites for each genotype.

Figure 9:
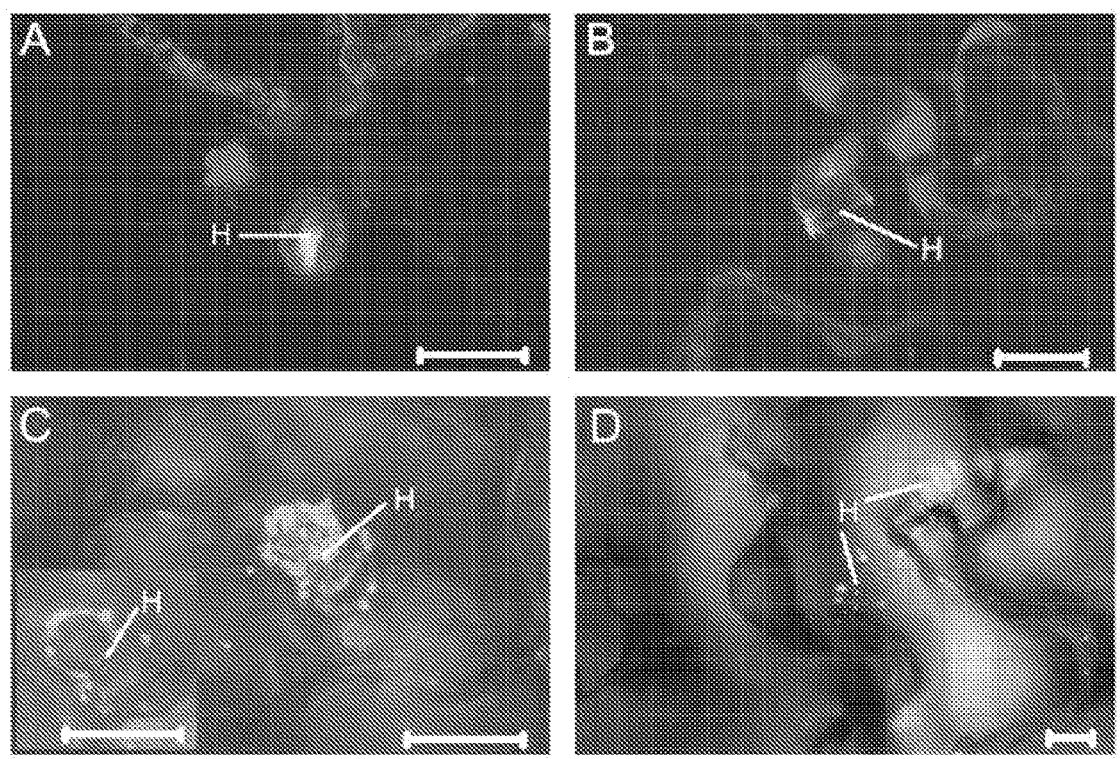

FIG. 9 shows that RPW8.2-YFP is targeted to the periphery of haustoria of other pathogens. (A, B) RPW8.2-YFP is localized at the periphery of haustoria (H) of *Blumeria graminis* f. sp. *hordei* in epidermal cells of eds1-2 plants expressing RPW8.2-YFP. The image in (A) shows an aborted haustorium targeted by RPW8.2-YFP. Note that RPW8.2-YFP can also be found in the EHC. The image in (B) shows a mature haustorium half-encased by RPW8.2-YFP-labeled EHM. The pictures were taken at 28 hpi. Bar=10 μm. (C, D) RPW8.2-YFP is localized at the periphery of haustoria (H) of *Hyaloperonospora parasitica* Noco2 in epidermal cells of Col-0 plants expressing RPW8.2-YFP. The inset in (C) is a single optical section of the same image shown. The oomycete haustoria are recognizable under DIC microscopy (D). The images were collected at 4 dpi. Bar=10 μm.

Figure 10:
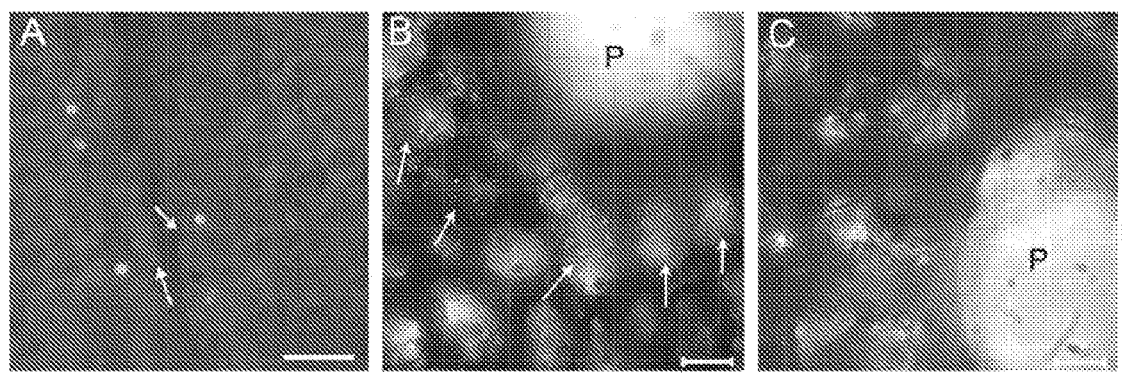

FIG. 10 shows that plasma membrane damage/repair caused by wounding does not induce RPW8.2-YFP expression and plasma membrane-localization. *G cichoracearum* UCSC1-inoculated leaves (2 dpi) of Col-0 lines expressing RPW8.2-YFP were cuts with a pair of sharp scissors (A) or gently pinpricked (P) with fine cactus thorns soaked with 1 M SA (to induce RPW8 expression) (B) or water (C) on the leaf surface and examined for RPW8.2-YFP expression under an epifluorescence microscope or by LSCM at 24 hrs after treatments. Note that there is no YFP signal in the plasma membrane of any damaged cells including those containing a haustorium targeted by RPW8.2-YFP or having punctate RPW8.2-YFP expression (indicated by arrows). Scale bars are 100 μm (A), 20 μm (B, C).

Figure 11:
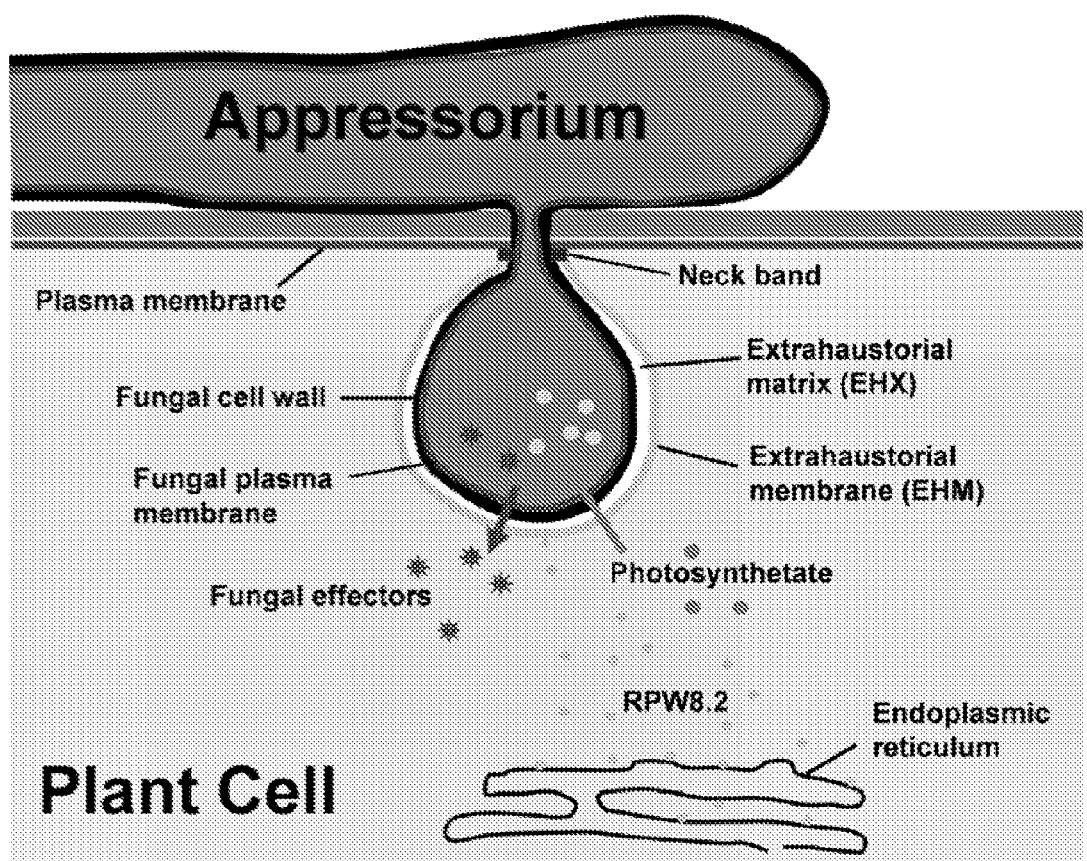

FIG. 11 shows a cartoon illustrating a fungal haustorium developing into an invaginated epidermal cell and the targeting of RPW8.2 to the EHM.

Figure 12:
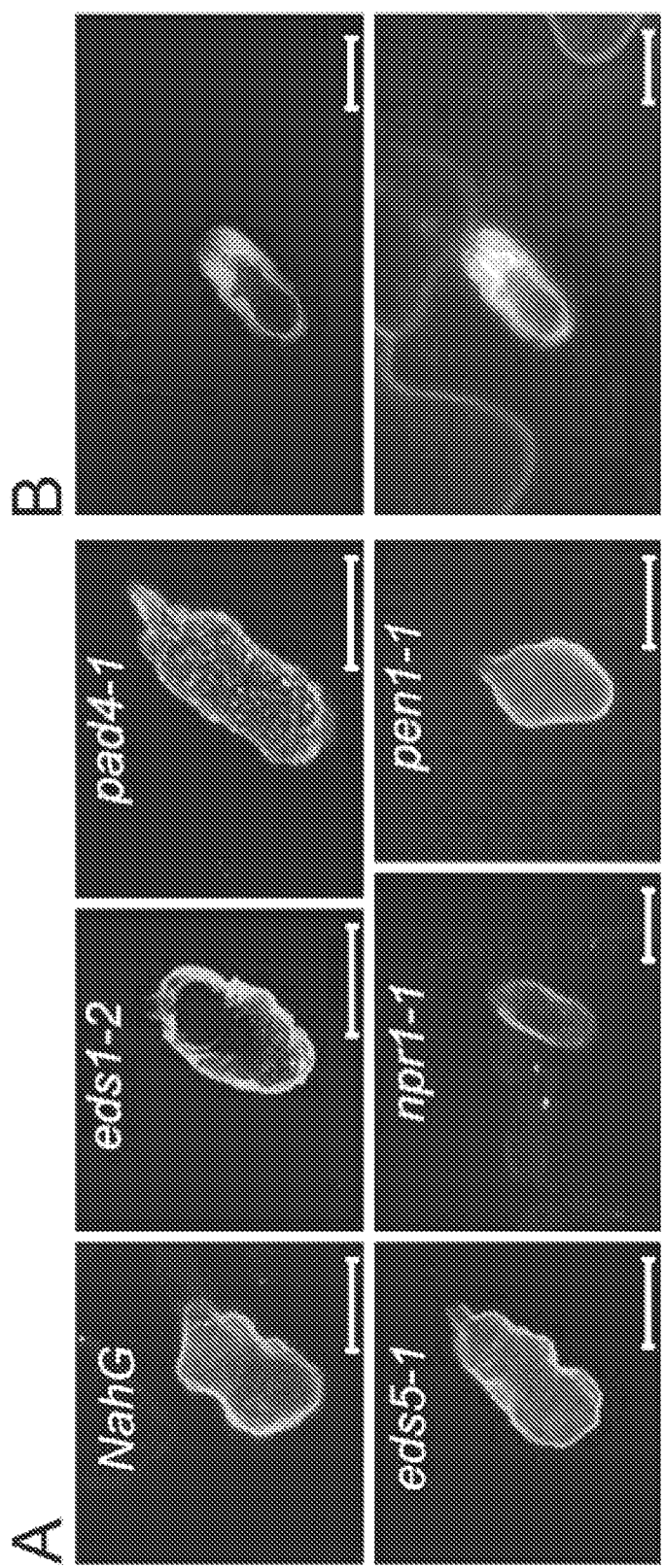

FIG. 12 shows that RPW8.2's translocation to the EHM does not require SA-signaling and is PEN1-independent/redundant.

(A) Representative laser scanning confocal microscopy images (LSCM) of RPW8.2's EHM localization in the indicated genotypes expressing RPW8.2-YFP as a transgene from the native promoter.

(B) A single optical section (upper) and a projection from Z-stacks (lower) of an LSCM image showing differential localization of RPW8.2-DsRed and GFP-PEN1 in the pen1-1 mutation background. Note that GFP-PEN1 is localized in the normal plasma membrane and inside the EHC region without obvious colocalization with RPW8.2-DsRed.

Figure 13:
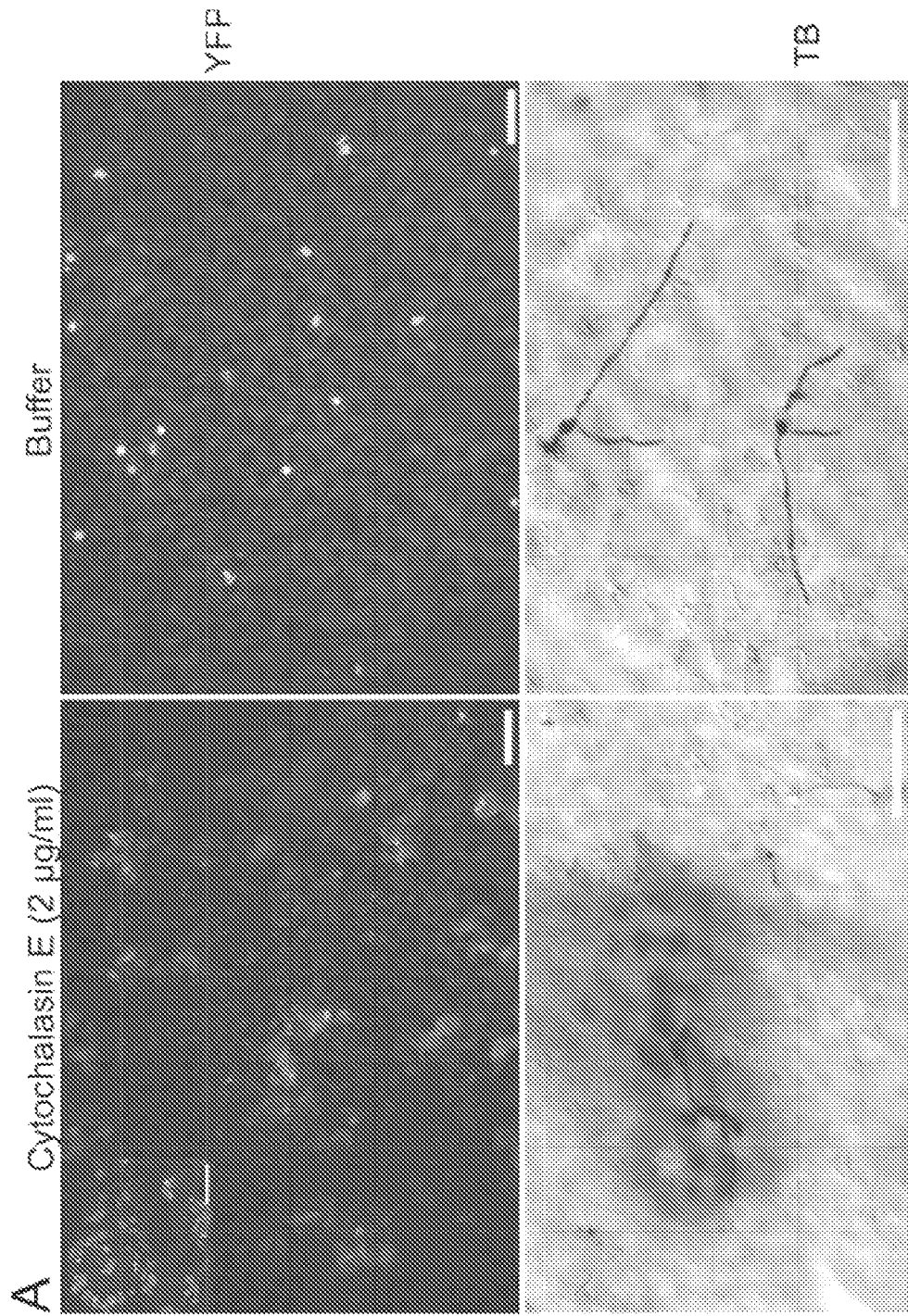

FIG. 13 shows that targeting of RPW8.2 to the EHM requires function of actin cytoskeleton.

(A) Cytochalasin E treatment impedes and enhances fungus-induced cell death. Detached leaves of plants expressing RPW8.2-YFP were evenly inoculated with Gc UCSC1 and at 12 dpi pressure-infiltrated with a solution containing cytochalasin E or oryzalin (not shown) or buffer. At 32-36 hpi, leaf sections were examined under a Zeiss epifluorescence microscope for RPW8.2-YFP localization (upper panel) and subsequently subject to trypan blue (TB) staining to visualize fungal structure and induced cell death (lower panel). Note the punctuate RPW8.2-YFP expression in the mesophyll cells (inset in the upper corner). Bars=50 μm.

(B) Representative T1 lines transgenic for the indicated constructs. Number-indicated plants were selected for RT-PCR in (C).

(C) Relative expression levels of the indicated genes determined by RT-PCR. UBC21 (At5g25760) was used as the endogenous control.

Figure 14:
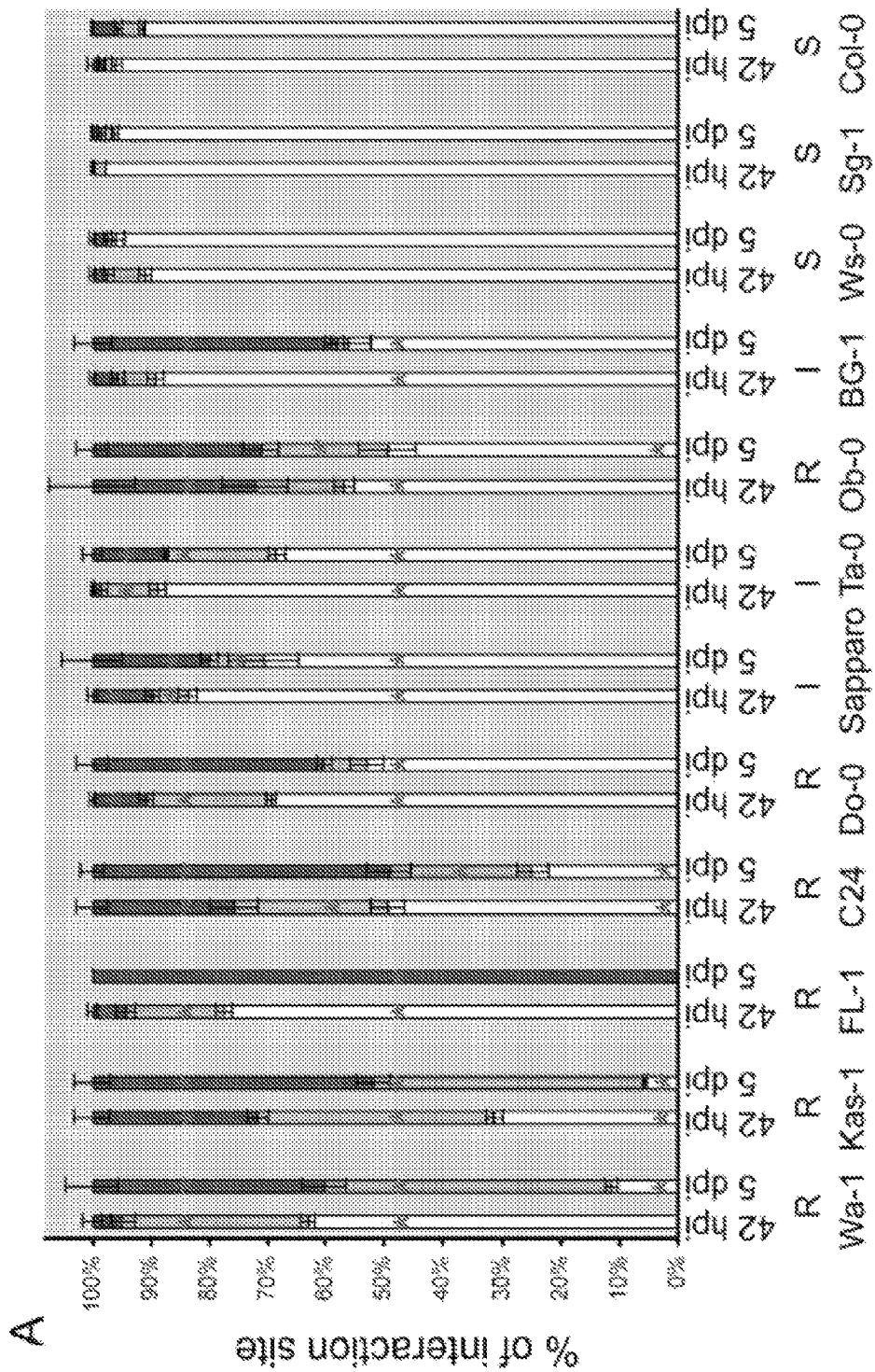

FIG. 14 shows that RPW8 enhances the formation of the callosic encasement of the haustorial complex (EHC) and $H_2O_2$ production.

(A) Types and frequencies of interactions seen in the haustorium-invaded epidermal cells in plants of 12 *Arabidopsis* accessions at 42 hpi and 5 dpi with *G. cichoracearum* UCSC1. The reaction phenotypes of the accessions were categorized into resistant (R), Intermediate (I) and susceptible (S) (Orgil et al., 2007). White, grey and dark bars indicate frequencies of cells containing a haustorium without an EHC, living cells containing a haustorium with an EHC and cells undergoing HR, respectively. Data are means±S.E.M., calculated from three duplicated experiments, in each of which 300-500 invaded cells were examined. Accessions that were significantly different from Col-0 (P<0.0 1; n=3, student's t-test) were indicated by an asterisk. Note that Kas-1 and Wa-1 contains identical RPW8.1 and RPW8.2 alleles as Ms-0, Seven resistant (R) or moderately resistant (I) accessions contain divergent RPW8.2 alleles that may be partially functional. Two susceptible accessions (Ws-0 and Sg-1) contain RPW8.2 alleles encoding RPW8.2 variants with a C-terminal 3 1 amino acid truncation.

(B) A leaf section of Wa-1 plants (grown under ~85 μmol·m2·s1; 8 hrs/day) inoculated with *G. cichoracearum* UCSC1 and stained with trypan blue to visualize the EHC (arrows) and fungal structures at 6 dpi. Note the E11C formation (arrows) in all the haustorium-invaded cells and restricted fungal growth. Bar=100 μm.

(C) Three patterns of 11202 accumulation in haustorium-invaded epidermal cells revealed by 3,3'-diaminobenzidine-trypan blue staining: 11202 (indicated by the reddish brown precipitate) is accumulated in the haustorial complex which is often accompanied with the E11C (left); 11202 is spread into the whole invaded epidermal cell (middle); or there is no detectable 11202 in the cell (right). Bar=20 μm.

Figure 15:
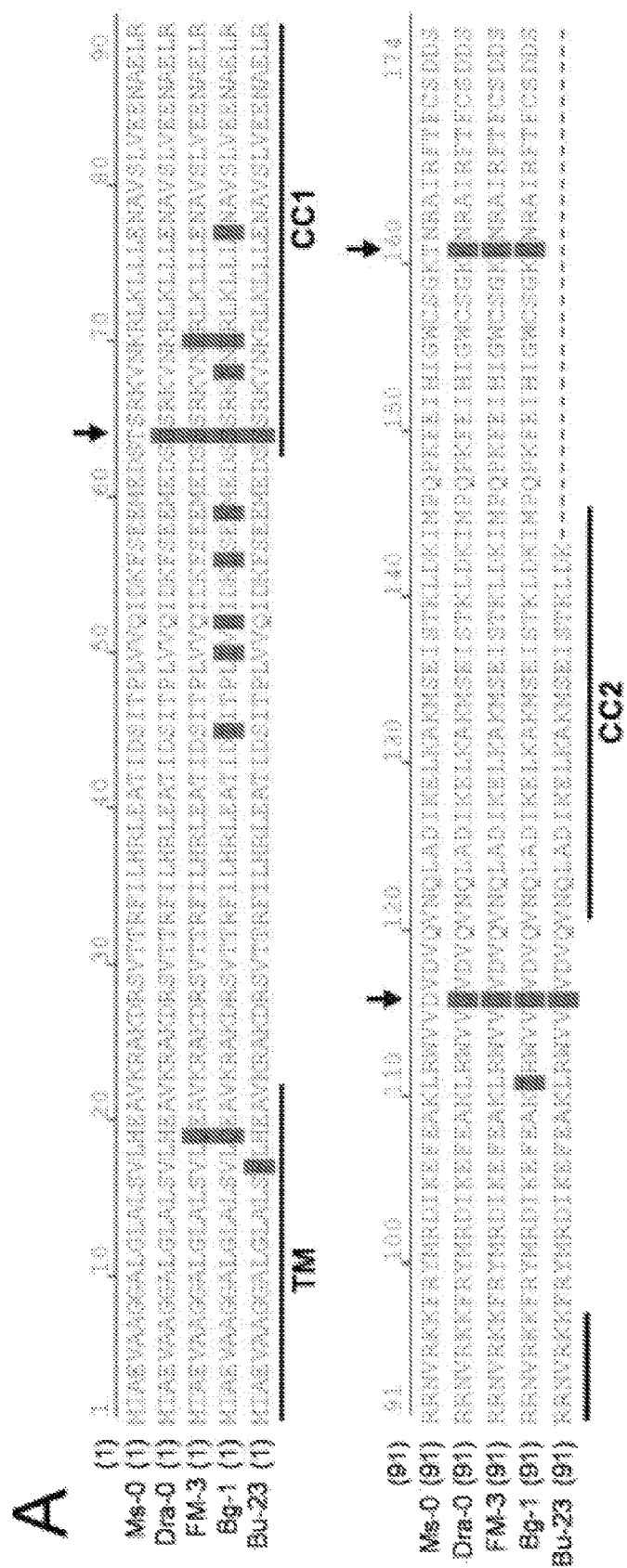
Figure 15:
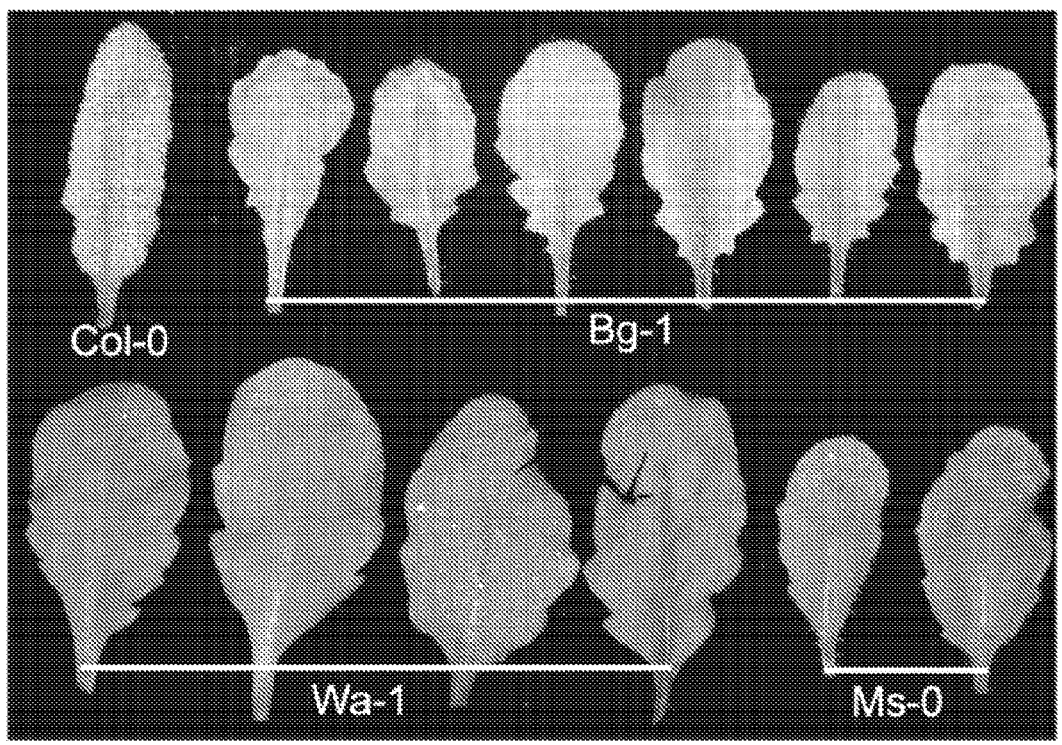

FIG. 15 A. Polymorphic sites among five indicated RPW8.2 alleles at the amino acid level. Amino acid substitutions relative to RPW8.2$^{Ms-0}$ are highlighted in red. Arrows indicate three common substitutions. The transmembrane domain (TM) and the two coiled-coil (CC) domains are underlined. Ms-0 (SEQ ID NO.: 1); Dra-0 (SEQ ID NO.: 2); FM-3 (SEQ ID NO.: 3); Bg-1 (SEQ ID NO.: 4); Bu-23 (SEQ ID NO.: 5) B. Bg-1 plants were moderately susceptible to Gc UCSC1 despite massive induced cell death. Representative leaves of plants from the indicated accessions were photographed at 10 dpi.

Figure 16:
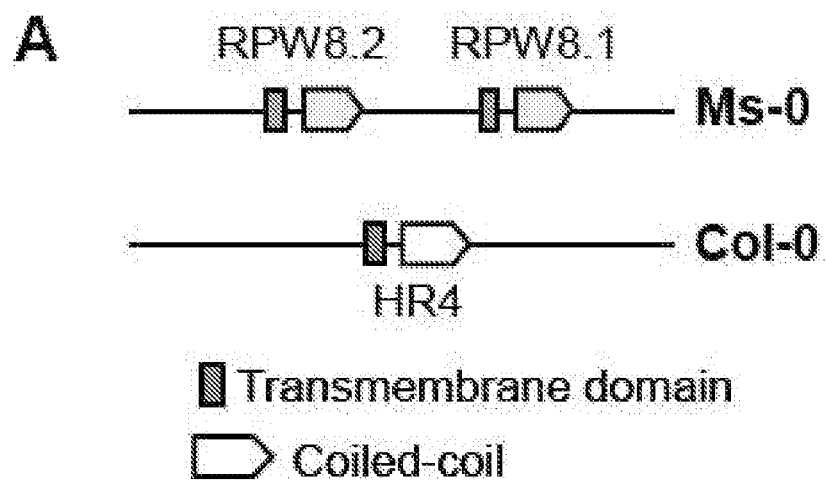
Figure 16:
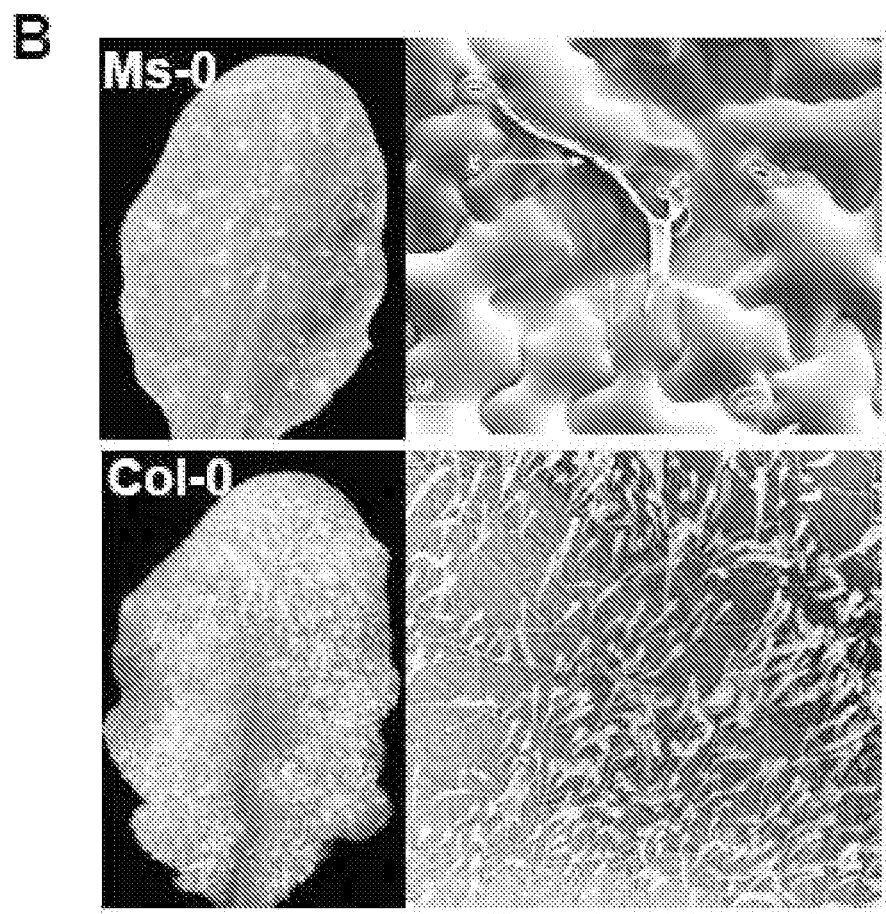

FIG. 16. A. The schematic gene organization of the complex RPW8 locus in Ms-0 (resistant) and Col-0 (susceptible) accessions. B. The disease reaction phenotypes of Ms-0 and Col-0 at 8 days after inoculation of *Erysiphe cichoracearum* UCSC1. Note the collapse of the penetrated host cell in Ms-0.

Figure 17:
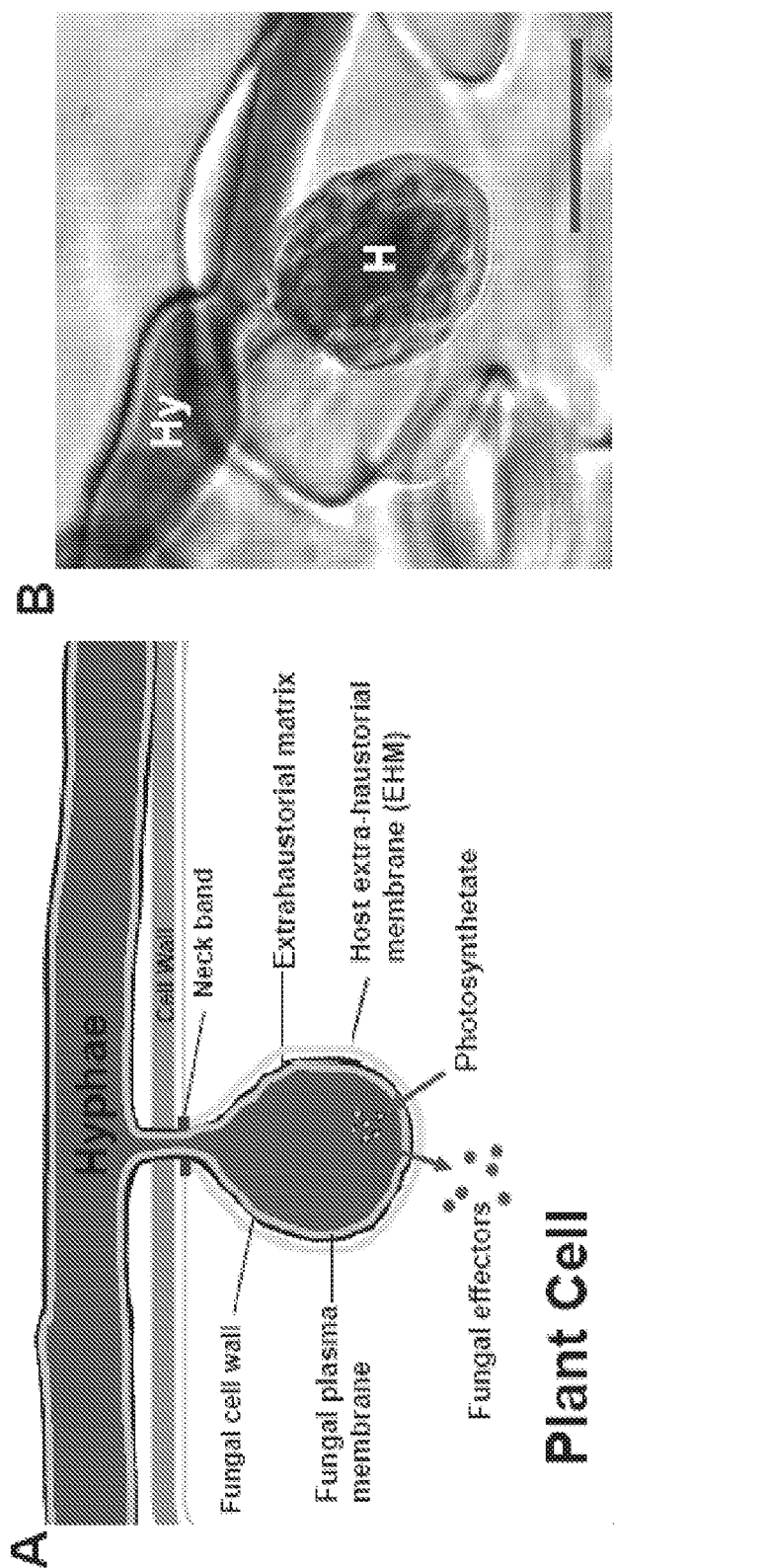

FIG. 17 A. A cartoon illustrating the structure of a fungal haustorium and the host-pathogen interface. B. A real-life haustorium detected inside a susceptible epidermal cell of Col-0. The fungal structure is stained blue by trypan blue staining H, haustorium; hy, hyphae. Bar=15 μm.

Figure 18:
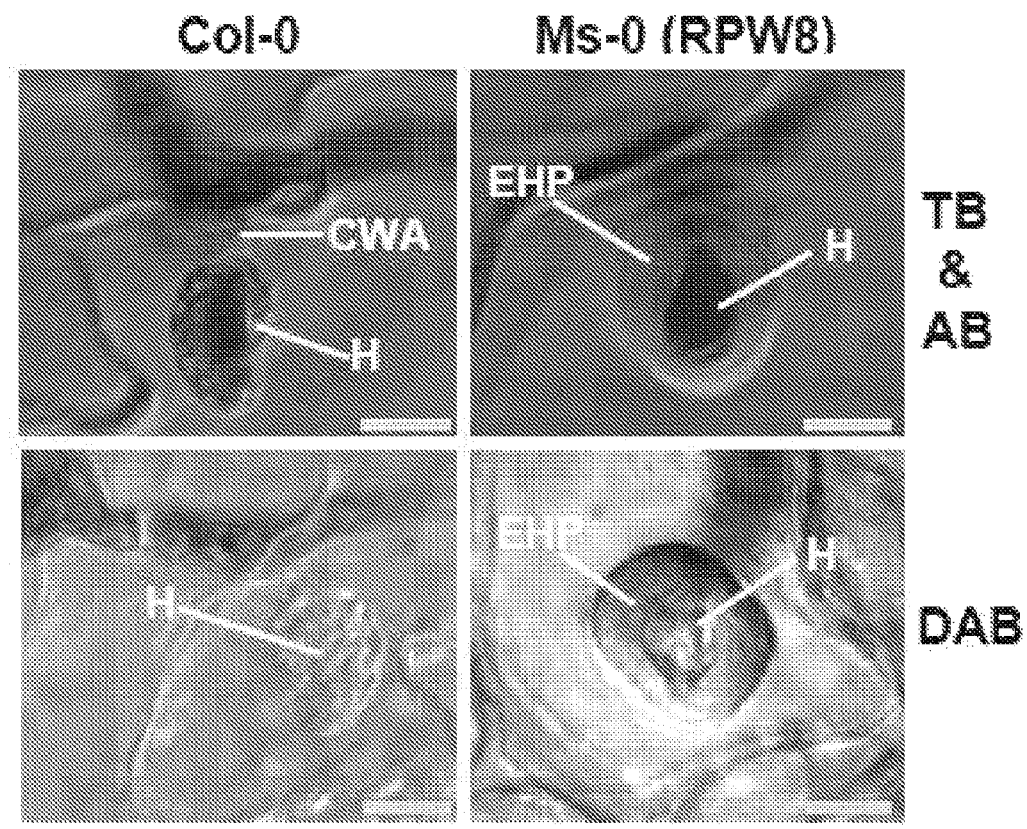

FIG. 18 shows a plant defense response in Col-0 and Ms-0 (RPW8-expressing) at the subcellular level. Plants were inoculated with *E. cichoracearum* UCSC1 and at 2 dpi inoculated leaves were subject to trypan blue staining (TB) to visualize the fungal structure (dark blue), anilline blue staining (AB) to visualize callose deposition (bright blue) or 3,3'-diaminobenzidine (DAB) staining to detect $H_2O_2$ (brownish) in or around the fungal haustorium. H, haustorium; CWA, cell wall apposition; EHP, extrahaustorial papillae. Bar=10 μm.

Figure 19:
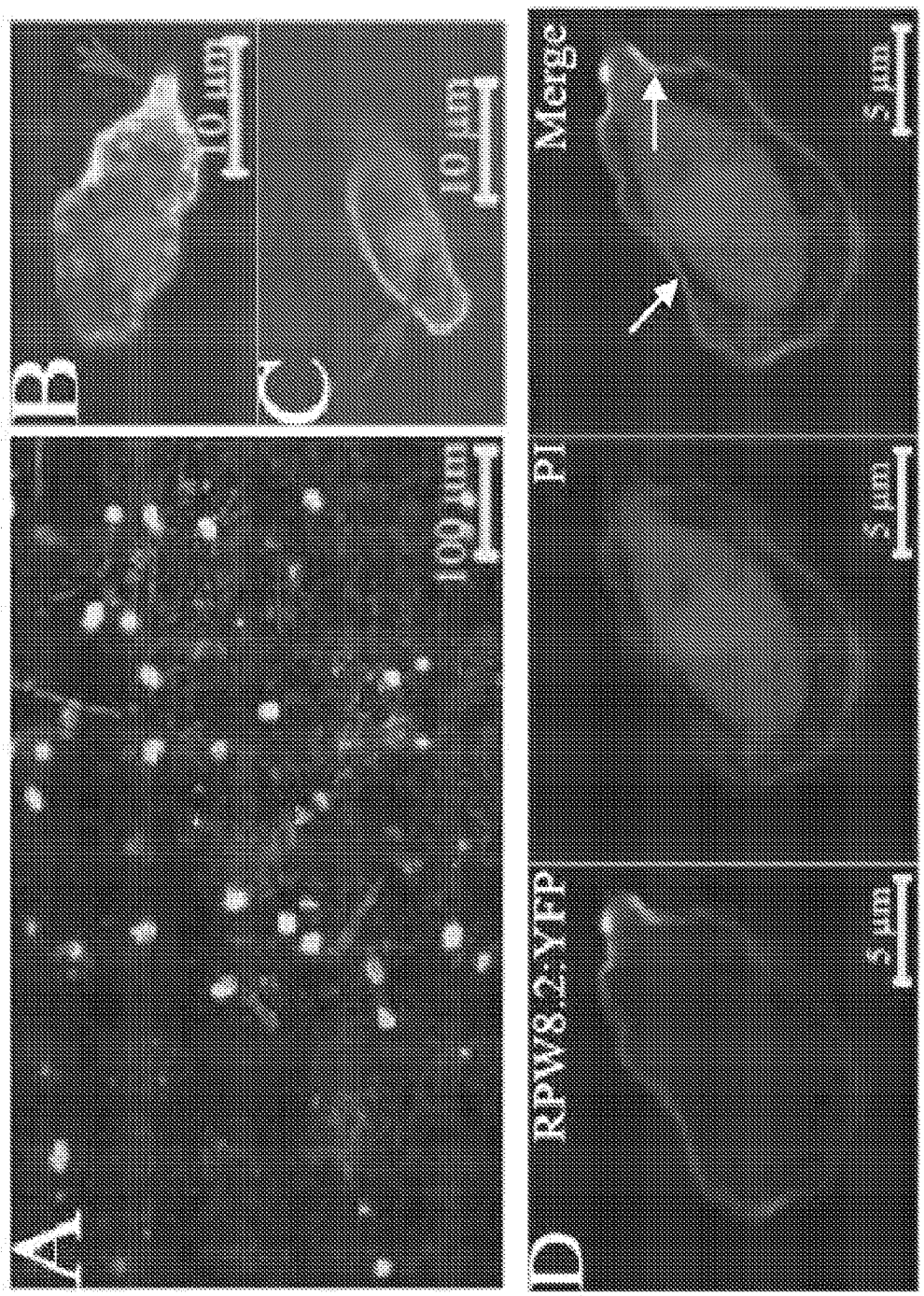
Figure 19:
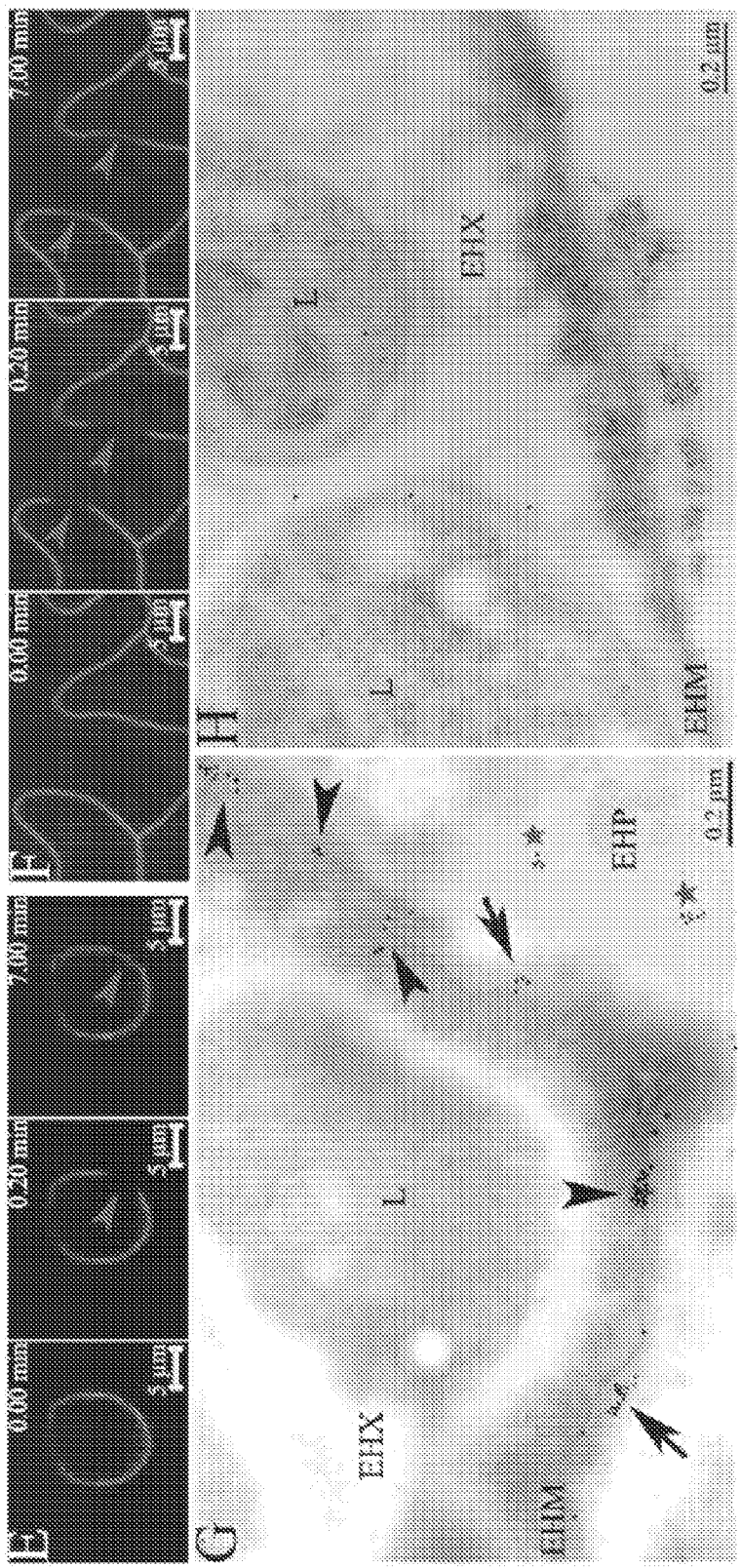

FIG. 19 shows the EHM-localization of RPW8.2. A. Haustoria encased by RPW8.2:YFP at 5 days post inoculation (dpi). B. Z-stack projection to show single haustorium encased by RPW8.2:YFP. Note the strong signal at the haustorial neck (arrow). C. One section of a haustorium encased by RPW8.2:YFP to show vacuole (arrow) and fragment of the nucleus in the haustorium. D. An isolated haustorium to show RPW8.2:YFP was colocalized with the PI-stained EHM (arrows). E&F. RPW8.2:YFP fluorescence was able to recover from photobleaching (arrowheads) in 7 minutes (E), which is similar to the plasma membrane protein marker GFP:SIMIP (F). G. Transmission electronic microscopy showed that immunogold-labeled RPW8.2:YFP was either integrated into the EHM (arrowheads) or attached to the EHM (arrows) or yet to arrive at the EHM (stars). H. Negative control from plant lack RPW8.2:YFP. PI, propidium iodide. EHX, extrahaustorial matrix. EHM, extrahaustorial membrane. EHP, extrahaustorial papillae.

Figure 20:
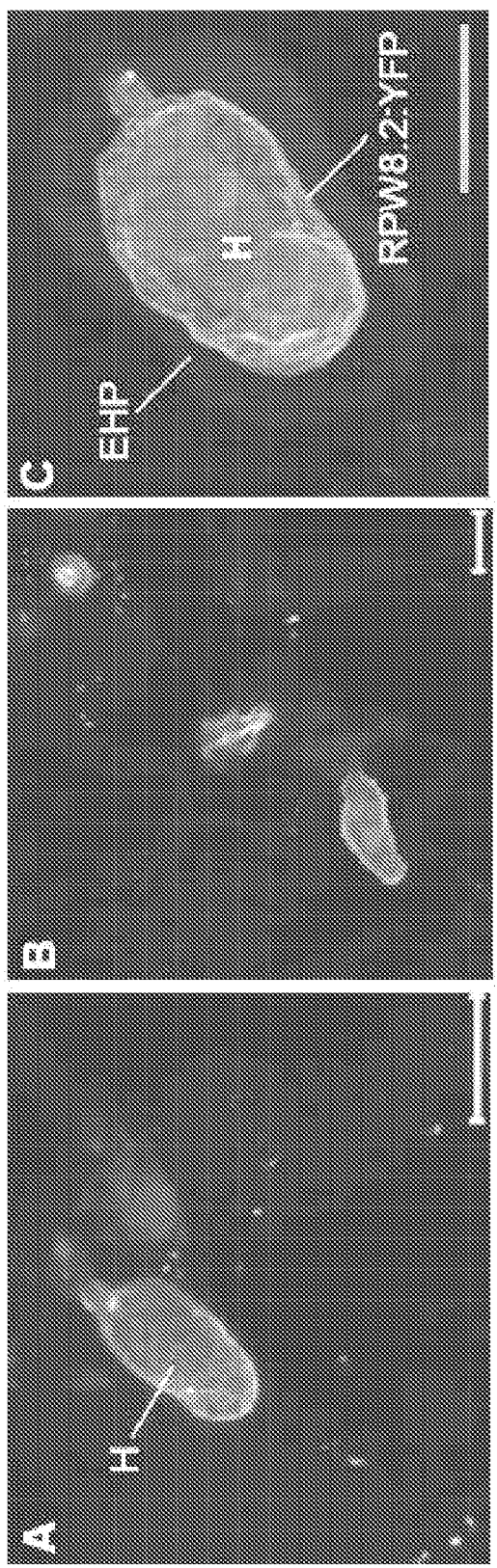

FIG. 20 shows results of leaves of NP::RPW8.2-YFP plants that were inoculated with powdery mildew and then infected leaves were stained with propidium iodide to highlight the fungal structures and visualized using a confocal microscope. Pictures shown are Z-projection of 20 images taken at 26 hpi. H, haustorium. A. Small RPW8.2:YFP containing vesicles moving and fusing into the EHM encasing the haustorium. B. RPW8.2 targeted haustoria become aborted (yellow arrows) or shrunk (white arrow). Bar=10 μm. C. An isolated haustorium showing weakly stained extrahaustorial papillae (EHP) surrounding the RPW8.2-YFP labeled haustorium.

FIG. 21 shows a summary of deletion and transgenic analyses of RPW8.2 for identification of the EHM-targeting signal. TM, transmembrane; CC1, coiled-coil 1; CC2, Coiled-coil 2; LTI6b, a small plasma membrane protein (At3g05890); YFP, yellow fluorescent protein. Numbers followed by Δ indicates deleted amino acids. * Indicates two defining constructs. Blue-shaded indicated the 22 amino acids (VRKKFRYM-RDIKEFEAKLRWVV) (SEQ ID NO: 6) essential for EHM-targeting of RPW8.2.

Figure 22:
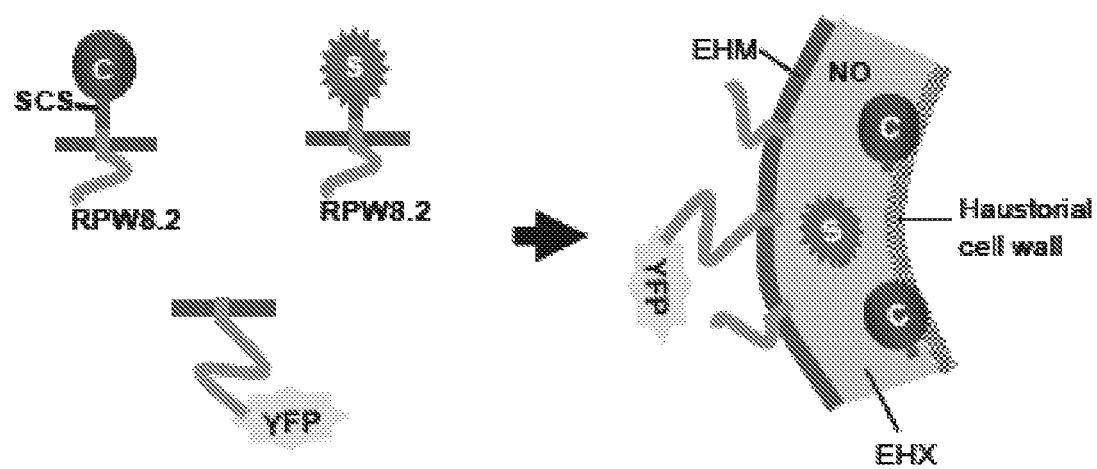

FIG. 22 shows a schematic illustration of the strategy for specific targeting of antifungal cargo (C) (for example, chitinases) across the extrahaustorial membrane (EHM) and subsequent controlled release of the cargo in the extrahaustorial matrix (EHX). S, subtilisin; SCS, subtilisin cleavage site; NO, nitric oxide.

DETAILED DESCRIPTION OF THE INVENTION

Powdery mildew fungal pathogens penetrate the plant cell wall and develop a feeding structure named the haustorium to steal photosynthetate from the host cell. The present invention shows that the broad-spectrum mildew resistance protein RPW8.2 from *Arabidopsis thaliana* is induced and specifically targeted to the extra-haustorial membrane (EHM) which is an enigmatic interfacial membrane believed to be derived from the host cell plasma membrane. There, RWP8.2 activates a salicylic acid (SA) signaling-dependent defense strategy that concomitantly enhances the encasement of the haustorial complex (EHC) and onsite accumulation of $H_2O_2$ to constrain the haustorium while reducing oxidative damage to the host cell. Notably, targeting of RPW8.2 to the EHM is SA-independent but does require function of actin cytoskeleton. Thus, the interception of haustoria pinpoints the nature of RPW8-mediated broad-spectrum mildew resistance.

DEFINITIONS

While the following terms are believed to have well defined meanings in the art, the following definitions are set forth to facilitate explanation of the invention.

Following long-standing patent law convention, the terms "a" and "an" mean "one or more" when used in this application, including the claims.

The term "promoter," as used herein refers to a region of DNA upstream from the structural gene and involved in recognition and binding RNA polymerase and other proteins to initiate transcription. A "plant promoter" is a promoter capable of initiating transcription in plant cells. An "inducible" promoter is a promoter which is under more precise environmental or developmental control. Examples of environmental conditions that may effect transcription by inducible promoters include anaerobic conditions or the presence of light. Examples of promoters under developmental control include promoters that initiate transcription only in certain tissues, such as root specific promoters.

The term "plant," as used herein, includes whole plants, plant organs (e.g., leaves, stems, roots, etc.), seeds and plant cells. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid.

The term "expression," as used herein, refers to the transcription and translation of a structural gene so that a protein is synthesized.

The term "operably linked," as used herein, refers to functional linkage between a promoter and a second sequence, wherein the promoter sequence initiates transcription of RNA corresponding to the second sequence.

The term "modulate," as used herein, means an increase, decrease, or other alteration of any or all chemical and biological activities or properties of a wild-type or mutant gene or protein. The term "modulation" as used herein refers to both upregulation (i.e., activation or stimulation) and downregulation (i.e. inhibition or suppression) of a response.

The terms "cells," "host cells" or "recombinant host cells," as used herein, are used interchangeably and mean not only to the particular subject cell, but also to the progeny or potential progeny of such a cell. Because certain modifications can occur in succeeding generations due to either mutation or environmental influences, such progeny might not, in fact, be identical to the parent cell, but are still included within the scope of the term as used herein.

The term "interact," as used herein, means detectable interactions between molecules. The term "interact" is also meant to include "binding" interactions between molecules. Interactions can, for example, be protein-protein, protein-nucleic acid or nucleic acid-nucleic acid in nature.

The term "modified," as used herein, means an alteration in a nucleotide or amino acid sequence which includes adding or removing discrete amino acid residues or nucleotide units. The term "modified" encompasses detectable labels as well as those entities added as aids in purification.

The term "mutation," as used herein, carries its traditional connotation and means a change, inherited, naturally occurring or introduced, in a nucleic acid or polypeptide sequence, and is used in its sense as generally known to those of skill in the art.

The term "polypeptide," as used herein, refers to peptides, polypeptides and proteins, unless otherwise noted. As used herein, the terms "protein," "polypeptide" and "peptide" are used interchangeably herein when referring to a gene product.

The term "polynucleotide," as used herein, means a sequence of nucleotides connected by phosphodiester linkages. A polynucleotide of the present invention can be a deoxyribonucleic acid (DNA) molecule or ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (I) and uracil (U). A polynucleotide of the present invention can be prepared using standard techniques well known to one of skill in the art.

The term "complementary sequence," as used herein, indicates two nucleotide sequences that comprise antiparallel nucleotide sequences capable of pairing with one another upon formation of hydrogen bonds between base pairs. As used herein, the term "complementary sequences" means nucleotide sequences which are substantially complementary, as can be assessed by the same nucleotide comparison set forth above, or is defined as being capable of hybridizing to the nucleic acid segment in question under relatively stringent conditions such as those described herein. A particular example of a complementary nucleic acid segment is an antisense oligonucleotide.

The term "gene," as used herein, refers broadly to any segment of DNA associated with a biological function. A gene encompasses sequences including but not limited to a coding sequence, a promoter region, a cis-regulatory sequence, a non-expressed DNA segment is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

The term "gene expression," as used herein, refers to the process of converting genetic information encoded in a gene into RNA (e.g., mRNA, rRNA, tRNA, or snRNA) through "transcription" of a deoxyribonucleic gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (ie., RNA or protein), while "down-regulation" or "repression" refers to regulation that decrease production. Molecules (e.g., transcription factors) that are involved in up-regulation or down-regulation are often called "activators" and "repressors," respectively.

The term "substantial identity," as used herein means that a polynucleotide or polypeptide comprises a sequence that has at least 80% sequence identity, preferably at least 90% or more preferably at least 97%, compared to a reference sequence over a comparison window.

The term "antipathogenic proteins" as used herein means proteins have antipathogenic activity and thus are capable of suppressing, controlling, and/or killing the invading pathogenic organism. An antipathogenic protein of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens. In particular embodiments, the antipathogenic activity exhibited by the proteins of the invention is antifungal activity. As used herein, "antifungal activity" refers to the ability to suppress, control, and/or kill the invading fungal pathogen. Likewise, "fungal resistance" refers to enhanced tolerance to a fungal pathogen when compared to that of an untreated or wild type plant. Resistance may vary from a slight increase in tolerance to the effects of the fungal pathogen (e.g., partial inhibition) to total resistance such that the plant is unaffected by the presence of the fungal pathogen.

General Methods

Generally, the nomenclature used hereafter and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., 1989.

The present invention relates to a method for increasing expression of a nucleotide sequence encoding for the RPW8 protein and/or using expression of the RPW8 protein as a delivery device for moving a toxic protein to the extrahaustorial membrane EHM. The nucleotide sequence comprises SEQ ID NO. 1 or a nucleotide sequence having at least 75% identity thereto, more preferably, at least 90% identity.

The methods of the invention involve introducing a polypeptide or polynucleotide into a plant. "Introducing" is intended to mean presenting to the plant the polynucleotide. In some embodiments, the polynucleotide will be presented in such a manner that the sequence gains access to the interior of a cell of the plant, including its potential insertion into the genome of a plant. The methods of the invention do not depend on a particular method for introducing a sequence into a plant, only that the polynucleotide gains access to the interior of at least one cell of the plant. Methods for introducing polynucleotides into plants are known in the art including, but not limited to, stable transformation methods, transient transformation methods, and virus-mediated methods.

The term "Stable transformation" as used herein means that the nucleotide construct introduced into a plant integrates into the genome of the plant and is capable of being inherited by the progeny thereof "Transient transformation" or "transient expression" is intended to mean that a polynucleotide is introduced into the plant and does not integrate into the genome of the plant or a polypeptide is introduced into a plant.

In specific embodiments, the sequences of the invention can be provided to a plant using a variety of transient transformation methods. Such transient transformation methods include, but are not limited to, the introduction of the protein or variants and fragments thereof directly into the plant or the introduction of the protein transcript into the plant. Such methods include, for example, microinjection or particle bombardment. Alternatively, the polynucleotide can be transiently transformed into the plant using techniques known in the art. Such techniques include viral vector system and the precipitation of the polynucleotide in a manner that precludes subsequent release of the DNA.

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that the an antipathogenic polypeptide of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases.

The nucleic acids are preferably oligonucleotides and may consist entirely of deoxyribo-nucleotides, modified deoxyribonucleotides, or some combination of both. The antisense nucleic acids can be synthetic oligonucleotides. The oligonucleotides may be chemically modified, if desired, to improve stability and/or selectivity. Since oligonucleotides are susceptible to degradation by intracellular nucleases, the modifications can include, for example, the use of a sulfur group to replace the free oxygen of the phosphodiester bond. This modification is called a phosphorothioate linkage. Phosphorothioate oligonucleotides are water soluble, polyanionic, and resistant to endogenous nucleases.

The present invention also relates to compositions, and methods using said compositions, comprising a DNA expression vector capable of expressing a nucleotide sequence capable of overexpression of RPW8 protein and/or expression of the RPW8 protein in combination with a protein that will inhibit pathogen growth at the EHM.

The nucleic acid sequence expressing the RPW8 nucleotide sequence is preferably included within a vector. Selection of an appropriate vector useful in the present invention is relatively simple, as the constraints are minimal. The minimal requirements of the vector are that the desired nucleic acid sequence be introduced in a relatively intact state. Thus, any vector which will produce a plant carrying the introduced nucleotide sequence should be sufficient. Any vector which will introduce a substantially intact RNA which can ultimately be converted into a stably maintained nucleotide sequence is also acceptable. The decision as to whether to use a vector, or which vector to use, will be guided by the method of transformation selected. This determination is considered to be well with in the ordinary skill of those in the art.

The vectors useful in the present invention include, but are not limited to, the Ti plasmid vectors and shuttle vectors designed for particle gun transformation. The selection of vectors and methods to construct them are commonly known to persons of ordinary skill in the art and are described in general technical references. The vectors typically comprise additional attached sequences which confer resistance to degradation of the nucleic acid fragment, which assist in the process of genomic integration, or which provide a means to easily select for those cells or plants which are transformed. Such sequences are advantageous and greatly decrease the difficulty of selecting useable transformed plants.

The recombinant vectors of the present invention typically comprise an expression cassette designed for initiating transcription of the desired polynucleotide sequences in plants. Other nucleotide sequences encoding additional functions may also be present in the vector, as is known in the art. For instance, in the case of *Agrobacterium* transformations, T-DNA sequences will also be included for subsequent transfer to plant chromosomes. For expression in plants, the recombinant expression cassette will contain, in addition to the desired polynucleotide sequence, a plant promoter region, a transcription initiation site (if the sequence to be transcribed lacks one), and a transcription termination sequence. Unique restriction enzyme sites at the 5' and 3' ends of the cassette are typically included to allow for easy insertion into a pre-existing vector.

The particular promoter used in the expression cassette can be varied depending on the application. Any of a number of promoters which direct transcription in plant cells is suitable. The promoter can be either constitutive or inducible. Promoters of bacterial origin include the octopine synthase promoter, the nopaline synthase promoter and other promoters derived from native Ti plasmids. Viral promoters include the 35S and 19S RNA promoters of cauliflower mosaic virus. Possible plant promoters include the ribulose-1,3-bisphosphate carboxylase small subunit promoter and the phaseolin promoter.

A promoter which is expressed concurrently with or prior to the normal activation of the homologous endogenous sequence is generally preferred. A constitutive promoter is most preferred, such as the cauliflower mosaic virus promoter. This promoter is constitutive because its operation is relatively independent of the developmental stage of the cell in which it is contained.

A regulated or inducible promoter, such as ones associated with the ribulose-1,5-bisphosphate carboxylase, the chlorophyll binding proteins or the glycine-rich root protein genes are also suitable. Control may be either temporal with respect to the developmental stage of the cell, or spatial with respect to different parts or organs of the plant. The operation of a promoter may also vary depending on its location in the genome. Thus, an inducible promoter may become fully or partially constitutive in certain locations. Promoters particularly useful in the present invention include tuber specific promoters such as the promoter for the gene encoding the tuber protein patatin.

In addition to a promoter sequence, the expression cassette may include a transcription termination region downstream of the structural gene to provide for efficient termination. The termination region may be obtained from the same gene as the promoter sequence or may be obtained from different genes.

The vector may also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow in a medium containing the particular antibiotic.

The vectors described above can be microinjected directly into plant cells by use of micropipettes to mechanically transfer the recombinant DNA. The genetic material may also be transferred into the plant cell using polyethylene glycol. Another method of introduction of polynucleotide sequences is particle acceleration of small particles with the nucleic acid either within the matrix of small beads or particles, or on the surface. Yet another method of introduction is fusion of protoplasts with other entities, such as, minicells, cells, lysosomes or other fusible lipid-surfaced bodies. The DNA may also be introduced into the plant cells by electroporation. In this technique, plant protoplasts are electroporated in the presence of plasmids containing the expression cassette. Electrical impulses of high field strength reversibly permeabilize biomembranes allowing the introduction of the plasmids.

Cauliflower mosaic virus (CaMV) may be used as a vector for introducing the DNA into plant cells. (U.S. Pat. No. 4,407, 956). In accordance with the described method, the entire CaMV vial DNA genome is inserted into a parent bacterial plasmid creating a recombinant DNA molecule which can be propagated in bacteria. After cloning, the recombinant plasmid is further modified by introduction of the desired sequence into unique restriction sites in the viral portion of the plasmid. The modified viral portion of the recombinant plasmid is then excised from the parent bacterial plasmid, and used to inoculate the plant cells or plants.

A preferred method of introducing the DNA into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. Preferred *Agrobacterium* strains useful in the present invention include LBA 4404, C58C1, EHA 101, W2/73, R1601, LBA 288, GV 3850, A281, GV311 SE, A856, A136, GC3101, 1S955, and bo 42.

*Agrobacterium* is a genus in the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by *Agrobacterium* and is stably integrated into the plant genome.

Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid, such vectors are typically termed binary vectors. The transferred DNA region, can be increased in size by the insertion of heterologous DNA without its ability to be transferred being affected. A modified Ti or Ri plasmid, in which the disease-causing genes have been deleted, can be used as a vector for the transfer of the gene constructs of this invention into an appropriate plant cell.

Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences.

All plant cells which can be transformed by *Agrobacterium* and from which whole plants can be regenerated can be transformed according to the present invention to produce transformed intact plants which contain the desired DNA. There are two common ways to transform plant cells with *Agrobacterium*:

(A) co-cultivation of *Agrobacterium* with cultured isolated protoplasts, or
(B) transformation of intact cells or tissues with *Agrobacterium*.

Most dicot species can be transformed by *Agrobacterium*. All species which are a natural plant host for *Agrobacterium* are transformable in vitro.

After transformation, transformed plant cells or plants comprising the introduced DNA must be identified. A selectable marker, such as those discussed, supra, is typically used. Transformed plant cells can be selected by growing the cells on growth medium containing the appropriate antibiotic. The presence of opines can also be used if the plants are transformed with *Agrobacterium*.

After selecting the transformed cells, one can confirm expression or lack of expression of the relevant gene. Simple detection of the levels of mRNA can be achieved by well known methods in the art, such as Northern blot hybridization.

After determination that the inserted nucleotide sequence has affected the plant cell, whole plant regeneration may be desired. All plants from which protoplasts can be isolated and cultured to give whole regenerated plants can be hosts for the polynucleotide sequences of the present invention. Some suitable plants may include, but is not limited to, *Arabidopsis, Brassica, Raphanus, Sinapis, Atropa, Capsicum, Hyoscyamus, Lycopersicon, Nicotiana, Solanum, Oryza, Petunia, Digitalis, Majorana, Cichorium, Helianthus, Lactuca, Bromus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, Malus, Apium, Phaseolus, Pisum, Hordeum, Beta* and *Datura*.

Means for plant regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins Efficient regeneration will depend on the medium, on the genotype, and on the history of the culture. If these three variables are controlled, then regeneration is usually reproducible and repeatable. Regenerated plants with the desired characteristics are typically identified by determining activity of the target gene or expressed protein.

Finally, one of skill will recognize that after the expression cassette is stably incorporated in transgenic plants and confirmed to be operable, it can be introduced into other plants by sexual crossing. Any of a number of standard breeding techniques can be used, depending upon the species to be crossed.

Methods

Plant Lines, Growth Conditions and Transformation

*Arabidopsis* accession Col-0 was used for generation of transgenic lines expressing RPW8.2-YFP fusion construct from the native promoter (Np). Accession Ms-0 containing RPW8.1 and RPW8.2 (together referred to as RPW8 unless otherwise indicated) and/or Col-0 transgenic line S5 carrying a single copy of RPW8 under control of the native promoters (Xiao et al., 2003) was used as a resistance reference in the pathogen tests. The following transgenic or mutant lines were used for Np::RPW8.2-YFP transgenic studies and/or genetic crossings with S5: eds1-2, pad4-1, NahG, pen1-1 and pmr4-1. Except eds1-2, which is from accession Ler, all other lines have a Col-0 genetic background.

Unless otherwise indicated, seeds were sown in Sunshine Mix #1 (Maryland Plant & Suppliers, Inc., USA) and cold-treated (4° C. for 2 days), and seedlings were kept under 22° C., 75% RH, short-day (8 hrs light at ~125 μmol·m-2·sec-1, 16 hrs dark) conditions for 5-6 weeks before pathogen inoculation or other treatments.

DNA Constructs and Transcript Analysis

Plasmids for Np::RPW8.1-YFP and Np::RPW8.2-YFP were made in a previous report (Wang et al., 2007). Alleles of RPW8.2 from Dra-0, Fm-3, Bu-23 and Bg-1 were amplified with the same primers for the Ms-0 allele and C-terminally in-frame fused with YFP. The chimeric genes were placed downstream of the RPW8.2Ms-0 promoter in the pPZPR823' binary vector (Wang et al., 2007). For overexpression of ADF5 (At2g16700) and ADF6 (At2g3 1200), the genomic sequence of the two genes and their 3'UTR regions were PCR amplified and cloned into pEarleyGate 100 under control of the 35S promoter (Earley et al., 2006). All the DNA constructs were introduced into *Arabidopsis* Col-0, R2Y4 (Col-0 line transgenic for Np::RPW8.2-YFP) or various mutant lines via *Agrobacterium*-mediated transformation using the *A. tumefaciens* strain GV3101. For measuring transcript levels, total RNA was isolated from leaves or seedlings with TRIzol Reagent (Invitrogen). First strand cDNA was synthesized from 2 μg of total RNA with reverse transcriptase. Relative mRNA levels were determined by semi-quantitative PCR using cDNA-specific primers. UBC21 (At5g25760) was used as the endogenous control. Primers are set forth below in Table 1

| Gene ID | Primer ID | Primer Sequence 5'→3' | |
|---|---|---|---|
| At2g16700 | ADF5cF | GGCTTTCAAGATGGCGACGA | SEQ ID NO.: 10 |
| | ADF5cR | CTATTTGGCACGGTCTTGGATAA | SEQ ID NO.: 11 |
| At2g31200 | ADF6cF | GACTTAGCAGGCCAAATGCAA | SEQ ID NO.: 12 |
| | ADFC6cR | CTTGCTCTCAGTTCGCTCGTT | SEQ ID NO.: 13 |
| At5g25760 | UBC21F | GGCATCAAGAGCGCGACTGT | SEQ ID NO.: 14 |
| | UBC21R | GCGGCGAGGCGTGTATACAT | SEQ ID NO.: 15 |

Pathogen Infection and Microscopic Analyses

The powdery mildew isolate *Golovinomyces cichoracearum* (Gc) UCSC1 was maintained on live eds1-2 or pad4-1 plants for generation of fresh inoculums. Inoculation and visual scoring of disease reaction phenotypes were done as previously described (Xiao et al., 2005). Fugal structures and dead cells in inoculated leaves were visualized with trypan blue staining (Xiao et al., 2003) at 42 hpi or 5 dpi. Interaction sites were counted and classified into three categories: (a) Viable cells with a deformed or shrunken haustorium encased by a callose-containing layer known as the encasement of the haustorial complex (EHC) (Jacobs et al., 2003); (b) Cells undergoing haustorium-induced HR; (c) Viable cells with a healthy haustorium without the EHC. At least 300 interaction sites per genotype were scored at 42 hpi and 5 dpi in each of the three duplicate experiments. Student's t-test was performed to test statistical significance. In situ detection of callose was done by aniline blue (0.0 1% in an aqueous solution containing 150 mM KH2PO4, pH 9.5) staining In situ detection of $H_2O_2$ was performed as previously described (Xiao et al., 2003). Single- or multiple channel-epifluorescent images were acquired with a Zeiss Axio microscope coupled with an HBO 100 microscope illumination system.

Intact haustorial complexes (HCs) were isolated according to a published protocol (Gil and Gay, 1977) from Gc UCSC1-infected Col-0 and Np:RPW8.2-YFP transgenic plants at 2 dpi. HCs were stained with 0.5% propidium iodide solution and visualized by Laser Scanning Confocal Microscopy (LSCM). LSCM images were acquired as previously described (Wang et al., 2007). All pictures presented in the figures are projections from Z-stacks of 15-40 images unless otherwise indicated.

The image data were processed using Zeiss LSM Image Browser or LSM5 Image Examiner (Thornwood, N.Y., U.S.A.) and Adobe Photoshop (Mountain View, Calif., U.S.A.).

Electron Microscopy and Immunogold Labeling

Plants of *Arabidopsis* Col-0 and Col-0 transgenic for Np:RPW8.2-YFP (line R2Y4) were heavily inoculated with Gc UCSC1. Leaves were sampled at 5 dpi and cut into 2×3 mm sections, fixed in fixative containing 3% paraformaldehyde and 1.25% gluteraldehyde in 0.1 M phosphate buffer (PB), pH 7.0, for overnight at 4° C. The fixed tissues were rinsed three times in 0.1 M PB for 15 minutes. After dehydration in a gradient of ethanol, the tissues were sequentially infiltrated with 2:1, 1:1, and 1:2 mixture of ethanol:LR White overnight at 4° C. Then the samples were transferred in three changes of pure LR White for 1 hour each at room temperature and kept in the last change of LR White overnight or stored at 4° C.

The samples were embedded in a flat embedding mold and cured in 60° C. oven for 24 hours. Ultrathin sections were put on Formvar-carbon coated 200 mesh nickel grids. The grids were incubated in 1% of $H_2O_2$ for 10 minutes to retrieve the antigen, washed twice in distilled water. Then the grids were incubated for 15 minutes in 0.05 M glycine prepared with 0.1 M PBST buffer (10 mM phosphate buffer, 150 mM NaCl, pH 7.4, 1% BAS, 0.15% Tween 20) to inactivate the residual aldehyde groups present after aldehyde fixation. Nonspecific binding sites were blocked for 30 minutes with 5% goat serum in PBST buffer. Immunogold labeling was performed by using rabbit anti-GFP serum (1:200; ab290, Abcam) overnight at 4° C. and goat anti-rabbit coupled to 10 nm gold particles (1:50; EMS, cat#25019) at 4° C. overnight. After contrast staining with 2.5% uranyl acetate for 5 minutes, samples were examined and images were acquired with a Zeiss EM10 transmission electron microscope (TEM). Plate films were used to record the TEM images which were then scanned to convert into digital images.

Pharmacological Treatments

Fully expanded leaves of 7 week-old RPW8.2-YFP plants were detached from the base of the petioles and inserted into Murashige & Skoog (MS) agar medium in petri dishes. The detached leaves were then evenly inoculated with Gc UCSC1 using a settling tower. At ~12 hpi, each leaf was pressure-infiltrated with a syringae lacking a needle a solution containing 0, 1, 2, 4, or 8 μg/ml of cytochalasin E (Sigma-Aldrich), or 0, 60, 120, 180 μg/ml oryzalin (Sigma-Aldrich) in one half and buffer (0.1-0.8% DMSO) in the other half from the bottom of the abaxial side. At 32-3 6 hpi, leaf sections (~0.5×0.5 cm) were examined under a Zeiss Axio epifluorescence microscope for counting the number of haustoria labeled by RPW8.2-YFP and subsequently subject to trypan blue staining to visualize and estimate the total number of haustoria and induced cell death.

Figure 1:
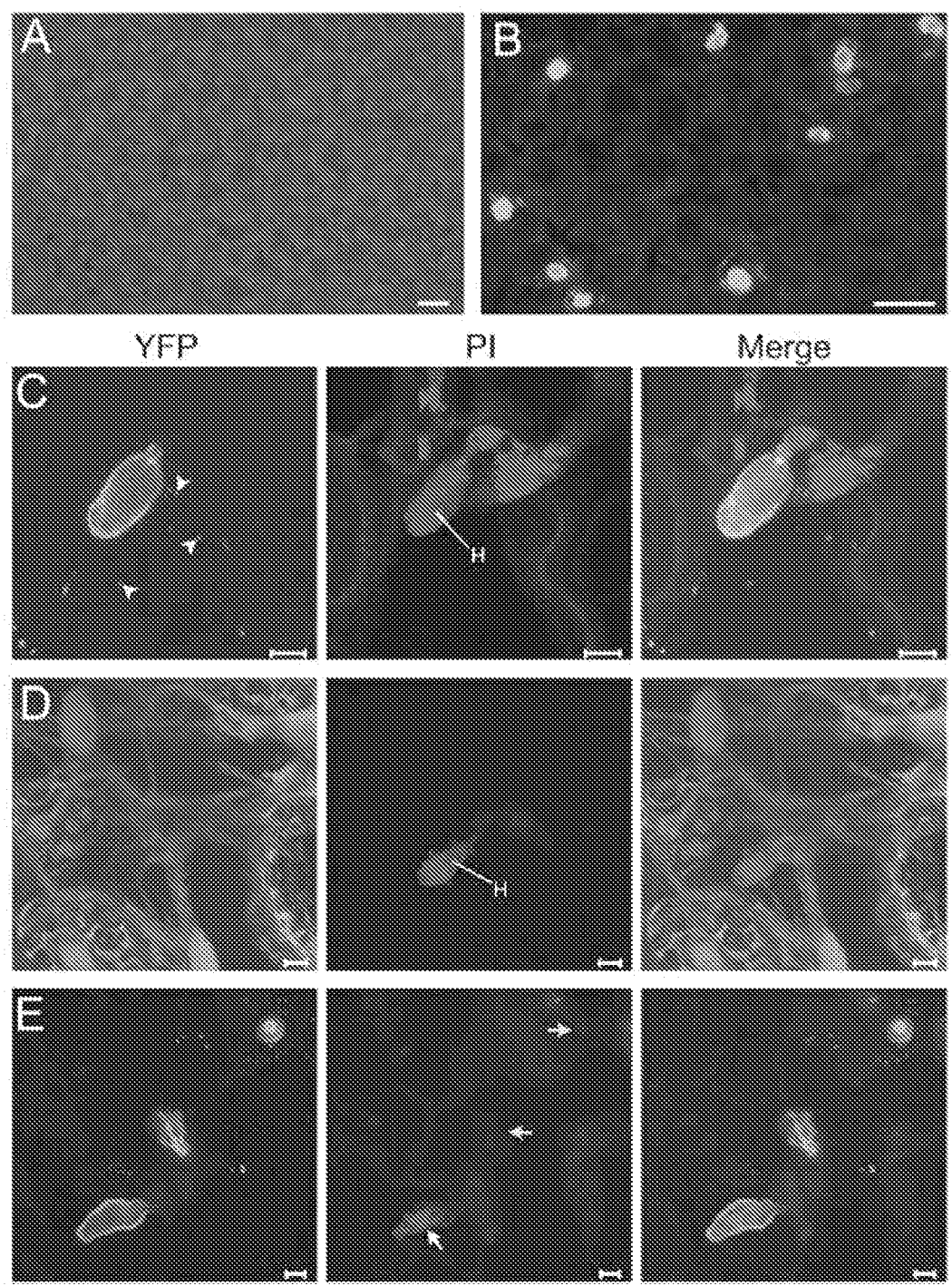
FIG. 1 shows that RPW8.2 is targeted to the periphery of the fungal haustorium. Except as noted, Col-0 lines expressing RPW8.2-YFP from the native RPW8.2 promoter were inoculated with *G. cichoracearum* UCSC 1, directly examined under a Zeiss epifluorescence microscope (A-B), or stained with propidium iodide (PT) to visualize the fungal structures and imaged by laser scanning confocal microscopy at 20-42 hours post-inoculation (hpi). Scale bars are 50 µm (A, B), 5 µm in (C-E).

RPW8.2 is Induced by Fungal Invasion and Targeted to the Host-Pathogen Interface In previous studies, The RPW8.1-YFP fusion protein expressed from the native promoter was mainly found in mesophyll cells, and rarely if ever observed in epidermal cells, whereas RPW8.2-YFP was detected in both epidermal as well as mesophyll cells (Wang et al., 2007). Because powdery mildew pathogens invade only plant epidermal cells via direct penetration the mode-of-action of RPW8.2 in the epidermal cells was studied. A small proportion (~5%) of RPW8.2-YFP transgenic lines developed spontaneous cell death associated with punctate RPW8.2-YFP expression, suggesting that RPW8.2-YFP retains the ability to trigger cell death (See FIG. 7A). Transgenic lines (single transgene, T4 generation) showing no constitutive RPW8.2-YFP expression (FIG. 1A) were selected to examine the expression and localization of RPW8.2-YFP in leaves after inoculation of *G. cichoracearum* (Gc) UCSC1. Remarkably, it was observed many sac-like fluorescent spheres in the size of 10-20 µm in the epidermal cells of the inoculated leaves (FIG. 1B). Such fluorescent spheres were detectable at 16-20 hours post-inoculation (hpi), overlapping with the haustorial differentiation from 12-18 hpi (Koh et al., 2005). Visualizing the fungal structures by propidium iodide (PI) staining revealed that the fluorescent spheres were in the vicinity of fungal mycelia (FIG. 7B). Close examination revealed that the fluorescent signal from RPW8.2-YFP precisely colocalized with fungal haustoria as shown in FIG. 1C. More significantly, in the cell accommodating the developing haustorium, small RPW8.2-YFP-positive vesicles of varied size could be seen to be moving towards and fusing into a membrane-like layer peripheral to the haustorium (arrowheads in FIG. 1C). Initially, the RPW8.2-YFP-labeled fluorescent layer encasing an incipient haustorium appeared punctate, uneven, and small in size (FIG. 7 C). As the haustorium continued to develop, the punctate layer progressively turned into a more evenly distributed coat encasing the haustorium (FIG. 1C). The global distribution of the fluorescent signals was observed in Col-0 cells expressing the YFP protein alone under control of the 35S promoter (FIG. 1 D), indicating that the haustorium-associated localization of RPW8.2-YFP was determined by RPW8.2. Furthermore, compared with healthy, plump haustoria in cells of Col-0 expressing 35S:: YFP, RPW8.2-YFP-encased haustoria, often although not always, appeared deformed or shrunken, and in some cases lacked PI staining (arrows in FIG. 1E). These findings, together with the observation that RPW8 does not seem to affect fungal spore germination (FIG. 8), suggest that RPW8.2 is specifically targeted to the periphery of the haustorium of Gc UCSC1 (i.e. the host-pathogen interface) to activate post-invasion, haustorium-targeted resistance.

To determine if the haustorium-specific targeting of RPW8 also occurs in interactions with non-host powdery mildew pathogens, RPW8.2-YFP was introduced into the eds1-2 mutant which exhibits compromised both non-host and host resistance (Aarts et al., 1998; Falk et al., 1999), and inoculated the plants with barley powdery mildew (*Blumeria graminis* f. sp. *horde*, Bgh) for which *Arabidopsis* is a nonhost. Haustorium formation was observed for Bgh albeit at a very low frequency. In cells invaded by haustoria, RPW8.2-YFP was either found to be colocalized with the aborted haustorium or an outlayer half-encasing the mature haustorium starting from the haustorial neck (FIGS. 9A and 9B), which is reminiscent of the observation that the callosic encasement of the HC (referred to as EHC in this study) induced in *Arabidopsis*-Bgh interaction was incomplete and showed a similar inverted cup-shape (Meyer et al., 2008). This result suggests that the haustorium-specific-targeting property of RPW8.2 might have evolved in the early stage of powdery mildew's adaptation to the *Arabidopsis* host.

Algae-like oomycete pathogens enter plant leaf tissues through natural pores such as stomates and subsequently penetrate mesophyll and occasionally epidermal cells to develop similar haustorial feeding structures for nutrient uptake. To determine if RPW8.2 is also targeted to the haustoirum of oomycete pathogens, 4 week-old, RPW8.2-YFP expressing seedlings inoculated with *Hyaloperonospora parasitica* (Hp) Noco2 at 2 dpi were examined to observe that accumulation of RPW8.2-YFP in the periphery of the oomycete haustoria (FIGS. 9C and 9 D).

To exclude the possibility that localization of RPW8.2 to the host-pathogen interface is induced by membrane damage and the subsequent repair process during haustorial invasion, Gc USCS1-inoculated plants expressing RPW8.2-YFP were wounded and found no induction or translocation of RPW8.2-YFP to the damaged PM (FIG. 10). These observations suggest that it is the differentiation of the haustorium, rather than mechanical perturbation of the PM, that induces RPW8.2 translocation to the host-pathogen interface.

RPW8.2 is Localized to the Extra-Haustorial Membrane

To determine the precise localization of RPW8.2 at the host-pathogen interface, individual haustorial complexes (HCs) were isolated, stained them with PI, and examined by LSCM. The EHM, and the haustorial PM and cell wall, together with the extrahaustorial matrix (EHX) in between, comprise the host-pathogen interface (Mackie et al., 1991; Szabo and Bushnell, 2001) (FIG. 11). The interfacial EHM (indicated by an arrowhead in FIG. 2A) is recognizable from an isolated HC from Col-0. Yellow fluorescence from RPW8.2-YFP was indeed precisely colocalized with the PI-positive, EHM of the HC isolated from Col-0 cells expressing RPW8.2-YFP (FIG. 2B). Interestingly, a 5-10 µm thick, weakly PI-positive layer was visible in some HCs isolated from RPW8.2-YFP cells (FIG. 2C). This layer corresponds to the callosic EHC. When a portion of the RPW8.2-YFP-labeled layer of a single HC was photobleached, the fluorescence was largely recovered in 5 minutes (FIG. 2D), similar to that seen in the PM labeled by GFP-SIMIP (Cutler et al., 2000) (FIG. 2E), indicating that this layer possesses membrane-specific fluidity.

Next, immunolocalization assay of leaf sections of inoculated RPW8.2-YFP plants were performed using an anti-GFP antibody conjugated to gold particles. Under transmission electron microscopy (TEM), the EHM is discernable as an electron-dense layer surrounding the HC (Gil and Gay, 1977). The observed shrinkage and deterioration of the haustoria targeted by RPW8.2-YFP (FIG. 1D), may account for the poor preservation of the haustorial structure observed by TEM (FIGS. 3A and 3B). Nevertheless, immunogold-labeled particles were found mainly at or attaching to the discernable EHM in sections of leaf samples from RPW8.2-YFP plants (FIGS. 3A and 3B), but not in the negative control of Col-0 (FIGS. 3C and D), indicating that the immunogold labeling was specific and RPW8.2-YFP was indeed localized at the EHM. Some clustered gold particles were also detected in the cytoplasmic side of the deformed HC where the EHC resides (FIG. 3B), likely representing RPW8.2-YFP vesicles. Based on these observations, it was concluded that RPW8.2 is induced and specifically targeted to the EHM during haustorial differentiation of Gc UCSC1 and that the EHM is indeed a special type of membrane distinct from the host cell PM.

RPW8.2 Trafficking Requires Functions of Actin Cytoskeleton

RPW8-mediated resistance engages SA-signaling (Xiao et al., 2003). To determine if SA-signaling is necessary for targeting RPW8.2 to the EHM, RPW8.2-YFP was introduced in Col-0 expressing NahG, or mutants eds1-2, eds5-1, pad4-1 or npr1-1 (each of which compromises SA-signaling) by stable transformation. RPW8.2-YFP expression and translocation to the EHM (FIG. 12A) was detected in 15-25% of the transgenic lines but most if not all of these plants were fully susceptible to Gc UCSC 1. Thus, despite its critical role in RPW8-mediated defense, SA-signaling is not required for targeting RPW8.2 to the EHM.

To determine if RPW8.2-YFP is targeted to the EHM via the endoplasmic reticulum (ER)-Golgi pathway, RPW8.2-DsRed was transiently co-expressed in Col-0 leaf epidermal cells with a trans Golgi marker GFP-SYP41 (Uemura et al., 2004). Although RPW8.2-YFP was not obviously colocalized with the Golgi marker GFP-ERD2 (Wang et al., 2007), it was found that in some cells RPW8.2-DsRed exhibited overlapping localization with GFP-SYP41 (FIG. 4A). This suggests that RPW8.2 is likely targeted to the EHM via the ER-Golgi trafficking pathway.

Because actin cytoskeleton is required for vesicle transport (Lanzetti, 2007), reorganized in hosts cells challenged by powdery mildew or oomycete pathogens (Takemoto et al., 2003; Opalski et al., 2005), and required for resistance against powdery mildew and oomycete pathogens (Yun et al., 2003; Miklis et al., 2007), it was necessary to investigate whether specific targeting of RPW8.2 to the EHM requires normal function of cytoskeleton. Cytochalasin E, an inhibitor of actin microfilaments or oryzalin, an inhibitor of microtubules was infiltrated into Gc USCS1-inoculated leaves of a Col-0 line transgenic for RPW8.2-YFP (R2Y4) at ~12 hpi and counted the number of RPW8.2-YFP labeled haustoria under an epifluorescent microscope from 32 to 36 hpi and subsequently stained the leaves by trypan blue for visualization and counting of all haustoria. It was found that compared with buffer control, cytochalasin E treatment (2-8 µg/ml) significantly reduced EHM-localization of RPW8.2-YFP, with the ratios of RPW8.2-YFP-labeled haustoria versus the total haustoria being 15-40% compared to ~70% for buffer control (FIG. 4B). The reduction of RPW8.2-YFP's EHM localization was often accompanied with irregular localization of RPW8.2-YFP peripheral to the PM of the haustorium-invaded epidermal cells and punctate RPW8.2-YFP spots in mesophyll cells underneath, and fungus-induced cell death (FIG. 13A). In contrast, oryzalin treatment did not affect RPW8.2-YFP's localization to the EHM (FIG. 4D).

To further establish the role of actin cytoskeleton in RPW8.2 trafficking, two *Arabidopsis* actin depolymerizing genes ADF5 and ADF6 were overexpressed in Col-0 or R2Y4. Col-0 T1 lines expressing 35S::ADF5 or 35S::ADF6 showed no noticeable phenotypes (data not shown). T1 lines (>60 examined) of R2Y4 transgenic for 35S::ADF5 were similar to R2Y4 in plant morphology (FIG. 13B) and EHM-localization of RPW8.2-YFP (data not shown). In contrast, 3 1% (22 of 7 1) 35S:ADF6 transgenic T1 lines (and their T2 progenies) exhibited reduced plant stature and developed spontaneous cell death in leaves (FIG. 13B). The development of cell death was proceeded by constitutive punctuate RPW8.2-YFP expression and $H_2O_2$ accumulation (FIGS. 4C and 4D). More significantly, localization of RPW8.2-YFP to the EHM was greatly reduced in these 35S:ADF6 lines with cell death (FIG. 4E). Reverse-transcription (RT) PCR showed that ADF6 was indeed expressed at higher levels in the lines that exhibited cell death, reduced size and compromised EHM-localization of RPW8.2-YFP (FIG. 13D). Together, these results demonstrated that specific targeting of RPW8.2 to the EHM is largely actin cytoskeleton-dependent, and microtubule-independent.

The PEN1 syntaxin contributes to pre-invasion (penetration) resistance of plants against non-adapted powdery mildew pathogens and is recently found to be enriched in the EHC along with several other associated SNARE proteins (Collins et al., 2003; Kwon et al., 2008; Meyer et al., 2008). It was tested to determine if the PEN1-dependent exocytosis pathway contributes to docking and fusion of RPW8.2 vesicles with the EHM. RPW8.2-YFP was introduced into PEN1 loss-of-function mutation (pen1-1) background and found that RPW8.2-YFP's translocation to the EHM was not grossly affected (FIG. 12A). Then plants expressing RPW8.2-DsRed and GFP-PEN1 in the pen1-1 background were generated and found that in addition to the PM and the papillae as reported (Assaad et al., 2004; Bhat et al., 2005), GFP-PEN1 was indeed found in the EHC but had no obvious overlapping with the RPW8.2-DsRed-labeled EHM (FIG. 12B). No colocalization of GFP-PEN1 with RPW8.2-YFP in punctate spots (data not shown). These observations suggested that a PEN1-independent/redundant, targeted protein-trafficking pathway is recruited for docking and fusion of RPW8.2 vesicles with the EHM.

RPW8.2 Enhances the Formation of the Callosic Extrahaustorial Encasement

The specific EHM-localization of RPW8.2 provides a perfect physical explanation for its broad-spectrum mildew resistance against *Golovinomyces* spp (Xiao et al., 2001). This further prompted an investigation to determine how RPW8.2's EHM-localization contributes to antifungal defenses at the host-pathogen interface. To address this question, trypan blue-stained, haustorium-invaded epidermal cells of Col-0, Ms-0, Col-0 lines transgenic for RPW8 (S5) or RPW8.2-YFP (R2Y4) or YFP alone (as control) were examined. Three types of haustorium-invaded cells were detected: (a) Viable cells containing a deformed or shrunken haustorium with a 5-10 µm thick, callose-rich layer designated EHC, which was discernable under differential interference contrast (DIC) microscopy or after trypan blue/aniline blue staining (indicated by black arrows in FIG. 5A; upper panel of FIG. 5B); (b) Cells undergoing HR (indicated by the red arrow in FIG. 5A, note that the EHC may have developed in these cells); (c) Viable cells with a healthy haustorium without the EHC (indicated by yellow arrows in FIG. 5A; lower panel of FIG. 5B, note the lack of an EHC but presence of a papilla). It was found that Ms-0, S5 and R2Y4, which were resistant to powdery mildew had 8-10 times higher ratios of type "a"+type "b" cells than Col-0 or Col-0 expressing YFP alone in both assays conducted at 42 hpi or 120 hpi (FIG. 5C). These observations suggest that RPW8-mediated resistance is associated not only with HR (type "b" cells) (Xiao et al., 2001) but also with EHC development (type "a" cells). The earliest time the EHC could be detected in R2Y4 is around 24 hpi, which is ~7 hours after RPW8.2-EHM localization is first detectable. Callosic haustorial encasements equivalent to the EHC have been reported to occur with a similar kinetics in the epidermal cells of *Arabidopsis* Col-0 invaded by the virulent powdery mildew isolate *G. orontii* (albeit at a lower rate) (Jacobs et al., 2003; Meyer et al., 2008). Examination of 11 additional *Arabidopsis* accessions for the HR, the EHC and resistance to Gc UCSC1 further established a correlation between EHC formation and resistance (FIG. 14A). Notably, in some fungal colonies found in Wa-1 (an accession containing identical RPW8 alleles as Ms-0) under low light (~85 µmol·m2·s1; 8 hrs/day) conditions, all invading haustoria were found to be associated with the EHC and further fungal growth was arrested without obvious HR (FIG. 14B). To see if RPW8-enhanced EHC formation is dependent on SA signaling, NahG (a bacterial gene encoding an SA hydrolase that depletes SA) or pad4-1 (a loss-of-function mutation of PAD4) that impairs SA signaling was combined into S5 and found that EHC formation was significantly reduced in these lines (FIG. 5D). Together, these results suggest that RPW8-mediated broad-spectrum mildew resistance is achieved at least in part by enhancing EHC formation as part of SA-dependent basal defense.

RPW8.2 Enhances Accumulation of $H_2O_2$ in the Haustorial Complex

It has been established that $H_2O_2$ production and accumulation precedes HR cell death and is associated with RPW8 resistance (Xiao et al., 2001; Xiao et al., 2003). To investigate how $H_2O_2$ is spatiotemporally involved in resistance in relation to RPW8.2's EHM-localization and subsequent EHC formation, $H_2O_2$ accumulation was monitored in single invaded epidermal cells. $H_2O_2$ accumulation in the invaded epidermal cells of Ms-0, S5 or R2Y4 was first detected around 27 hpi at a similar or slightly later time as the first appearance of the EHC. Three general patterns concerning $H_2O_2$ accumulation were observed in a time-frame from 27 to 72 hpi: (a) in the HC, (b) in the whole invaded cell and (c) no apparent $H_2O_2$ accumulation (FIG. 14C). Although there may not be a strict correlation between EHC formation and $H_2O_2$ accumulation, localized $H_2O_2$ accumulation in the HC (type "a") was always accompanied with EHC formation. This suggests that the EHC is necessary (though may not be sufficient) for localized $H_2O_2$ accumulation in the HC. To test this possibility, a loss-of-function mutation (pmr4-1) of PMR4/GSL5 encoding a glucan synthase-like membrane protein known to be required for onsite callose accumulation in response to haustorial invasion (Jacobs et al., 2003; Nishimura et al., 2003) was introduced into the S5 or R2Y4 (not shown) backgrounds to perturb the structural integrity of the EHC (Upper panel of FIG. 5E). As shown by representative images in the lower panel of FIG. 5E, in haustorium-invaded pmr4-1/S5 cells, $H_2O_2$ was often found to be in the cytoplasm even though it was more enriched in the HC. In contrast, $H_2O_2$ in the infected pmr4-1 cells showed less but more even distribution while $H_2O_2$ in S5 cells was often HC-confined. The increased frequency of whole-cell $H_2O_2$ accumulation correlated with a much higher percentage (>90%) of cells undergoing HR in pmr4-1/S5 compared with pmr4-1 or S5 alone (FIG. 5D). These results suggest that RPW8.2 triggers production and/or accumulation of $H_2O_2$ and concomitantly enhances EHC formation to confine $H_2O_2$ (perhaps other toxic defense compounds) at the HC, thereby inducing cost-effective resistance against powdery mildew.

RPW8.2 Proteins Encoded by Susceptible Alleles are Either Incapable of Activating Defense or Less Efficient in Trafficking to the EHM The majority of *Arabidopsis* accessions are susceptible or moderately susceptible to powdery mildew Gc UCSC1 (Adam et al., 1999; Orgil et al., 2007). To test if there is a correlation between functional diversification/deterioration of the RPW8.2 alleles and the mildew-susceptible phenotypes, the localization and function of RPW8.2 encoded by four alleles (Dra-0, Fm-3, Bu-23, Bg-1), each representing a distinct subgroup of divergent RPW8.2 alleles identified in *Arabidopsis* accessions was transgenically analyzed with a susceptible or intermediate disease phenotype (FIG. 15A; Orgil et al., 2007). Note that Bg-1 had been scored as resistant but reclassified as intermediate in this study after repeated careful infection tests, FIG. 15B). Col-0 transgenic lines (>120 T1 individuals and 20 independent T2 progenies) expressing RPW8.2$^x$-YFP (X denotes any of the four alleles) from the same RPW8.2$^{Ms-0}$ promoter were examined for disease infection phenotypes and protein localization. All transgenic plants expressing RPW8.2$^{Dra-0/Fm-3/Bu23}$-YFP were susceptible to Gc UCSC1; however EHM-localization of the corresponding fusion protein was readily detectable in those lines (30-49%) (FIG. 6A). In contrast, 41% (33/81) of Col-0 lines expressing RPW8.2$^{Bg-1}$-YFP exhibited constitutive punctate RPW8.2$^{Bg-1}$-YFP expression, strong spontaneous cell death and reduced plant size (FIG. 6B), and 22% (18/81) lines without spontaneous cell death developed Gc UCSC 1-induced massive cell death at 5-7 dpi, 2-3 days slower than the development normal HR (FIG. 6C). Examination of the infected leaves showed that RPW8.2$^{Bg-1}$-YFP was often detected as punctate spots in the invaded epidermal cells and rarely found in the EHM (FIG. 6A). Similar to plants of the Bg-1 accession, Col-0 plants transgenic for RPW8.2 BG-1-YFP supported moderate fungal growth despite development of massive fungus induced cell death at 8 dpi (FIGS. 6C and 15B). These observations suggested that RPW8.2$^{Bg-1}$ (and other$^{Bg-1}$ like alleles) may be more active than RPW8.2$^{Ms-0}$ in triggering cell death, and/or less efficient in EHM-localization, and therefore less effective in restricting fungal growth.

Discussion

The present invention reveals that RPW8-mediated broad-spectrum mildew resistance involves specific targeting of RPW8.2 to the host-fungal interfacial membrane and onsite activation of defenses against the invading pathogen. Heretofore it was not known RPW8.2 is the first protein ever identified in any host that is specifically targeted to the host-fungal pathogen interface for host defense. This finding has three important implications. First, the mysterious EHM does indeed exist and mostly likely is of host-origin and extensively modified by both the host and the pathogen. Second, plants have evolved elaborated mechanisms to activate defense at the host-pathogen interface to achieve cost-effective broad-spectrum resistance against haustorium-forming pathogens. Third, there exists an EHM-targeted protein trafficking pathway in plants for defense against haustorial invasion.

RPW8.2, the First Identified EHM-Specific Protein

The haustorium is a highly specialized feeding structure of plant pathogens falling into taxonomically distinct and agriculturally important species including the fungal powdery mildew (Ascomycetes) and rusts (Basidiomycetes), and the oomycetes. Concrete evidence has been provided for the two conceptual functions of the haustorium in pathogenesis: nutrient uptake from the host (Hahn and Mendgen, 2001; Szabo and Bushnell, 2001) and secretion of effectors into the host cell to suppress host defense (Catanzariti et al., 2007). However, the molecular warfare at the host-pathogen interface remains largely uncharacterized, mainly due to the lack of any specific molecular markers for the interfacial membrane, the EHM.

Previous searches for EHM-resident proteins in the field have had no or only limited success. By using a monoclonal antibody raised against the isolated HCs in pea infected with *Erysiphe pisi*, a glycoprotein (~250 kDa) was detected to be specifically localized to the periphery of the HC where the EHM was thought to form (Roberts et al., 1993). But the identity and origin of this glycoprotein still remains to be resolved. More recently, Koh and colleagues examined eight *Arabidopsis* PM-resident proteins powdery infected leaf cells and found they were all absent from the EHM (Koh et al., 2005). These observations suggest that the EHM by nature may be distinct from the normal host cell PM.

Clearly, RPW8.2 is specifically targeted, via intracellular vesicle transport, to the EHM during haustorium biogenesis, providing the first molecular marker for the haustorium-host cell interface (FIGS. 1-3). The highly specific localization of RPW8.2 to the EHM but not to the host PM also lends support to earlier observations that the EHM and the haustorial PM are sealed at the neck of the HC by two regions termed neckbands that serve to separate EHM and EHX from the host PM and the apoplastic space (Gil and Gay, 1977; Bushnell and Gay, 1978). The highly interface-specific localization of RPW8.2 is most striking and similar to the translocation of Nramp1 (natural-resistance-associated macrophage protein 1) and Lamp 1 (lysosomal-associated membrane protein 1) in activated animal macrophages to the host-pathogen interfacial (phagosomal) membrane from the late endocytic compartments (late endosome/lysosome) of resting macrophages (Searle et al., 1998; Canorme-Hergaux et al., 1999; Huynh et al., 2007). The present findings demonstrate for the first time that the EHM is indeed a special interfacial membrane likely of host-origin that may be extensively modified by the host and the pathogen for defense and pathogenesis, respectively. Thus, RPW8.2 can be used as a tool to investigate the molecular differentiation and composition of the EHM and targeted-defense mechanism of the host.

The host-pathogen interface localization of RPW8.2 is in sharp contrast to the dynamic nucleo-cytoplasmic distribution for several immunity proteins. It has recently been reported that subsequent to the perception of the cognate effector molecules from the pathogens, a small fraction of the NB-LRR proteins MLA10, N and RPS4 is translocated from the cytoplasm to the nucleus to activate immune response (Burch-Smith et al., 2007; Shen et al., 2007; Wirthmueller et al., 2007). NPR1, the central regulatory protein of systemic acquired resistance undergoes SA-induced oligomer-to-monomer conformational change and is subsequently translocated from the cytoplasm to the nucleus whereby it activates transcription of pathogenesis-related (PR) genes (Mou et al., 2003; Tada et al., 2008). Hence, based on protein localization, RPW8.2 does not seem to activate or regulate defense signaling through transcriptional reprogramming of the attack cells; instead, it behaves like a downstream defense protein specifically deployed at the host-pathogen battleground to fight against the invading haustorium.

Two Functional Arms of RPW8.2 Both Contribute to Cost-Effective Resistance

Targeting of RPW8.2 to the EHM and onsite activation defense response against the invading haustorium provides a clear mechanistic explanation for RPW8-mediated broad-spectrum mildew resistance. The genetic data shown herein suggest that trafficking of RPW8.2 to the EHM per se does not seem to require SA-signaling, because impairing the SA-pathway did not seem to affect EHM-localization of RPW8.2-YFP (FIG. 12). On the other hand, EHM-localization is not a prerequisite for RPW8.2-triggered to SA-dependent $H_2O_2$ production and cell death in the absence of pathogens. In fact, inhibition of the RPW8.2-YFP trafficking to the EHM by perturbing actin cytoskeleton actually resulted in $H_2O_2$ accumulation and cell death (FIGS. 4B-4E and 13). Thus, the two intrinsic functional arms of RPW8.2 appear to be regulated by different pathways. It is conceivable that these two functional arms must be properly coordinated to achieve cost-effective, haustorium-targeted resistance against powdery mildew pathogens. This is evidenced by the observations that RPW8.2 alleles from *Arabidopsis* accessions that are not resistant to Gc UCSC1 were found to encode proteins either unable to activate defense at the EHM (for the Dra-0, FM-3 and Bu-23 alleles) or less efficient in EHM-localization (for the Bg-1 allele) (FIGS. 6 and 15A). One may wonder why these divergent alleles have been maintained in the *Arabidopsis* population. A plausible explanation is that expression of RPW8.2Ms-0 (due to activation of SA-signaling upon insults from other pathogens) is costly in the absence of the powdery mildew pathogens, hence the generation and maintenance of RPW8.2 alleles defective in $H_2O_2$ production to reduce the cost associated with RPW8.2 expression (Orgil et al., 2007). However, it is difficult to explain the generation and maintenance of alleles that encode RPW8.2 more active in triggering cell death and/or less efficient in trafficking to the EHM. One possibility is that such RPW8.2 alleles may serve another (defense) function that may benefit the plant under certain environmental conditions and hence have been preserved in the population.

Dra-0 and Fm-3 differ from Ms-0 in RPW8.2 for only 3-5 amino acids (aa) (FIG. 15A). This points to a potential role of these residues (especially the T64S and D116G sites) in activation of SA-dependent defense. The Bu-23 allele lacks the C-terminal 31 aa. This suggests that at least the C-terminal 31 aa are dispensable for EHM-targeting. RPW8.2$^{Bg-1}$ differs from RPW8.2$^{Ms-0}$ in 13 aa. Apart from the 5 present in RPW8.2$^{Fm-3}$, most of the additional substitutions are located in the N-terminal 80 aa region. These substitutions may render the protein more active in cell death activation and/or less competent in trafficking.

Another intriguing feature of RPW8.2-mediated, haustorium-targeted defense is the concomitant EHC formation and $H_2O_2$ production/accumulation in the HC (FIGS. 5A-5C and 14B). Similar to papillae, the callosic EHC may provide a structural scaffold to contain, enrich and deliver toxic molecules produced by the host cell to constrain the haustorium, while protecting the host self from the toxic molecules such as $H_2O_2$. This is in line with previous observation that perturbation of EHC by pmr4-1 resulted in massive host cell death associated with fungus-induced $H_2O_2$ accumulation in the invaded epidermal cells (FIGS. 5D and 5E). It should be pointed out that the enhanced HR in pmr4-1/S5 plants may be caused by elevated SA signaling due to the pmr4-1 mutation (Nishimura et al., 2003) and the resultant amplification of RPW8-triggered defense response. However, there may exist a mechanistic connection between $H_2O_2$ accumulation in the cytoplasm of the invaded cells due to structural perturbation of the EHC (and papillae) and up-regulation of SA-signaling. Subcellular callosic structures similar to the EHC have long been observed in other host-pathogen interactions (Heath and Heath, 1971; Bushnell, 1972; Donofrio and Delaney, 2001; Mellersh and Heath, 2003; Soylu et al., 2003), suggesting that EHC formation may be a general basal defense against haustorium-forming pathogens and a target for pathogen suppression for pathogenesis. However, because there is rather frequent HR observed in RPW8-expressing plants, the HR may serve as a next, perhaps more destructive step to reinforce the earlier defense exerted by $H_2O_2$ in the HC that may not be sufficient to contain the adapted pathogen.

Existence of an EHM-Targeted Protein Trafficking Pathway

Polarized protein trafficking plays essential roles in multiple processes of plant development including cell division, pollen and root-hair tip growth (Bednarek and Falbel, 2002; Cole and Fowler, 2006; Yang, 2008). Specific targeting of RPW8.2 to the EHM suggested that there may exist a highly specific, EHM-targeted protein trafficking pathway recruited for defense against haustorial invasion and that there must be a targeting signal in RPW8.2 that is recognized by the trafficking machinery to guide the RPW8.2-residing vesicles to dock to and fuse with the EHM.

The PEN1 syntaxin defines a protein secretion pathway that plays an essential role for pre-invasion resistance (Collins et al., 2003). Its focal accumulation in the papillae well agrees with this function (Assaad et al., 2004). Recently, PEN1 and its SNARE partner SNAP33 were also found in the EHC (Meyer et al., 2008), implying a role of these proteins for resistance against haustorial invasion. To date, the cargo(s) of the PEN1-defined polarized secretion pathway has not been identified. Genetic analysis suggested that PEN1 is either dispensable or redundant for targeting of RPW8.2 to the EHM (FIG. 12B). Based on the observations that PEN1 (and its interacting partner SNAP33) were selectively incorporated into papillae and the EHC (Assaad et al., 2004; Meyer et al., 2008) but not in the EHM where RPW8.2 is localized (FIGS. 2 and 3), it is speculated herein that (i) at least two separate polarized/targeted protein trafficking pathways are activated during haustorial invasion, (ii) RPW8.2 is unlikely to be a cargo of the PEN1-dependent exocytosis pathway and (iii) a syntaxin(s) other than PEN1 may be recruited for the fusion of RPW8.2-containing vesicles with the EHM. Thus, RPW8.2 can be used as reporter protein to investigate the yet-to-be characterized, EHM-targeted protein-trafficking pathway evolved in plants for defense.

By taking a map-based cloning strategy, an R gene locus named RPW8 from *Arabidopsis thaliana* was identified and isolated that confers broad-spectrum resistance against all tested powdery mildew fungal pathogens belonging to different *Erysiphe* species of Ascomycete (Xiao et al., 1997; Xiao et al., 2001). The *A. thaliana* RPW8 locus in resistant accession Ms-0 contains two functional genes RPW8.1 and RPW8.2, whereas the susceptible accession Col-0 does not contain RPW8.1 or RPW8.2 but it contains a nonfunctional RPW8 homolog at the same position of RPW8.1 and RPW8.2 (Xiao et al., 2001; FIG. 16 A). As shown in FIG. 16 B, RPW8-containing plants (e.g. accession Ms-0) effectively resist fungal invasion by a hypersensitive response (HR), which is a form of programmed cell death activated at the fungal penetration site and visible to the naked eye as small flecks in the challenged leaf. Further development of the fungus is arrested. By contrast, RPW8-null plants (e.g. accession Col-0) supports profuse fungal growth, resulting in the formation of a snow-like layer of powdery mildew. RPW8.1 and RPW8.2 are predicted to encode two homologous novel proteins (17 and 20 kD, respectively) containing an putative N-terminal transmembrane (TM) domain with a C-terminal tail of ~140 amino acids that may contain 1-2 coiled coils (FIG. 16 A). The two RPW8 proteins share no significant homology to any other proteins outside of the RPW8 family in the database.

RPW8 Enhances the Formation of the Extrahaustorial Papillae (EHP)

Recently, a detailed comparative cytological analysis was conducted of leaf epidermal cells in RPW8-expressing or RPW8-null plants after inoculation with the powdery mildew isolate *E. cichoracearum* UCSC1 to investigate the initial subcellular events regulated by RPW8 in single invaded cells. It was found that the pathogen can penetrate the host cell wall by a structure called the appressorium at around 10 hours post-inoculation (hpi) equally well on both RPW8-expressing and RPW8-null leaf epidermal cells (data not shown), suggesting that RPW8 triggers post-penetration resistance. From ~20 hpi on, the fungus starts to differentiate the feeding structure called haustorium from the tip of the appressorium inside the penetrated host epidermal cell. The haustorium is a specialized single fungal cell in direct contact with the host cell. It is separated from the host cytoplasm by its own plasma membrane, cell wall, the host plasma membrane and the matrix in between (FIG. 17). Mature haustoria develop small lobes emanating from the main body presumably for taking up nutrition from the host cell. The haustorium is therefore the most critical structure of the fungus for successful colonization (Eichmann and Huckelhoven, 2008). As shown in FIG. 18, it was found that the majority (>25%) of haustoria formed inside the RPW8-expressing cells are often encased by an extrahaustorial papillae (EHP) (~4-6 µm in width) recognizable under light microscope, which contains callose (β-1,3 glucan polymers) and other chemicals thought to be involved in pathogen defense. However, only a small proportion (<3%) of haustoria in RPW8-null cells was found to be encased by the EHP. Histochemical staining revealed that $H_2O_2$ was rapidly produced and accumulated within EHP and inside the haustorium. Haustoria encased by the EHP were found to be either aborted, or shrunk while the host cells were still alive, suggesting that the function of the EHP is to constrain the fungal haustorium.

RPW8.2 is Induced and Translocated to the Host Plasma Membrane Encasing the Fungal Haustorium In order to understand how RPW8 enhances the formation of EHP, stable transgenic *Arabidopsis* plants expressing RPW8.1-YFP or RPW8.2-YFP fusion genes were generated under control of their native promoters (NP) and it was shown that both RPW8.1 and RPW8.2 are localized to the endomembranes and the plasma membrane and the endoplasmic reticulum (ER) in unchallenged leaf cells when overexpressed (Wang et al., 2007). These plants showed enhanced resistance to the pathogen (not shown), indicating the fusion protein is functional. Surprisingly, from ~20 hours after pathogen inoculation onward induction of sphere-like bright fluorescent bodies in the size of 15-20 µm was observed in the inoculated epidermal cells of the RPW8.2-YFP expressing plants (FIG. 19A), which coincides with the development of initial fungal haustoria inside the host cells. By visualizing the fungal haustoria with propidium iodide (PI) staining and confocal imaging, it was found that RPW8.2 is specifically transported from the ER to and accumulate in the host membrane encasing the fungal haustorium (referred to as the extrahaustorial membrane or EHM; FIG. 17A; FIGS. 19B&C).

RPW8.2:YFP appears to be initially deposited to the membrane at the neck of the haustorium (FIG. 19D), coinciding with the initiation of the EHM biogenesis. Photo-bleaching experiments showed that like the plasma membrane (FIG. 19F), the RPW8.2:YFP labeled EHM replenished in 7 minutes after depletion (FIG. 19E).

Immunogold-labeling coupled with transmission electron microscopy showed that RPW8.2:YFP is indeed localized to the membranous structure (EHM) periphery to the haustorium (FIGS. 19G&H). Confocal imaging also revealed active transport of RPW8.2:YFP in small vesicles in the size of less than 1 µm moving and fusing to the EHM encasing the haustorium (FIG. 20A) and the RPW8.2 intercepted haustoria often become aborted or shrunk (FIG. 20B), consistent with its role in enhancing the EHP formation (FIG. 18). Careful examination of individual haustoria isolated by multicentrifugation confirmed the association of RPW8.2:YFP and the EHP encasing the haustorium (FIG. 20C).

Many food and ornamental crops (wheat, barley, potato, tomato, cucumber, apple, grape, strawberry, rose etc) suffer huge losses due to mildew diseases caused by numerous haustorium-forming fungal and oomycete pathogens. Conventional disease control relies heavily on use of fungicide, which is not environmentally friendly. Utilization of the naturally evolved resistance in plants is the best approach to tackle these disease problems. However, due to the "arms race" between plants and their pathogens, plant R genes are specialized in controlling diseases caused by a narrow range of pathogens and/or not functional in different genetic backgrounds. For example, barley powdery mildew R genes can only recognize a strain of *Blumeria graminis* f. sp. *hordei* carrying the corresponding avirulence genes. RPW8 could function in tobacco, but does not seem to work in tomato (Xiao et al., 2003). In addition, RPW8-mediated resistance is associated with a fitness cost presumably due to too much host cell death during infection (Orgil et al., 2007). The findings set forth herein on the RPW8.2-EHM localization has promising practical potential: RPW8.2 can be engineered as a vector to specifically deliver peptides toxic to pathogens at the host-haustorium interface, creating durable, more cost-effective, broad-spectrum resistance against haustorium-forming pathogens.

RPW8.2 is a 20 kD protein that contains an N-terminal transmembrane (TM) domain and two coiled coils in its predicted cytoplasmic tail. Based on RPW8.2's localization and defense function, it is conceivable that apart from being capable of triggering reactive oxygen species (ROS) and nitric oxide (NO) production, RPW8.2 must possess a sorting signal that enables its highly specific translocation to the EHM. Extensive DNA deletion and transgenic analysis showed that apart from the transmembrane domain, a region containing 22 amino acids (VRKKFRYMRDIKEFEAKLR-WVV), (SEQ ID NO: 6) is essential for targeting of RPW8.2 to the EHM (FIG. 21). Interestingly, a "DIKE" (SEQ ID NO: 16) motif in this region appears to be highly conserved among the RPW8 gene family members.

A specific strategy was designed to target antifungal peptides across the host-pathogen interface. Specifically, the EHM-targeting signal in RPW8.2 is linked to antifungal proteins such as chitinases with a protein cleavage site (FRAL-SA) (SEQ ID NO: 17) specific for a NO-activated protease (subtilisin) which is also separately fused to the EHM-targeting signal. Then both DNA constructs are introduced as transgenes into *Arabidopsis* plants expressing RPW8.2-YFP by stable transformation. Once both fusion proteins are expressed in the host cell and specifically targeted to the HPI, RPW8.2-induced NO activates the protease, which in turn releases the antifungal proteins to the vicinity of the haustorium, thereby restricting the fungal development (FIG. 22).

REFERENCES

The contents of all references cited herein are incorporated by reference herein for all purposes.

Aarts, N., Metz, M., Holub, E., Staskawicz, B. J., Daniels, M. J., and Parker, J. E. (1998). Different requirements for EDS1 and NDR1 by disease resistance genes define at least two R gene-mediated signaling pathways in *Arabidopsis*. Proc Natl Acad Sci USA 95, 10306-10311.

Adam, L., Ellwood, S., Wilson, I., Saenz, G., Xiao, S., Oliver, R. P., Turner, J. G., and Somerville, S. (1999). Comparison of *Erysiphe cichoracearum* and *Ecruciferarum* and a survey of 360 *Arabidopsis thaliana* accessions for resistance to these two powdery mildew pathogens. Molecular Plant-Microbe Interactions 12, 103 1-1043.

Aist, J. R. (1976). Papillae and related wound plugs of plant cells Annual Review of Phytopathology 14, 145-163.

Assaad, F. F., Qiu, J. L., Youngs, H., Ehrhardt, D., Zimmerli, L., Kalde, M., Wanner, G., Peck, S. C., Edwards, H., Ramonell, K., Somerville, C. R., and Thordal-Christensen, H. (2004). The PEN1 syntaxin defines a novel cellular compartment upon fungal attack and is required for the timely assembly of papillae. Molecular biology of the cell 15, 5118-5129.

Bednarek, P., Pislewska-Bednarek, M., Svatos, A., Schneider, B., Doubsky, J., Mansurova, M., Humphry, M., Consonni, C., Panstruga, R., Sanchez-Vallet, A., Molina, A., and Schulze-Lefert, P. (2009). A glucosinolate metabolism pathway in living plant cells mediates broad-spectrum antifungal defense. Science (New York, N.Y. 323, 101-106.

Bednarek, S. Y., and Falbel, T. G. (2002). Membrane trafficking during plant cytokinesis. Traffic 3, 62 1-629.

Bhat, R. A., Miklis, M., Schmelzer, E., Schulze-Lefert, P., and Panstruga, R. (2005). Recruitment and interaction dynamics of plant penetration resistance components in a plasma membrane microdomain. Proc Natl Acad Sci USA 102, 3135-3140.

Braun, U. (1987). A monograph of the Erysiphales (Powdery mildews). (Stuttgart: Gebr. Borntraeger).

Burch-Smith, T. M., Schiff, M., Caplan, J. L., Tsao, J., Czymmek, K., and DineshKumar, S. P. (2007). A novel role for the TIR domain in association with pathogen-derived elicitors. PLoS biology 5, e68.

Bushnell, W. R. (1972). Physiology of fungal haustoria. Ann. Rev. Phytopathol. 10, 151-176.

Bushnell, W. R., and Gay, J. L. (1978). Accumulation of solutes in relation to the structure and function of haustoria in powdery mildews. In The Powdery Mildews, D. M. Spencer, ed (London: Academic Press), pp. 183-235.

Canorme-Hergaux, F., Gruenheid, S., Govoni, G., and Gros, P. (1999). The Nramp1 protein and its role in resistance to infection and macrophage function. Proceedings of the Association of American Physicians 111, 283-289.

Catanzariti, A. M., Dodds, P. N., and Ellis, J. G. (2007). Avirulence proteins from haustoria-forming pathogens. FEMS Microbiol Lett 269, 181-188.

Clay, N. K., Adio, A. M., Denoux, C., Jander, G., and Ausubel, F. M. (2009). Glucosinolate metabolites required for an *Arabidopsis* innate immune response. Science (New York, N.Y. 323, 95-101.

Cole, R. A., and Fowler, J. E. (2006). Polarized growth: maintaining focus on the tip. Current opinion in plant biology 9, 579-588.

Collins, N. C., Thordal-Christensen, H., Lipka, V., Bau, S., Kombrink, E., Qiu, J. L., Huckelhoven, R., Stein, M., Freialdenhoven, A., Somerville, S. C., and Schulze-Lefert, P. (2003). SNARE-protein-mediated disease resistance at the plant cell wall. Nature 425, 973-977.

Cutler, S. R., Ehrhardt, D. W., Griffitts, J. S., and Somerville, C. R. (2000). Random GFP::cDNA fusions enable visualization of subcellular structures in cells of *Arabidopsis* at a high frequency. Proc Natl Acad Sci USA 97, 3718-3723.

Dangl, J. L., and Jones, J. D. (2001). Plant pathogens and integrated defense responses to infection. Nature 411, 826-833.

Donofrio, N. M., and Delaney, T. P. (2001). Abnormal callose response phenotype and hypersusceptibility to Peronospora parasitica in defense-compromised arabidopsis nim1-1 and salicylate hydroxylase-expressing plants. Mol Plant Microbe Interact 14, 439-450.

Earley, K. W., Haag, J. R., Pontes, O., Opper, K., Juehne, T., Song, K., and Pikaard, C. S. (2006). Gateway-compatible vectors for plant functional genomics and proteomics. Plant J 45, 616-629.

Eichmann, R., and Huckelhoven, R. (2008). Accommodation of powdery mildew fungi in intact plant cells. J Plant Physiol 165, 5-18.

Falk, A., Feys, B. J., Frost, L. N., Jones, J. D., Daniels, M. J., and Parker, J. E. (1999). EDS1, an essential component of R gene-mediated disease resistance in *Arabidopsis* has homology to eukaryotic lipases. Proc Natl Acad Sci USA 96, 3292-3297.

Gil, F., and Gay, J. L. (1977). Ultrastructural and physiological properties of the host interfacial components of the haustoria of *Erysiphe pisi* in vivo and in vitro. Physiol. Plant Pathol. 10, 1-12.

Hahn, M., and Mendgen, K. (2001). Signal and nutrient exchange at biotrophic plant-fungus interfaces. Current opinion in plant biology 4, 322-327.

Halterman, D., Zhou, F., Wei, F., Wise, R. P., and Schulze-Lefert, P. (2001). The MLA6 coiled-coil, NBS-LRR protein confers AvrMla6-dependent resistance specificity to *Blumeria graminis* f. sp. *hordei* in barley and wheat. Plant J 25, 335-348.

Halterman, D. A., and Wise, R. P. (2004). A single-amino acid substitution in the sixth leucine-rich repeat of barley MLA6 and MLA13 alleviates dependence on RAR1 for disease resistance signaling. Plant J 38, 2 15-226.

Hammond-Kosack, K. E., and Jones, J. D. (1997). Plant Disease Resistance Genes. Annu Rev Plant Physiol Plant Mol Biol 48, 575-607.

Heath, M. C., and Heath, I. B. (1971). Ultrastructure of an immune and susceptible reaction of cowpea leaves to rust infection. Physiol. Mol. Plant Pathol. 1, 277-287.

Huckelhoven, R., Fodor, J., Preis, C., and Kogel, K. H. (1999). Hypersensitive cell death and papilla formation in barley attacked by the powdery mildew fungus are associated with hydrogen peroxide but not with salicylic acid accumulation. Plant Physiol 119, 1251-1260.

Huynh, K. K., Eskelinen, E. L., Scott, C. C., Malevanets, A., Saftig, P., and Grinstein, S. (2007). LAMP proteins are required for fusion of lysosomes with phagosomes. The EMBO journal 26, 3 13-324.

Jacobs, A. K., Lipka, V., Burton, R. A., Panstruga, R., Strizhov, N., Schulze-Lefert, P., and Fincher, G. B. (2003). An *Arabidopsis* Callose Synthase, GSL5, Is Required for Wound and Papillary Callose Formation. Plant Cell 15, 2503-25 13.

Jones, J. D., and Dangl, J. L. (2006). The plant immune system. Nature 444, 323-329.

Koh, S., Andre, A., Edwards, H., Ehrhardt, D., and Somerville, S. (2005). *Arabidopsis thaliana* subcellular responses to compatible *Erysiphe cichoracearum* infections. Plant J 44, 5 16-529.

Kwon, C., Neu, C., Pajonk, S., Yun, H. S., Lipka, U., Humphry, M., Bau, S., Straus, M., Kwaaitaal, M., Rampelt, H., El Kasmi, F., Jurgens, G., Parker, J., Panstruga, R., Lipka, V., and Schulze-Lefert, P. (2008). Co-option of a default secretory pathway for plant immune responses. Nature 451, 835-840.

Lanzetti, L. (2007). Actin in membrane trafficking. Curr Opin Cell Biol 19, 453-458.

Lipka, V., Dittgen, J., Bednarek, P., Bhat, R., Wiermer, M., Stein, M., Landtag, J., Brandt, W., Rosahl, S., Scheel, D., Llorente, F., Molina, A., Parker, J., Somerville, S., and Schulze-Lefert, P. (2005). Pre- and postinvasion defenses both contribute to nonhost resistance in *Arabidopsis*. Science (New York, N.Y. 310, 1180-1183.

Mackie, A. J., Roberts, A. M., Callow, J. A., and Green, J. R. (1991). Molecular Differentiation in Pea Powdery-Mildew Haustoria—Identification of a 62-Kda N-Linked Glycoprotein Unique to the Haustorial Plasma-Membrane. Planta 183, 399-408.

Manners, J. M., and Gay, J. L. (1982). Transport, Translocation and Metabolism of C14-Labeled Photosynthates at the Host-Parasite Interface of *Pisum-Sativum* and *Erysiphe-Pisi*. New Phytologist 91, 22 1-244.

Mellersh, D. G., and Heath, M. C. (2003). An investigation into the involvement of defense signaling pathways in components of the nonhost resistance of *Arabidopsis thaliana* to rust fungi also reveals a model system for studying rust fungal compatibility. Mol Plant Microbe Interact 16, 398-404.

Meyer, D., Pajonk, S., Micali, C., O'Connell, R., and Schulze-Lefert, P. (2008). Extracellular transport and integration of plant secretory proteins into pathogen-induced cell wall compartments. Plant J.

Miklis, M., Consonni, C., Bhat, R. A., Lipka, V., Schulze-Lefert, P., and Panstruga, R. (2007). Barley Mlo Modulates Actin-dependent and Actin-independent Antifungal Defense Pathways at the Cell Periphery. Plant Physiol.

Morel, J. B., and Dangl, J. L. (1997). The hypersensitive response and the induction of cell death in plants. Cell Death and Differentiation 4, 67 1-683.

Mou, Z., Fan, W., and Dong, X. (2003). Inducers of plant systemic acquired resistance regulate NPR1 function through redox changes. Cell 113, 93 5-944.

Nishimura, M. T., Stein, M., Hou, B. H., Vogel, J. P., Edwards, H., and Somerville, S. C. (2003). Loss of a callose synthase results in salicylic acid-dependent disease resistance. Science (New York, N.Y. 301, 969-972.

Opalski, K. S., Schultheiss, H., Kogel, K. H., and Huckelhoven, R. (2005). The receptor-like MLO protein and the RAC/ROP family G-protein RACB modulate actin reorganization in barley attacked by the biotrophic powdery mildew fungus *Blumeria graminis* f.sp. *hordei*. Plant J 41, 29 1-303.

Orgil, U., Araki, H., Tangchaiburana, S., Berkey, R., and Xiao, S. (2007). Intraspecific Genetic Variations, Fitness Cost and Benefit of RPW8, A Disease Resistance Locus in *Arabidopsis thaliana*. Genetics 176, 23 17-2333.

Roberts, A. M., Mackie, A. J., Hathaway, V., Callow, J. A., and Green, J. R. (1993). Molecular Differentiation in the Extrahaustorial Membrane of Pea Powdery Mildew Haustoria at Early and Late Stages of Development. Physiological and Molecular Plant Pathology 43, 147-160.

Schulze-Lefert, P., and Panstruga, R. (2003). Establishment of biotrophy by parasitic fungi and reprogramming of host cells for disease resistance. Annu Rev Phytopathol 41, 641-667.

Searle, S., Bright, N. A., Roach, T. I., Atkinson, P. G., Barton, C. H., Meloen, R. H., and Blackwell, J. M. (1998). Localisation of Nramp1 in macrophages: modulation with activation and infection. Journal of cell science 111 (Pt 19), 2855-2866.

Shen, Q. H., Saijo, Y., Mauch, S., Biskup, C., Bieri, S., Keller, B., Seki, H., Ulker, B., Somssich, I. E., and Schulze-Lefert, P. (2007). Nuclear activity of MLA immune receptors links isolate-specific and basal disease-resistance responses. Science (New York, N.Y. 315, 1098-1103.

Soylu, S., Keshavarzi, M., Brown, I., and Mansfield, J. W. (2003). Ultrastructural characterisation of interactions between *Arabidopsis thaliana* and *Albugo candida*. Physiological and Molecular Plant Pathology 63, 201-211.

Stein, M., Dittgen, J., Sanchez-Rodriguez, C., Hou, B. H., Molina, A., Schulze-Lefert, P., Lipka, V., and Somerville, S. (2006). *Arabidopsis* PEN3/PDR8, an ATP binding cassette transporter, contributes to nonhost resistance to inappropriate pathogens that enter by direct penetration. Plant Cell 18, 731-746.

Szabo, L. J., and Bushnell, W. R. (2001). Hidden robbers: the role of fungal haustoria in parasitism of plants. Proc Natl Acad Sci USA 98, 7654-7655.

Tada, Y., Spoel, S. H., Pajerowska-Mukhtar, K., Mou, Z., Song, J., Wang, C., Zuo, J., and Dong, X. (2008). Plant immunity requires conformational charges of NPR1 via S-nitrosylation and thioredoxins. Science (New York, N.Y. 321, 952-956.

Takemoto, D., Jones, D. A., and Hardham, A. R. (2003). GFP-tagging of cell components reveals the dynamics of subcellular re-organization in response to infection of *Arabidopsis* by oomycete pathogens. Plant J 33, 775-792.

Uemura, T., Ueda, T., Ohniwa, R. L., Nakano, A., Takeyasu, K., and Sato, M. H. (2004). Systematic analysis of SNARE molecules in *Arabidopsis*: dissection of the post-Golgi network in plant cells. Cell Struct Funct 29, 49-65.

Voegele, R. T., Struck, C., Hahn, M., and Mendgen, K. (2001). The role of haustoria in sugar supply during infection of broad bean by the rust fungus *Uromyces* fabae. Proc Natl Acad Sci USA 98, 8133-8138.

Wang, W., Devoto, A., Turner, J. G., and Xiao, S. (2007). Expression of the membrane-associated resistance protein RPW8 enhances basal defense against biotrophic pathogens. Mol Plant Microbe Interact 20, 966-976.

Wirthmueller, L., Zhang, Y., Jones, J. D., and Parker, J. E. (2007). Nuclear accumulation of the *Arabidopsis* immune receptor RPS4 is necessary for triggering EDS1-dependent defense. Curr Biol 17, 2023-2029.

Xiao, S., Brown, S., Patrick, E., Brearley, C., and Turner, J. G. (2003). Enhanced transcription of the *Arabidopsis* disease resistance genes RPW8.1 and RPW8.2 via a salicylic acid-dependent amplification circuit is required for hypersensitive cell death. Plant Cell 15, 33-45.

Xiao, S., Ellwood, S., Calis, O., Patrick, E., Li, T., Coleman, M., and Turner, J. G. (2001). Broad-spectrum mildew resistance in *Arabidopsis thaliana* mediated by RPW8. Science (New York, N.Y. 291, 118-120.

Xiao, S., Calis, O., Patrick, E., Zhang, G., Charoenwattana, P., Muskett, P., Parker, J. E., and Turner, J. G. (2005). The atypical resistance gene, RPW8, recruits components of basal defense for powdery mildew resistance in *Arabidopsis*. Plant J 42, 95-110.

Xiao, S., Charoenwattana, P., Holcombe, L., and Turner, J. G. (2003). The *Arabidopsis* genes RPW8.1 and RPW8.2 confer induced resistance to powdery mildew diseases in tobacco. Mol Plant Microbe Interact 16, 289-294.

Xiao, S., Ellwood, S., Findlay, K., Oliver, R. P., and Turner, J. G. (1997). Characterization of three loci controlling resistance of *Arabidopsis thaliana* accession Ms-0 to two powdery mildew diseases. Plant J 12, 757-768.

Yahiaoui, N., Srichumpa, P., Dudler, R., and Keller, B. (2004). Genome analysis at different ploidy levels allows cloning of the powdery mildew resistance gene Pm3b from hexaploid wheat. Plant J 37, 528-538.

Yang, Z. (2008). Cell polarity signaling in *Arabidopsis* Annu Rev Cell Dev Biol 24, 55 1-575.

Yun, B. W., Atkinson, H. A., Gaborit, C., Greenland, A., Read, N. D., Pallas, J. A., and Loake, G. J. (2003). Loss of actin cytoskeletal function and EDS1 activity, in combination, severely compromises non-host resistance in *Arabidopsis* against wheat powdery mildew. Plant J 34, 768-777.

Zhou, F., Kurth, J., Wei, F., Elliott, C., Vale, G., Yahiaoui, N., Keller, B., Somerville, S., Wise, R., and Schulze-Lefert, P. (2001). Cell-autonomous expression of barley Mla1 confers race-specific resistance to the powdery mildew fungus via a Rar1-independent signaling pathway. Plant Cell 13, 337-350.

That which is claimed is:

1. A method for delivery of a toxic agent to a fungal haustorium in an infected plant cell, the method comprising:
   introducing a vector into a host plant cell, the vector comprising:
   a fusion gene comprising a nucleotide sequence encoding a RPW8 protein and a nucleotide sequence encoding an antipathogenic protein that is toxic to a specific a haustorium-forming pathogen, wherein the nucleotide sequence encodes for a RPW8 protein consisting of SEQ ID NO. 1 (RPW8.2) or a combination of SEQ ID NO. 1 (RPW8.2) and SEQ ID NO. 8 (RPW8.1) and whereby the RPW8 protein translocates to the EHM for delivery of the antipathogenic protein; and
   maintaining the cell under appropriate conditions for expression of the fusion protein and the transportation of the expressed RPW8 protein and expressed antipathogenic protein to the extrahaustorial membrane.

2. The method according to claim 1, wherein the nucleotide sequence encoding a RPW8 protein is SEQ ID NO: 7 or a combination of SEQ ID NO: 7 and SEQ ID NO: 9.

3. A method for transforming a plant, the method comprising:
   introducing into the plant an expression cassette comprising a nucleotide sequence encoding a RPW8 protein and a nucleotide sequence encoding an antipathogenic protein that inhibits or reduces the growth of a haustorium forming pathogen, wherein the nucleotide sequence encodes for a RPW8 protein consisting of SEQ ID NO. 1 (RPW8.2) or a combination of SEQ ID NO. 1 (RPW8.2) and SEQ ID NO. 8 (RPW8.1) and whereby the RPW8 protein translocates to the EHM for delivery of the antipathogenic protein at the extrahaustorial membrane.

4. The method according to claim 3, wherein the nucleotide sequence encoding a RPW8 protein is SEQ ID NO: 7 or a combination of SEQ ID NO: 7 and SEQ ID NO: 9.

\* \* \* \* \*

SEQUENCE LISTING

```
<160> NUMBER OF SEQ ID NOS: 17

<210> SEQ ID NO 1
<211> LENGTH: 174
<212> TYPE: PRT
<213> ORGANISM: Arabidopsis thaliana

<400> SEQUENCE: 1

Met Ile Ala Glu Val Ala Ala Gly Gly Ala Leu Gly Leu Ala Leu Ser
1               5                   10                  15

Val Leu His Glu Ala Val Lys Arg Ala Lys Asp Arg Ser Val Thr Thr
            20                  25                  30

Arg Phe Ile Leu His Arg Leu Glu Ala Thr Ile Asp Ser Ile Thr Pro
        35                  40                  45

Leu Val Val Gln Ile Asp Lys Phe Ser Glu Glu Met Glu Asp Ser Thr
    50                  55                  60

Ser Arg Lys Val Asn Lys Arg Leu Lys Leu Leu Leu Glu Asn Ala Val
65                  70                  75                  80

Ser Leu Val Glu Glu Asn Ala Glu Leu Arg Arg Arg Asn Val Arg Lys
                85                  90                  95

Lys Phe Arg Tyr Met Arg Asp Ile Lys Glu Phe Glu Ala Lys Leu Arg
            100                 105                 110

Trp Val Val Asp Val Asp Val Gln Val Asn Gln Leu Ala Asp Ile Lys
        115                 120                 125

Glu Leu Lys Ala Lys Met Ser Glu Ile Ser Thr Lys Leu Asp Lys Ile
    130                 135                 140

Met Pro Gln Pro Lys Phe Glu Ile His Ile Gly Trp Cys Ser Gly Lys
145                 150                 155                 160

Thr Asn Arg Ala Ile Arg Phe Thr Phe Cys Ser Asp Asp Ser
                165                 170

<210> SEQ ID NO 2
```

<211> LENGTH: 174
<212> TYPE: PRT
<213> ORGANISM: Artificial Sequence
<220> FEATURE:
<223> OTHER INFORMATION: Synthetic Construct

<400> SEQUENCE: 2

Met Ile Ala Glu Val Ala Ala Gly Gly Ala Leu Gly Leu Ala Leu Ser
1               5                   10                  15

Val Leu His Glu Ala Val Lys Arg Ala Lys Asp Arg Ser Val Thr Thr
            20                  25                  30

Arg Phe Ile Leu His Arg Leu Glu Ala Thr Ile Asp Ser Ile Thr Pro
        35                  40                  45

Leu Val Val Gln Ile Asp Lys Phe Ser Glu Glu Met Glu Asp Ser Ser
    50                  55                  60

Ser Arg Lys Val Asn Lys Arg Leu Lys Leu Leu Glu Asn Ala Val
65                  70                  75                  80

Ser Leu Val Glu Glu Asn Ala Glu Leu Arg Arg Arg Asn Val Arg Lys
                85                  90                  95

Lys Phe Arg Tyr Met Arg Asp Ile Lys Glu Phe Glu Ala Lys Leu Arg
            100                 105                 110

Trp Val Val Gly Val Asp Val Gln Val Asn Gln Leu Ala Asp Ile Lys
        115                 120                 125

Glu Leu Lys Ala Lys Met Ser Glu Ile Ser Thr Lys Leu Asp Lys Ile
    130                 135                 140

Met Pro Gln Pro Lys Phe Glu Ile His Ile Gly Trp Cys Ser Gly Lys
145                 150                 155                 160

Lys Asn Arg Ala Ile Arg Phe Thr Phe Cys Ser Asp Asp Ser
                165                 170

<210> SEQ ID NO 3
<211> LENGTH: 174
<212> TYPE: PRT
<213> ORGANISM: Artificial Sequence
<220> FEATURE:
<223> OTHER INFORMATION: Synthetic Construct

<400> SEQUENCE: 3

Met Ile Ala Glu Val Ala Ala Gly Gly Ala Leu Gly Leu Ala Leu Ser
1               5                   10                  15

Val Leu Gln Glu Ala Val Lys Arg Ala Lys Asp Arg Ser Val Thr Thr
            20                  25                  30

Arg Phe Ile Leu His Arg Leu Glu Ala Thr Ile Asp Ser Ile Thr Pro
        35                  40                  45

Leu Val Val Gln Ile Asp Lys Phe Ser Glu Glu Met Glu Asp Ser Ser
    50                  55                  60

Ser Arg Lys Val Asn Glu Arg Leu Lys Leu Leu Glu Asn Ala Val
65                  70                  75                  80

Ser Leu Val Glu Glu Asn Ala Glu Leu Arg Arg Arg Asn Val Arg Lys
                85                  90                  95

Lys Phe Arg Tyr Met Arg Asp Ile Lys Glu Phe Glu Ala Lys Leu Arg
            100                 105                 110

Trp Val Val Gly Val Asp Val Gln Val Asn Gln Leu Ala Asp Ile Lys
        115                 120                 125

Glu Leu Lys Ala Lys Met Ser Glu Ile Ser Thr Lys Leu Asp Lys Ile
    130                 135                 140

Met Pro Gln Pro Lys Phe Glu Ile His Ile Gly Trp Cys Ser Gly Lys

```
                145                 150                 155                 160
Lys Asn Arg Ala Ile Arg Phe Thr Phe Cys Ser Asp Asp Ser
                    165                 170

<210> SEQ ID NO 4
<211> LENGTH: 174
<212> TYPE: PRT
<213> ORGANISM: Artificial Sequence
<220> FEATURE:
<223> OTHER INFORMATION: Synthetic Construct

<400> SEQUENCE: 4

Met Ile Ala Glu Val Ala Ala Gly Gly Ala Leu Gly Leu Ala Leu Ser
1               5                   10                  15

Val Leu Gln Glu Ala Val Lys Arg Ala Lys Asp Arg Ser Val Thr Thr
                20                  25                  30

Arg Phe Ile Leu His Arg Leu Glu Ala Thr Ile Asp Thr Ile Thr Pro
            35                  40                  45

Leu Ile Val Lys Ile Asp Lys Leu Ser Glu Lys Met Glu Asp Ser Ser
        50                  55                  60

Ser Arg Lys Phe Asn Glu Arg Leu Lys Leu Leu Val Asn Ala Val
65                  70                  75                  80

Ser Leu Val Glu Glu Asn Ala Glu Leu Arg Arg Arg Asn Val Arg Lys
                85                  90                  95

Lys Phe Arg Tyr Met Arg Asp Ile Lys Glu Phe Glu Ala Lys Ile Arg
                100                 105                 110

Trp Val Val Gly Val Asp Val Gln Val Asn Gln Leu Ala Asp Ile Lys
            115                 120                 125

Glu Leu Lys Ala Lys Met Ser Glu Ile Ser Thr Lys Leu Asp Lys Ile
        130                 135                 140

Met Pro Gln Pro Lys Phe Glu Ile His Ile Gly Trp Cys Ser Gly Lys
145                 150                 155                 160

Lys Asn Arg Ala Ile Arg Phe Thr Phe Cys Ser Asp Asp Ser
                165                 170

<210> SEQ ID NO 5
<211> LENGTH: 143
<212> TYPE: PRT
<213> ORGANISM: Artificial Sequence
<220> FEATURE:
<223> OTHER INFORMATION: Synthetic Construct

<400> SEQUENCE: 5

Met Ile Ala Glu Val Ala Ala Gly Gly Ala Leu Gly Leu Ala Leu Ser
1               5                   10                  15

Phe Leu His Glu Ala Val Lys Arg Ala Lys Asp Arg Ser Val Thr Thr
                20                  25                  30

Arg Phe Ile Leu His Arg Leu Glu Ala Thr Ile Asp Ser Ile Thr Pro
            35                  40                  45

Leu Val Val Gln Ile Asp Lys Phe Ser Glu Glu Met Glu Asp Ser Ser
        50                  55                  60

Ser Arg Lys Val Asn Lys Arg Leu Lys Leu Leu Leu Glu Asn Ala Val
65                  70                  75                  80

Ser Leu Val Glu Glu Asn Ala Glu Leu Arg Arg Arg Asn Val Arg Lys
                85                  90                  95

Lys Phe Arg Tyr Met Arg Asp Ile Lys Glu Phe Glu Ala Lys Leu Arg
                100                 105                 110
```

Trp Val Val Gly Val Asp Val Gln Val Asn Gln Leu Ala Asp Ile Lys
            115                 120                 125

Glu Leu Lys Ala Lys Met Ser Glu Ile Ser Thr Lys Leu Asp Lys
    130                 135                 140

<210> SEQ ID NO 6
<211> LENGTH: 22
<212> TYPE: PRT
<213> ORGANISM: Artificial Sequence
<220> FEATURE:
<223> OTHER INFORMATION: Synthetic construct

<400> SEQUENCE: 6

Val Arg Lys Lys Phe Arg Tyr Met Arg Asp Ile Lys Glu Phe Glu Ala
1               5                   10                  15

Lys Leu Arg Trp Val Val
            20

<210> SEQ ID NO 7
<211> LENGTH: 925
<212> TYPE: DNA
<213> ORGANISM: Arabidopsis thaliana

<400> SEQUENCE: 7
tgaatttctc tttgtttaat aaccattggc acatttattt attttcaaag tatgtcatta     60
gattattcat attaatacat atatatgagt cgtttgacac aattgggaca tcaagaatca    120
tcactgcaga acgtaaatcg gatcgcacgg tttgttttc ctgaacacca gccgatgtgg    180
atttcaaact tcggttgagg cattattttg tcaagtttag tgctgatttc agacatcttg    240
gccttgagtt ctttgatatc agccaattga ttaacttgaa catccacatc taccacccat    300
cgtaatttag cttcgaactc tttgatatct ctcatgtacc taaagataaa caacacaaat    360
ataatacaca tgttattgac ttaattcata gtaaatgtta ggttttgata gatttagtac    420
tgttgggagt ttatggaaat cacatatagg aactatttag cacaaacctg aacttcttgc    480
gtacgtttct gcgtctcagc tccgcattct cctcaacaag agaaacagcg ttctcaagga    540
gaagcttaag acgttattg actttcctcg atgttgaatc ttccatttct tcactgaact    600
tatcaatttg aaccaccaac ggtgtgatac tatcgattgt agcttcgaga cggtgtaaga    660
tgaatcttgt ggttacagat ctatcttttg ctcttttgac ggcctcgtgg aggacactga    720
gagcaagtcc aagagcaccc cctgcggcaa cctcagcaat cattttcttg aaattagttt    780
gttagctctc gaggtgaaga gttttgatg agttatattg atgatattat tttgtttggt    840
aagaaaaata taagaccatc tattatatta tatagaggtg aatatttata attccttttt    900
cttctcaaat atttggtaaa gtgtt                                          925

<210> SEQ ID NO 8
<211> LENGTH: 148
<212> TYPE: PRT
<213> ORGANISM: Arabidopsis thaliana

<400> SEQUENCE: 8

Met Pro Ile Gly Glu Leu Ala Ile Gly Ala Val Leu Gly Val Gly Ala
1               5                   10                  15

Gln Ala Ile Tyr Asp Arg Phe Arg Lys Ala Arg Asp Ile Ser Phe Val
            20                  25                  30

His Arg Leu Cys Ala Thr Ile Leu Ser Ile Glu Pro Phe Leu Val Gln
        35                  40                  45

Ile Asp Lys Arg Ser Lys Val Glu Gly Ser Pro Leu Arg Glu Val Asn
 50                  55                  60

Glu Arg Leu Thr Cys Phe Leu Glu Leu Ala Tyr Val Phe Val Glu Ala
 65                  70                  75                  80

Tyr Pro Lys Leu Arg Arg Gln Val Leu Arg Lys Tyr Arg Tyr Ile
                 85                  90                  95

Lys Ala Ile Glu Thr Ile Glu Leu Ala Leu Arg Ser Ile Ile Val Val
             100                 105                 110

Asp Phe Gln Val Asp Gln Trp Asp Asp Ile Lys Glu Ile Lys Ala Lys
             115                 120                 125

Ile Ser Glu Met Asp Thr Lys Leu Ala Glu Val Ile Ser Ala Cys Ser
 130                 135                 140

Lys Ile Arg Ala
 145

<210> SEQ ID NO 9
<211> LENGTH: 842
<212> TYPE: DNA
<213> ORGANISM: Arabidopsis thaliana

<400> SEQUENCE: 9
tgagaaagag tttttcaata attatgggga ataagagaga gagagagaga aatagatttc      60
cgaaattgat tacaagaaga aataatttca acaaagtctc tgtttttttt tatcaagctc     120 ttatttact acaagcagaa ataacttcag caagtttagt gtccatttca gatatcttgg      180
ccttgatttc tttgatatcg tcccattgat caacttgaaa atccacaact attatgcttc     240
ttaatgcaag ttctatcgtt tcgattgctt tgatgtacct aaagataaac agaacaaaca     300
taatactcgt gttattttc cacaacatga taggttttgt acgtttagtg tttggagatt      360
atcgaaatca tgtaaaaaaa attgttacaa agaagaagat atttttctct aaaccattaa     420
actaagaaat taggcgatcc aaaaaccaat agaaattcat gtcatatata cgaacctgta     480
cttcctgagt acttgtctgc gtctgagttt cggataagcc tcaacaaaaa cataagctaa     540
ttcaaggaaa cacgtgagac gttcgttgac ttcccttaat ggtgaacctt ccactttact    600
ccgcttatcg atttgaacca aaaacggctc gatactaagg attgtagcgc agagacggtg    660
tacgaaagat atatctcttg cttttctgaa ccggtcgtaa atggcttggg ctccaactcc    720
aagaacagcc cctatcgcaa gctcaccaat cggcattttt tgaaagtagt tgtttagctc    780
tcgaggtgaa tatagaggaa tctatgtaca tggaaggatg gaaccatatt aaatagtttt    840
at                                                                  842

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
ggctttcaag atggcgacga                                                20

<210> SEQ ID NO 11
<211> LENGTH: 23
<212> TYPE: DNA
<213> ORGANISM: Artificial Sequence
<220> FEATURE:
<223> OTHER INFORMATION: Synthetic Construct

```
<400> SEQUENCE: 11
ctatttggca cggtcttgga taa                                          23

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct

<400> SEQUENCE: 12
gacttagcag gccaaatgca a                                            21

<210> SEQ ID NO 13
<211> LENGTH: 21
<212> TYPE: DNA
<213> ORGANISM: Artificial Sequence
<220> FEATURE:
<223> OTHER INFORMATION: Synthetic Construct

<400> SEQUENCE: 13
cttgctctca gttcgctcgt t                                            21

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
ggcatcaaga gcgcgactgt                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
gcggcgaggc gtgtatacat                                              20

<210> SEQ ID NO 16
<211> LENGTH: 4
<212> TYPE: PRT
<213> ORGANISM: Artificial Sequence
<220> FEATURE:
<223> OTHER INFORMATION: Synthetic Construct

<400> SEQUENCE: 16

Asp Ile Lys Glu
1

<210> SEQ ID NO 17
<211> LENGTH: 6
<212> TYPE: PRT
<213> ORGANISM: Artificial Sequence
<220> FEATURE:
<223> OTHER INFORMATION: Synthetic Construct

<400> SEQUENCE: 17

Phe Arg Ala Leu Ser Ala
1               5
```